(12) United States Patent
Burns et al.

(10) Patent No.: US 6,963,010 B2
(45) Date of Patent: Nov. 8, 2005

(54) HYDROPHOBIC POLYAMINE ANALOGS AND METHODS FOR THEIR USE

(75) Inventors: Mark R. Burns, Shoreline, WA (US); Gerard F. Graminski, Shoreline, WA (US)

(73) Assignee: MediQuest Therapeutics, Inc., Seattle, WA (US)

( * ) Notice: Subject to any disclaimer, the term of this patent is extended or adjusted under 35 U.S.C. 154(b) by 325 days.

(21) Appl. No.: 10/296,259

(22) PCT Filed: Jan. 8, 2002

(86) PCT No.: PCT/US02/00347

§ 371 (c)(1),
(2), (4) Date: Nov. 21, 2002

(87) PCT Pub. No.: WO02/053519

PCT Pub. Date: Jul. 11, 2002

(65) Prior Publication Data

US 2003/0187276 A1 Oct. 2, 2003

Related U.S. Application Data

(60) Provisional application No. 60/260,415, filed on Jan. 8, 2001.

(51) Int. Cl.[7] .................. C07C 233/05; A61K 31/16

(52) U.S. Cl. ................. 564/152; 564/84; 564/86; 564/98; 564/155; 564/159; 564/188; 564/198; 549/487; 549/488; 514/601; 514/602; 514/603; 514/605; 514/616; 514/623; 514/626; 514/461

(58) Field of Search .................. 564/84, 86, 98, 564/152, 155, 159, 188, 198; 549/487, 488; 514/461, 601, 602, 603, 605, 616, 623, 626

(56) References Cited

U.S. PATENT DOCUMENTS

| 5,541,230 | A | * | 7/1996 | Basu et al. ............. 514/642 |
| 5,654,287 | A | * | 8/1997 | Prakash et al. .......... 514/49 |
| 6,172,261 | B1 | * | 1/2001 | Vermeulin et al. ....... 564/84 |

FOREIGN PATENT DOCUMENTS

WO 97/33560 * 9/1997

* cited by examiner

*Primary Examiner*—Shailendra Kumar
(74) *Attorney, Agent, or Firm*—Connolly, Bove, Lodge & Hutz, LLP

(57) ABSTRACT

The disclosed invention provides new polyamine analogs and derivatives containing a hydrophobic region and a polyamine region as well as methods and compositions for their use.

16 Claims, 44 Drawing Sheets

|  | | IA7 | IB7 | IC7 | ID7 | IE7 | IF7 |
|---|---|---|---|---|---|---|---|
| 7 | (acid chloride) | IA7 | IB7 | IC7 | ID7 | IE7 | IF7 |
| 8 | (acid chloride) | IA8 | IB8 | IC8 | ID8 | IE8 | IF8 |
| 9 | (acid chloride) | IA9 | IB9 | IC9 | ID9 | IE9 | IF9 |
| 10 | (acid chloride) | IA10 | IB10 | IC10 | ID10 | IE10 | IF10 |
| 11 | (acid chloride) | IA11 | IB11 | IC11 | ID11 | IE11 | IF1 |
| 12 | (acid chloride) | IA12 | IB12 | IC12 | ID12 | IE12 | IF12 |
| 13 | (acid chloride) | IA13 | IB13 | IC13 | ID13 | IE13 | IF13 |
| 14 | (acid chloride) | IA14 | IB14 | IC14 | ID14 | IE14 | IF14 |
| 15 | (acid chloride) | IA15 | IB15 | IC15 | ID15 | IE15 | IF15 |

| | 16 | 17 | 18 | 19 | 20 | 21 | 22 | 23 |
|---|---|---|---|---|---|---|---|---|
| | 5 | 6 | 7 | 8 | 9 | 10 | 11 | 12 |
| IA | IA16 | IA17 | IA18 | IA19 | IA20 | IA21 | IA22 | IA23 |
| IB | IB16 | IB17 | IB18 | IB19 | IB20 | IB21 | IB22 | IB23 |
| IC | IC16 | IC17 | IC18 | IC19 | IC20 | IC21 | IC22 | IC23 |
| ID | ID16 | ID17 | ID18 | ID19 | ID20 | ID21 | ID22 | ID23 |
| IE | IE16 | IE17 | IE18 | IE19 | IE20 | IE21 | IE22 | IE23 |
| IF | IF16 | IF17 | IF18 | IF19 | IF20 | IF21 | IF22 | IF23 |

|   | 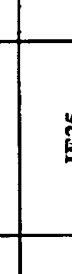 | IA24 | IB24 | IC24 | ID24 | IE24 | IF24 |
|---|---|---|---|---|---|---|---|
| 24 | 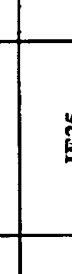 | IA24 | IB24 | IC24 | ID24 | IE24 | IF24 |
| 25 |  | IA25 | IB25 | IC25 | ID25 | IE25 | IF25 |
| 26 |  | IA26 | IB26 | IC26 | ID26 | IE26 | IF26 |
| 27 |  | IA27 | IB27 | IC27 | ID27 | IE27 | IF27 |
| 28 |  | IA28 | IB28 | IC28 | ID28 | IE28 | IF28 |
| 29 |  | IA29 | IB29 | IC29 | ID29 | IE29 | IF29 |
| 30 |  | IA30 | IB30 | IC30 | ID30 | IE30 | IF30 |
FIG. 2D

| | | IA31 | IB31 | IC31 | ID31 | IE31 | IF31 |
|---|---|---|---|---|---|---|---|
| 31 | (adamantyl-C(O)Cl) | IA31 | IB31 | IC31 | ID31 | IE31 | IF31 |
| 32 | (cyclohexyl-C(O)Cl) | IA32 | IB32 | IC32 | ID32 | IE32 | IF32 |
| 33 | (H₃C)₂CH-C(O)Cl | IA33 | IB33 | IC33 | ID33 | IE33 | IF33 |
| 34 | (H₃C)₃C-C(O)Cl | IA34 | IB34 | IC34 | ID34 | IE34 | IF34 |
| 35 | CH₃CH(CH₃)CH₂-C(O)Cl | IA35 | IB35 | IC35 | ID35 | IE35 | IF35 |
| 36 | (H₃C)₃C-CH₂-C(O)Cl | IA36 | IB36 | IC36 | ID36 | IE36 | IF36 |
| 37 | (norbornyl-CH₂-C(O)Cl) | IA37 | IB37 | IC37 | ID37 | IE37 | IF37 |
| 38 | (menthyloxyacetyl chloride) | IA38 | IB38 | IC38 | ID38 | IE38 | IF38 |
| 39 | F₃CF₂CF₂-C(O)Cl | IA39 | IB39 | IC39 | ID39 | IE39 | IF39 |

FIG. 2E

| | | | | | | |
|---|---|---|---|---|---|---|
| 40 | 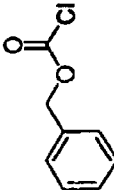 | IA40 | IB40 | IC40 | ID40 | IE40 | IF40 |
| 41 | 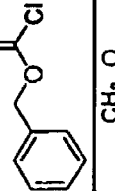 | IA41 | IB41 | IC41 | ID41 | IE41 | IF41 |
FIG. 2F

| | | A | B | C | D | E | F |
|---|---|---|---|---|---|---|---|
| | SERIES II | A (ε-L-Lys) | B (ε-D-Lys) | C (α-L-Lys) | D (α-L-Lys) | E (α,ε-L-Lys) | F (α, ε-D-Lys) |
| 1 | $CH_3SO_2Cl$ | IIA1 | IIB1 | IIC1 | IID1 | IIE1 | IIF1 |
| 2 | $CH_3CH_2SO_2Cl$ | IIA2 | IIB2 | IIC2 | IID2 | IIE2 | IIF2 |
| 3 | $CH_3(CH_2)_2SO_2Cl$ | IIA3 | IIB3 | IIC3 | IID3 | IIE3 | IIF3 |
| 4 | $CH_3(CH_2)_3SO_2Cl$ | IIA4 | IIB4 | IIC4 | IID4 | IIE4 | IIF4 |
| 5 | $CH_3(CH_2)_5SO_2Cl$ | IIA5 | IIB5 | IIC5 | IID5 | IIE5 | IIF5 |
| 6 | $CH_3(CH_2)_6SO_2Cl$ | IIA6 | IIB6 | IIC6 | IID6 | IIE6 | IIF6 |
| 7 | $CH_3(CH_2)_8SO_2Cl$ | IIA7 | IIB7 | IIC7 | IID7 | IIE7 | IIF7 |
| 8 | $CH_3(CH_2)_{10}SO_2Cl$ | IIA8 | IIB8 | IIC8 | IID8 | IIE8 | IIF8 |
| 9 | $CH_3(CH_2)_{12}SO_2Cl$ | IIA9 | IIB9 | IIC9 | IID9 | IIE9 | IIF9 |
| 10 | $CH_3(CH_2)_{14}SO_2Cl$ | IIA10 | IIB10 | IIC10 | IID10 | IIE10 | IIF10 |
| 11 | $CH_3(CH_2)_{15}SO_2Cl$ | IIA11 | IIB11 | IIC11 | IID11 | IIE11 | IIF11 |
| 12 | $CH_3(CH_2)_{16}SO_2Cl$ | IIA12 | IIB12 | IIC12 | IID12 | IIE12 | IIF12 |
| 13 | $CH_3(CH_2)_{17}SO_2Cl$ | IIA13 | IIB13 | IIC13 | IID13 | IIE13 | IIF13 |
| 14 | $CH_3(CH_2)_{18}SO_2Cl$ | IIA14 | IIB14 | IIC14 | IID14 | IIE14 | IIF14 |
| 15 | $CH_3(CH_2)_{19}SO_2Cl$ | IIA15 | IIB15 | IIC15 | IID15 | IIE15 | IIF15 |

FIG. 2G

| SERIES III | A <br/> ε-L-Lys | B <br/> ε-D-Lys | C <br/> α-L-Lys | D <br/> α-L-Lys | E <br/> α,ε-L-Lys | F <br/> α,ε-D-Lys |
|---|---|---|---|---|---|---|
| 1 | IIIA1 | IIIB1 | IIIC1 | IIID1 | IIIE1 | IIIF1 |
| 2 | IIIA2 | IIIB2 | IIIC2 | IIID2 | IIIE2 | IIIF2 |
| 3 | IIIA3 | IIIB3 | IIIC3 | IIID3 | IIIE3 | IIIF3 |
| 4 | IIIA4 | IIIB4 | IIIC4 | IIID4 | IIIE4 | IIIF4 |
| 5 | IIIA5 | IIIB5 | IIIC5 | IIID5 | IIIE5 | IIIF5 |

FIG. 21

| | 6 | 7 |
|---|---|---|
| [structure 6] | IIIA6 | IIIA7 |
| | IIIB6 | IIIB7 |
| | IIIC6 | IIIC7 |
| | IIID6 | IIID7 |
| | IIIE6 | IIIE7 |
| | IIIF6 | IIIF7 |
| [structure 7] | | |

FIG. 2J

| SERIES IV | | A | B | C | D | E | F |
|---|---|---|---|---|---|---|---|
| | | A (ε-L-Lys) | B (ε-D-Lys) | C (α-L-Lys) | D (α-L-Lys) | E (α,ε-L-Lys) | F (α,ε-D-Lys) |
| 1 | O=CH-CH₃ | IVA1 | IVB1 | IVC1 | IVD1 | IVE1 | IVF1 |
| 2 | O=CH-(CH₃)₁ | IVA2 | IVB2 | IVC2 | IVD2 | IVE2 | IVF2 |
| 3 | O=CH-(CH₃)₂ | IVA3 | IVB3 | IVC3 | IVD3 | IVE3 | IVF3 |
| 4 | O=CH-(CH₃)₃ | IVA4 | IVB4 | IVC4 | IVD4 | IVE4 | IVF4 |
| 5 | O=CH-(CH₃)₄ | IVA5 | IVB5 | IVC5 | IVD5 | IVE5 | IVF5 |
| 6 | O=CH-(CH₃)₅ | IVA6 | IVB6 | IVC6 | IVD6 | IVE6 | IVF6 |

FIG. 2K

| | | IVA7 | IVB7 | IVC7 | IVD7 | IVE7 | IVF7 |
|---|---|---|---|---|---|---|---|
| 7 | | | | | | | |
| 8 | | IVA8 | IVB8 | IVC8 | IVD8 | IVE8 | IVF8 |
| 9 | | IVA9 | IVB9 | IVC9 | IVD9 | IVE9 | IVF9 |
| 10 | | IVA10 | IVB10 | IVC10 | IVD10 | IVE10 | IVF10 |
| 11 | | IVA11 | IVB11 | IVC11 | IVD11 | IVE11 | IVF11 |
| 12 | | IVA12 | IVB12 | IVC12 | IVD12 | IVE12 | IVF12 |
| 13 | | IVA13 | IVB13 | IVC13 | IVD13 | IVE13 | IVF13 |
| 14 | | IVA14 | IVB14 | IVC14 | IVD14 | IVE14 | IVF14 |
| 15 | | IVA15 | IVB15 | IVC15 | IVD15 | IVE15 | IVF15 |

FIG. 2L

| | | | | | | | |
|---|---|---|---|---|---|---|---|
| 16 | 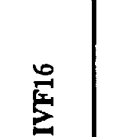 | IVA16 | IVB16 | IVC16 | IVD16 | IVE16 | IVF16 |
| 17 | 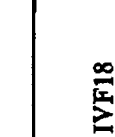 | IVA17 | IVB17 | IVC17 | IVD17 | IVE17 | IVF17 |
| 18 | 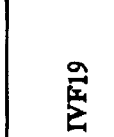 | IVA18 | IVB18 | IVC18 | IVD18 | IVE18 | IVF18 |
| 19 |  | IVA19 | IVB19 | IVC19 | IVD19 | IVE19 | IVF19 |
| 20 | 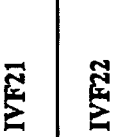 | IVA20 | IVB20 | IVC20 | IVD20 | IVE20 | IVF20 |
| 21 | 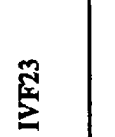 | IVA21 | IVB21 | IVC21 | IVD21 | IVE21 | IVF21 |
| 22 |  | IVA22 | IVB22 | IVC22 | IVD22 | IVE22 | IVF22 |
| 23 |  | IVA23 | IVB23 | IVC23 | IVD23 | IVE23 | IVF23 |
FIG. 2M

FIG. 2N

| | | | | | | | |
|---|---|---|---|---|---|---|---|
| 24 | (H₃C)₂CH-C(CH₃)-C(=O)H | IVA24 | IVB24 | IVC24 | IVD24 | IVE24 | IVF24 |
| 25 | norbornene-CHO | IVA25 | IVB25 | IVC25 | IVD25 | IVE25 | IVF25 |
| 26 | norbornane-CHO | IVA26 | IVB26 | IVC26 | IVD26 | IVE26 | IVF26 |
| 27 | cyclohexyl-CHO | IVA27 | IVB27 | IVC27 | IVD27 | IVE27 | IVF27 |
| 28 | citronellal | IVA28 | IVB28 | IVC28 | IVD28 | IVE28 | IVF28 |
| 29 | hydroxycitronellal | IVA29 | IVB29 | IVC29 | IVD29 | IVE29 | IVF29 |
| 30 | benzaldehyde | IVA30 | IVB30 | IVC30 | IVD30 | IVE30 | IVF30 |
| 31 | 2-phenylbenzaldehyde | IVA31 | IVB31 | IVC31 | IVD31 | IVE31 | IVF31 |

|  | 32 | 33 | 34 | 35 |
|---|---|---|---|---|
| | IVA32 | IVA33 | IVA34 | IVA35 |
| | IVB32 | IVB33 | IVB34 | IVB35 |
| | IVC32 | IVC33 | IVC34 | IVC35 |
| | IVD32 | IVD33 | IVD34 | IVD35 |
| | IVE32 | IVE33 | IVE34 | IVE35 |
| | IVF32 | IVF33 | IVF34 | IVF35 |

FIG. 20

|   | | VA8 | VB8 | VC8 | VD8 | VE8 | VF8 |
|---|---|---|---|---|---|---|---|
| 8 | 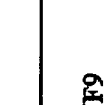 | VA8 | VB8 | VC8 | VD8 | VE8 | VF8 |
| 9 |  | VA9 | VB9 | VC9 | VD9 | VE9 | VF9 |
| 10 | 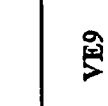 | VA10 | VB10 | VC10 | VD10 | VE10 | VF10 |
| 11 |  | VA11 | VB11 | VC11 | VD11 | VE11 | VF11 |
| 12 | 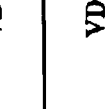 | VA12 | VB12 | VC12 | VD12 | VE12 | VF12 |
| 13 | 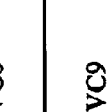 | VA13 | VB13 | VC13 | VD13 | VE13 | VF13 |
| 14 |  | VA14 | VB14 | VC14 | VD14 | VE14 | VF14 |
| 15 | 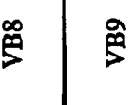 | VA15 | VB15 | VC15 | VD15 | VE15 | VF15 |
| 16 |  | VA16 | VB16 | VC16 | VD16 | VE16 | VF16 |
FIG. 2Q

| | | VB17 | VC17 | VD17 | VE17 | VF17 |
|---|---|---|---|---|---|---|
| 17 | VA17 | VB17 | VC17 | VD17 | VE17 | VF17 |
| 18 | VA18 | VB18 | VC18 | VD18 | VE18 | VF18 |
| 19 | VA19 | VB19 | VC19 | VD19 | VE19 | VF19 |
| 20 | VA20 | VB20 | VC20 | VD20 | VE20 | VF20 |
| 21 | VA21 | VB21 | VC21 | VD21 | VE21 | VF21 |
| 22 | VA22 | VB22 | VC22 | VD22 | VE22 | VF22 |
| 23 | VA23 | VB23 | VC23 | VD23 | VE23 | VF23 |
| 24 | VA24 | VB24 | VC24 | VD24 | VE24 | VF24 |

FIG. 2R

| | | VA25 | VB25 | VC25 | VD25 | VE25 | VF25 |
|---|---|---|---|---|---|---|---|
| 25 |  | VA25 | VB25 | VC25 | VD25 | VE25 | VF25 |
| 26 |  | VA26 | VB26 | VC26 | VD26 | VE26 | VF26 |
| 27 |  | VA27 | VB27 | VC27 | VD27 | VE27 | VF27 |
| 28 |  | VA28 | VB28 | VC28 | VD28 | VE28 | VF28 |
FIG. 2S

| SERIES VI | A | B | C | D | E | F |
|---|---|---|---|---|---|---|
| | A (ε-L-Lys) | B (ε-D-Lys) | C (α-L-Lys) | D (α-L-Lys) | E (α,ε-L-Lys) | F (α,ε-D-Lys) |
| 1 | VIA1 | VIB1 | VIC1 | VID1 | VIE1 | VIF1 |
| 2 | VIA2 | VIB2 | VIC2 | VID2 | VIE2 | VIF2 |
| 3 | VIA3 | VIB3 | VIC3 | VID3 | VIE3 | VIF3 |
| 4 | VIA4 | VIB4 | VIC4 | VID4 | VIE4 | VIF4 |
| 5 | VIA5 | VIB5 | VIC5 | VID5 | VIE5 | VIF5 |
| 6 | VIA6 | VIB6 | VIC6 | VID6 | VIE6 | VIF6 |
| 7 | VIA7 | VIB7 | VIC7 | VID7 | VIE7 | IVIF7 |

FIG. 2T

FIG. 2U
| | | | | | | | |
|---|---|---|---|---|---|---|---|
| 8 |  | VIA8 | VIB8 | VIC8 | VID8 | VIE8 | VIF8 |
| 9 | 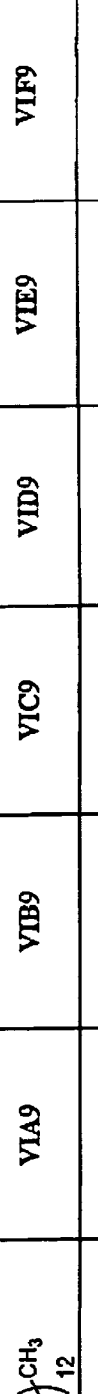 | VIA9 | VIB9 | VIC9 | VID9 | VIE9 | VIF9 |
| 10 |  | VIA10 | VIB10 | VIC10 | VID10 | VIE10 | VIF10 |
| 11 | 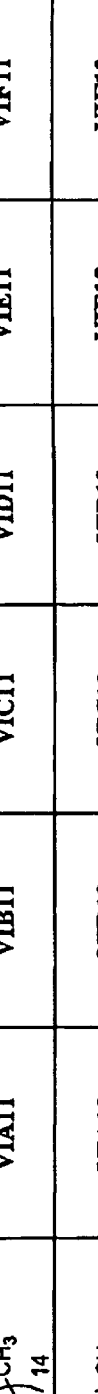 | VIA11 | VIB11 | VIC11 | VID11 | VIE11 | VIF11 |
| 12 |  | VIA12 | VIB12 | VIC12 | VID12 | VIE12 | VIF12 |
| 13 | 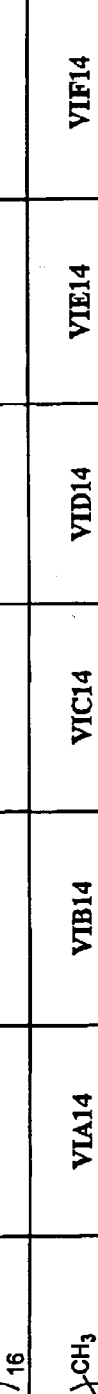 | VIA13 | VIB13 | VIC13 | VID13 | VIE13 | VIF13 |
| 14 | 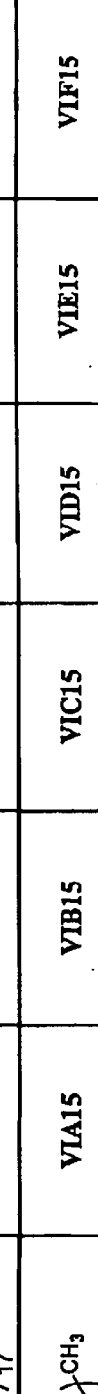 | VIA14 | VIB14 | VIC14 | VID14 | VIE14 | VIF14 |
| 15 | 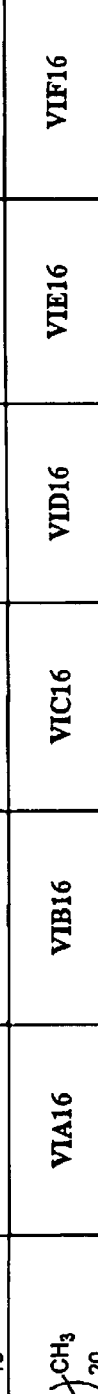 | VIA15 | VIB15 | VIC15 | VID15 | VIE15 | VIF15 |
| 16 |  | VIA16 | VIB16 | VIC16 | VID16 | VIE16 | VIF16 |

| | | | | | | | |
|---|---|---|---|---|---|---|---|
| 17 | (structure) | VIA17 | VIB17 | VIC17 | VID17 | VIE17 | VIF17 |
| 18 | (structure) | VIA18 | VIB18 | VIC18 | VID18 | VIE18 | VIF18 |
| 19 | (structure) | VIA19 | VIB19 | VIC19 | VID19 | VIE19 | VIF19 |
| 20 | (structure) | VIA20 | VIB20 | VIC20 | VID20 | VIE20 | VIF20 |
| 21 | (structure) | VIA21 | VIB21 | VIC21 | VID21 | VIE21 | VIF21 |
| 22 | (structure) | VIA22 | VIB22 | VIC22 | VID22 | VIE22 | VIF22 |
| 23 | (structure) | VIA23 | VIB23 | VIC23 | VID23 | VIE23 | VIF23 |
| 24 | (structure) | VIA24 | VIB24 | VIC24 | VID24 | VIE24 | VIF24 |
| 25 | (structure) | VIA25 | VIB25 | VIC25 | VID25 | VIE25 | VIF25 |

FIG. 2V

| | | VIA | VIB | VIC | VID | VIE | VIF |
|---|---|---|---|---|---|---|---|
| 26 | (norbornene carboxaldehyde) | VIA26 | VIB26 | VIC26 | VID26 | VIE26 | VIF26 |
| 27 | (norbornane carboxaldehyde) | VIA27 | VIB27 | VIC27 | VID27 | VIE27 | VIF27 |
| 28 | (cyclohexyl aldehyde) | VIA28 | VIB28 | VIC28 | VID28 | VIE28 | VIF28 |
| 29 | (citronellal) | VIA29 | VIB29 | VIC29 | VID29 | VIE29 | VIF29 |
| 30 | (hydroxycitronellal) | VIA30 | VIB30 | VIC30 | VID30 | VIE30 | VIF30 |
| 31 | (benzaldehyde) | VIA31 | VIB31 | VIC31 | VID31 | VIE31 | VIF31 |
| 32 | (biphenyl carboxaldehyde) | VIA32 | VIB32 | VIC32 | VID32 | VIE32 | VIF32 |

FIG. 2W

| | 33 | 34 | 35 | 36 |
|---|---|---|---|---|
| | biphenyl-3-carbaldehyde | biphenyl-4-carbaldehyde | ethyl acrylate (OCH₂CH₃) | CH₂O |
| VIA | VIA33 | VIA34 | VIA35 | VIA36 |
| VIB | VIB33 | VIB34 | VIB35 | VIB36 |
| VIC | VIC33 | VIC34 | VIC35 | VIC36 |
| VID | VID33 | VID34 | VID35 | VID36 |
| VIE | VIE33 | VIE34 | VIE35 | VIE36 |
| VIF | VIF33 | VIF34 | VIF35 | VIF36 |

FIG. 2X

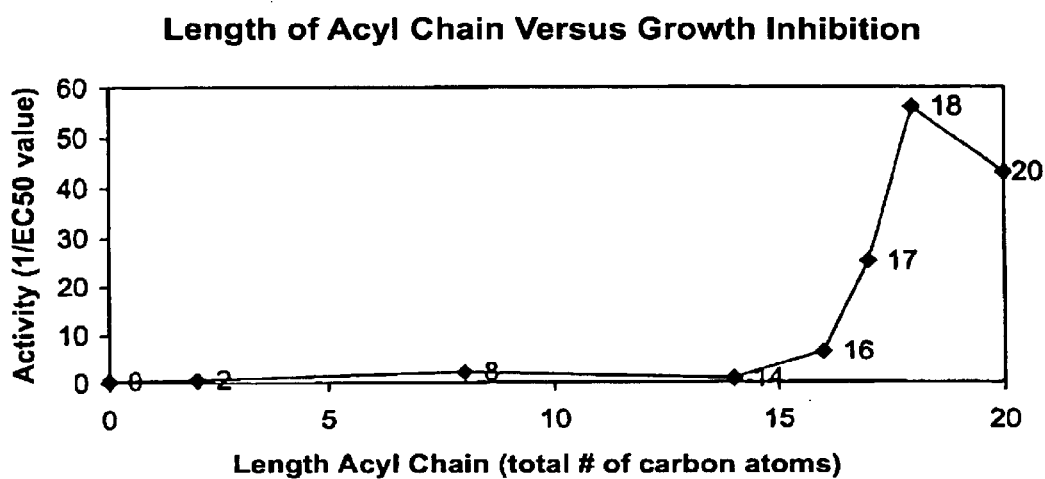
FIG. 4
Length of Acyl Chain Versus Growth Inhibition
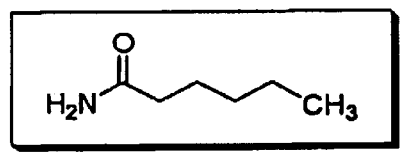
Part for LogP Calculation
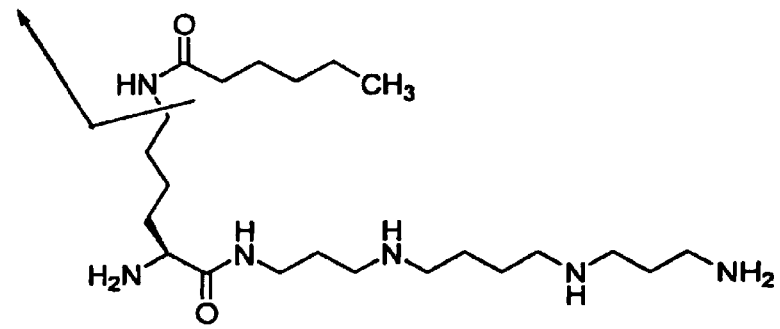
IA9 As an Example
FIG. 5

| ID | Structure |
|---|---|
| IA19 | 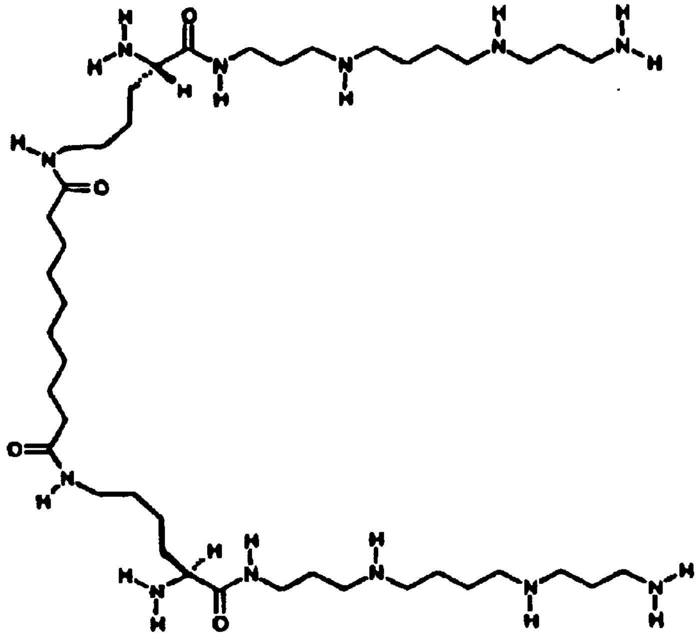 |
| IA11 | 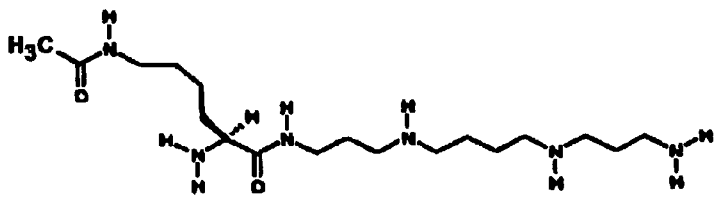 |
| IIA17 | 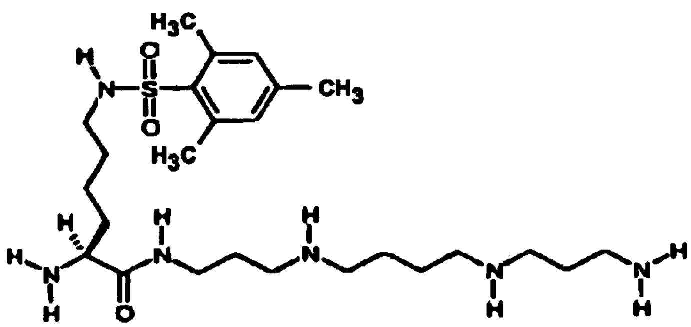 |
| IIA2 | 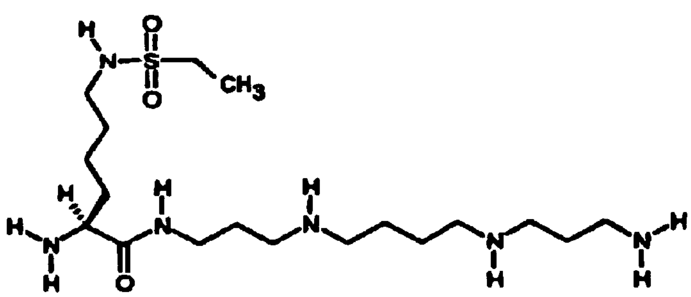 |

| ID | Structure |
|---|---|
| IID17 | 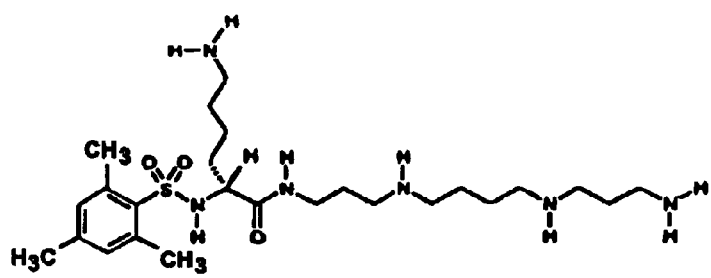 |
| IID2 | 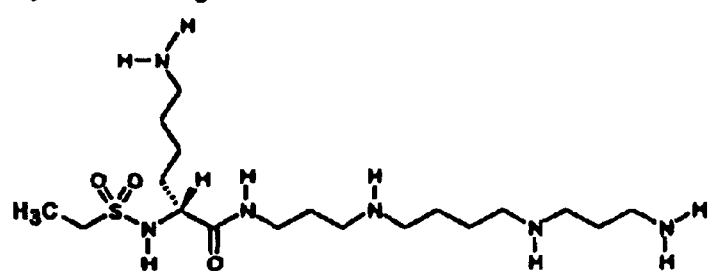 |
| ID25 | 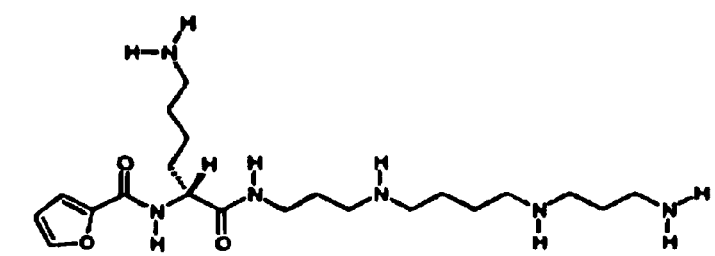 |
| ID4 | 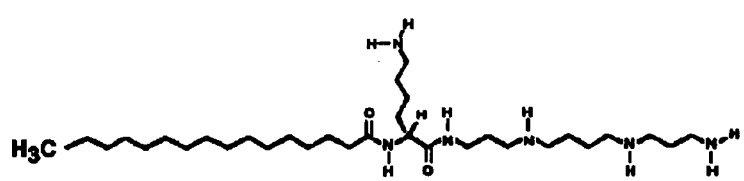 |
| IIB17 | 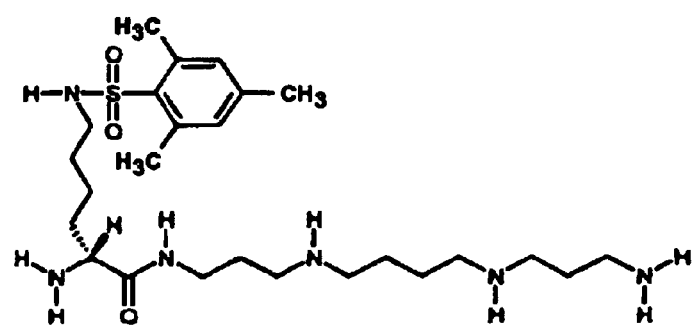 |
FIG. 12E

HYDROPHOBIC POLYAMINE ANALOGS AND METHODS FOR THEIR USE

This application is a 371 of PCT/US02/00347, filed Jan. 8, 2002; which claims benefit of Ser. No. 60/260,415, filed Jan. 8, 2001.

FIELD OF THE INVENTION

The invention in the field of chemistry and biochemistry relates to the synthesis and use of a novel class of polyamine transport inhibitor compounds. These compounds have pharmacological and/or agricultural applications as well as uses in analytical and preparative assays relating to polyamine transport. As pharmaceuticals, these compounds are used to treat disorders of undesired cell proliferation, especially in eukaryotic cells, alone or in combination with other agents such as polyamine synthesis inhibitors.

BACKGROUND OF THE INVENTION

Decades of research on the myriad of biological activities that the polyamines, putrescine, spermidine and spermine play in cellular processes have shown the profound role they play in life (Cohen, S. S., "A Guide to the Polyamines" 1998, Oxford University Press, New York). As polycations at physiological pH, they bind tightly to and strongly modulate the biological activities of all of the anionic cellular components.

Many stimuli involved in both normal and neoplastic growth activate the polyamine biosynthetic pathway. A great number of multidisciplinary studies have shown that the intracellular concentrations of the polyamines is highly regulated at many steps in their biosynthesis, catabolism and transport. The fact that cells contain such complex apparatus for the tight control of the levels of these molecules shows that only a very narrow concentration range is tolerated.

Polyamine transport into mammalian cells is energy and temperature dependent, saturable, carrier mediated and operates against a substantial concentration gradient (Seiler, N. et al. Polyamine transport in mammalian cells. *Int. J. Biochem.* 1990, 22, 211–218; Khan, N. A.; Quemener, V. et al. Characterization of polyamine transport pathways, in *Neuropharmacology of Polyamines* (Carter, C., ed.), 1994, Academic, San Diego, pp. 37–60). Ample experimental proof exists that polyamine concentration homeostasis is mediated via this transport system. Changes in the requirements for polyamines in response to growth stimulation is reflected by increases in the transport activity. Stimulation of human fibroblasts to cell proliferation by serum or epidermal growth factor was followed by an 18–100 fold increase in the uptake of putrescine (DiPasquale, A. et al. Epidermal growth factor stimulates putrescine transport and ornithine decarboxylase activity in cultures human fibroblasts. *Exp. Cell Res.* 1978, 116, 317–323; Pohjanpelto, P. Putrescine transport is greatly increased in human fibroblasts initiated to proliferate. *J. Cell Biol.* 1976, 68, 512–520). Tumors have been shown to have an increased rate of putrescine uptake (Volkow, N. et al. Labeled putrescine as a probe in brain tumors. *Science,* 1983, 221, 673–675; Moulinoux, J-P. et al. Biological significance of circulating polyamines in Oncology. *Cell. Mol. Biol.* 1991, 37, 773–783).

Inhibition of polyamine biosynthesis in cells in culture by α-difluoromethylornithine (DFMO), a well-studied mechanism-based inhibitor of ODC, causes a substantial depletion of intracellular putrescine and spermidine with resultant cell growth inhibition. Upon supplementing the culture media with exogenous polyamines this depletion causes transport activity to rise several-fold (Bogle, R. G. et al. Endothelial polyamine uptake: selective stimulation by L-arginine deprivation or polyamine depletion. *Am. J. Physiol.* 1994, 266, C776–C783; Alhonen-Hongisto, L. et al. Intracellular putrescine deprivation induces uptake of the natural polyamines and methylglyoxal bis (guanylhydrazone). *Biochem. J.* 1980, 192, 941–945). The cells then returned to their original rate of growth.

Genes for the polyamine transport protein or complex have been cloned from *Escherichia coli* and yeast (Kashiwagi, K. et al. *J. Biol. Chem.* 1990, 265, 20893–20897; Tomitori, H. et al. Identification of a gene for a polyamine transport protein in yeast. *J. Biol. Chem.* 1999, 274, 3265–3267). The genes for the mammalian transporter await identification. A subunit of the transporter from *E. coli* has been crystallized and its X-ray structure has been determined (Sugiyama, S. et al. Crystal structure of PotD, the primary receptor of the polyamine transport system in *Escherichia Coli. J. Biol. Chem.* 1996, 271, 9519–9525). This structure represents one of a few but growing number solved for spermidine-binding proteins. Since this structure was determined on a prokaryotic species its use in the design of mammalian transport inhibitors was deemed to be of limited value.

Several researchers have studied the ability of polyamine analogs to inhibit the uptake of $^3$H-spermidine into cells. Bergeron and coworkers studied the effect of addition of different alkyl group substitutions on the terminal nitrogen atoms of spermidine or spermine analogs (Bergeron, R. J. et al. Antiproliferative properties of polyamine analogs: a structure-activity study. *J. Med. Chem.* 1994, 37, 3464–3476). They showed that larger alkyl groups diminished the ability to prevent uptake of radiolabeled spermidine. They later concluded that increases in the number of methylenes between the nitrogen atoms decreased the ability to compete for $^3$H spermidine uptake (Bergeron, R. J. et al. A comparison of structure-activity relationships between spermidine and spermine antineoplastics. *J. Med. Chem.* 1997, 40, 1475–1494). They also concluded that the polyamine transport apparatus requires only three cationic centers for polyamine recognition and transport (Porter, C. W. et al. *J. Cancer Res.* 1984, 44, 126–128). Two groups have analyzed literature examples of the polyamine analogs' ability to inhibit $^3$H spermidine uptake into L1210 cells by CoMFA and QSAR methods (Li, Y. et al. Comparative molecular field analysis-based predictive model of structure-function relationships of polyamine transport inhibitors in L1210 cells. *Cancer Res.* 1997, 57, 234–239; Xia, C. Q. et al. QSAR analysis of polyamine transport inhibitors in L1210 cells. *J. Drug Target.* 1998, 6, 65–77).

A radiochemical assay is used for biochemical analysis of transport and has been used to study polyamine transport in yeast and a variety of mammalian cells (Kakinuma, Y. et al., *Biochem. Biophys. Res. Comm.* 216:985–992, 1995; Seiler, N. et al., *Int. J. Biochem. Cell Biol.* 28:843–861, 1996). See, for example Huber, M. et al. *Cancer Res.* 55:934–943, 1995.

WO 99/03823 and its corresponding U.S. patent application Ser. No. 09/341,400, filed Jul. 6, 1999, (both of which are hereby incorporated in their entireties as if fully set forth) as well as the recent publications of Burns, M. R.; Carlson, C. L.; Vanderwerf, S. M.; Ziemer, J. R.; Weeks, R. S.; Cai, F.; Webb, H. K.; Graminski, G. F. Amino acid/spermine conjugates: polyamine amides as potent spermidine uptake inhibitors. *J. Med. Chem.* 2001, 44, 3632–44 and Graminski, G. F.; Carlson, C. L.; Ziemer, J. R.; Cai, F., Vermeulen, N. M.; Vanderwerf, S. M.; Burns, M. R. Synthesis of bisspermine dimers that are potent polyamine transport inhibitors. *Bioorg. Med. Chem. Lett.* 2002, 12, 35–40 describe some extremely potent polyamine transport inhibitors.

Citation of any reference herein is not intended as an admission that any of the foregoing is pertinent prior art, nor does it constitute any admission as to the contents or date of these documents.

DISCLOSURE OF THE INVENTION

The present invention is directed to novel polyamine analogs and derivatives and methods for their use as drugs, as agricultural or as environmentally useful agents. These novel polyamine analogs and derivatives comprise a hydrophobic moiety covalently attached to a polyamine moiety. These novel PA analogs can be considered to have amphipathic character (hydrophobic as well as charged portions). The polyamine analogs and derivatives of the invention include those that may be viewed as a polyamine acylated with a hydrophobic acyl group, where acylation is by formation of either an amide or a sulfonamide linkage. While the linkage between the hydrophobic acyl group and the polyamine moiety may occur at any amine group within the polyamine, linkages to a primary amine functionality are preferred.

The analogs and derivatives of the invention are potent inhibitors of cellular polyamine transport. Without being bound by theory, they are inferred to bind to a cell's polyamine transporter apparatus with very high affinity. They may be used independently or in combination with the inhibition of cellular polyamine synthesis, even in the presence of exogenously supplied spermidine, to inhibit cell growth and proliferation.

The analogs and derivatives of the invention include those encompassed by the following formula I:

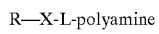

wherein R is selected from H or from the group of a straight or branched C1–50 saturated or unsaturated aliphatic, carboxyalkyl, carbalkoxyalkyl, or alkoxy; a C1–8 alicyclic; a single or multiring aryl substituted aliphatic; an aliphatic-substituted single or multiring aromatic; a single or multiring heterocyclic; a single or multiring heterocyclic aliphatic; a C1–10 alkyl; an aryl sulfonyl; or cyano;

"X" may be —CO—, —SO$_2$—, or —CH$_2$—, and

"polyamine" may be any naturally occurring, such as putrescine, spermine or spermidine, or synthetically produced polyamine.

Preferably, R is at least about C5, at least about C10, at least about C11, at least about C12, at least about C13, at least about C14, at least about C15, at least about C16, at least about C17, at least about C18, at least about C19, at least about C20, or at least about C22.

The linkage between X and the polyamine may be direct, wherein there are no atoms between X and the nitrogen of the amine group of the polyamine, or indirect, where there may be one or more atoms between X and the nitrogen of the amine group of the polyamine. The linkage between X and the polyamine may occur via any amino group within the polyamine, although a primary amino group is used in preferred embodiments of the invention.

In preferred embodiments of the invention where the linkage between X and the polyamine is indirect, the intervening one or more atoms are preferably those of an amino acid or a derivative thereof. In particularly preferred embodiments of this type, the intervening one or more atoms are those of lysine, aspartic acid, glutamic acid, ornithine, or 2,4-diaminobutyric acid. Preferred compounds of this type may be represented as

wherein R is a straight or branched C10–50 saturated or unsaturated aliphatic, carboxyalkyl, carbalkoxyalkyl, or alkoxy; a C1–8 alicyclic; a single or multiring aryl substituted or unsubstituted aliphatic; an aliphatic-substituted or unsubstituted single or multiring aromatic; a single or multiring heterocyclic; a single or multiring heterocyclic aliphatic; an aryl sulfonyl;

X is —CO—, —SO$_2$—, or —CH$_2$—; and

L is a covalent bond or a naturally occurring amino acid, ornithine, 2,4-diaminobutyric acid, or derivatives thereof.

The analogs and derivatives of the invention, may be optionally further substituted at one or more other positions of the polyamine. These include, but are not limited to, internal nitrogen and/or internal carbon atoms. In one aspect of the invention, preferred substituents are structures that increase polyamine transport inhibition, binding affinity or otherwise enhance the irreversibility of binding of the compound to a polyamine binding molecule, such as the polyamine transporter, an enzyme or DNA. Such additional substituents include the aziridine group and various other aliphatic, aromatic, mixed aliphatic-aromatic, or heterocyclic multi-ring structures. Reactive moieties which, like aziridine, bind covalently to a polyamine transporter or another polyamine binding molecule, are also within the scope of this invention. Examples of reactive groups that react with nucleophiles to form covalent bonds include chloro-, bromo- and iodoacetamides, sulfonylfluorides, esters, nitrogen mustards, etc. Such reactive moieties are used for affinity labeling in a diagnostic or research context, and may contribute to pharmacological activity in inhibiting polyamine transport or polyamine synthesis. The reactive group can be a reactive photoaffinity group such as an azido or benzophenone group. Chemical agents for photoaffinity labeling are well-known in the art (Flemming, S. A., *Tetrahedron* 1995, 51, 12479–12520).

A preferred aspect of the invention relates to a polyamine analog or derivative that is a highly specific polyamine transport inhibitor with pharmaceutical utility as an anticancer chemotherapeutic. One class of a polyamine analog or derivative of the invention that binds to a polyamine-binding site of a molecule and/or inhibits polyamine transport, is described by the following formula II:

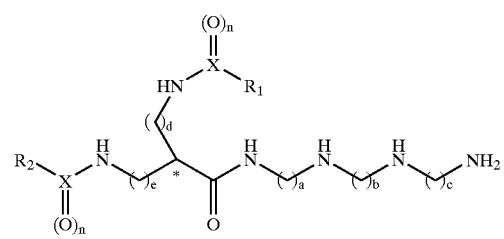

wherein a, b, and c independently range from 1 to 10; d and e independently range from 0 to 30; each X is independently either a carbon (C) or sulfur (S) atom, and R$_1$ and R$_2$ are as described below, or each of R$_1$X{O}$_n$— and R$_2$X{O}$_n$— are independently replaced by H; and * denotes a chiral carbon position. Where if X is C, then n is 1; if X is S, then n is 2; and if X is C, then the XO group may be CH$_2$ such that n is 0.

In the above formula, R$_1$ and R$_2$ are independently selected from H or from the group of a straight or branched C1–50 saturated or unsaturated aliphatic, carboxyalkyl, carbalkoxyalkyl, or alkoxy; a C1–8 alicyclic; a single or multiring aryl substituted aliphatic; an aliphatic-substituted single or multiring aromatic; a single or multiring aromatic or saturated heterocyclic; a single or multiring heterocyclic aliphatic; a C1–10 alkyl; an aryl sulfonyl; or cyano.

Examples of heterocyclic rings as used herein include, but are not limited to, pyrrole, furan, thiophene, imidazole, oxazole, thiazole, pyrazole, 3-pyrroline, pyrrolidine, pyridine, pyrimidine, purine, quinoline, isoquinoline, and carbazole.

All of the above described aliphatic, carboxyalkyl, carbalkoxyalkyl, alkoxy, alicyclic, aryl, aromatic, and heterocyclic moieties may, of course, also be optionally substituted with 1–3 substituents independently selected from halo (fluoro, chloro, bromo or iodo), lower alkyl (1–6C) and lower alkoxy (1–6C).

As used herein, carboxyalkyl refers to the substituent —R'—COOH wherein R' is alkylene; and carbalkoxyalkyl refers to —R'—COOR wherein R' and R are alkylene and alkyl respectively. In preferred embodiments, alkyl refers to a saturated straight- or branched-chain hydrocarbyl radical of 1–6 carbon atoms such as methyl, ethyl, n-propyl, isopropyl, n-butyl, t-butyl, n-pentyl, 2-methylpentyl, n-hexyl, and so forth. Alkylene is the same as alkyl except that the group is divalent. Aryl or alkyl sulfonyl moieties have the formula —SO$_2$R, and alkoxy moieties have the formula —O—R, wherein R is alkyl, as defined above, or is aryl wherein aryl is phenyl, optionally substituted with 1–3 substituents independently selected from halo (fluoro, chloro, bromo or iodo), lower alkyl (1–6C) and lower alkoxy (1–6C).

A preferred group of compounds encompassed by the above is where d is 4 and e is 0.

An additional class of a polyamine analog or derivative of the invention that binds to a polyamine-binding site of a molecule and/or inhibits polyamine transport, is described by the following formula III:

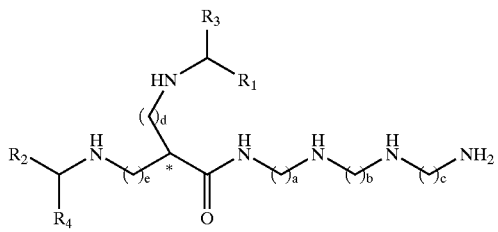

wherein a, b, and c independently range from 1 to 10 and d and e independently range from 0 to 30. $R_1$ and $R_2$ are defined as above for formula II and $R_3$ and $R_4$ are independently selected from organic substituents including —CH$_3$ and as defined above for $R_1$ and $R_2$ in formula II above. This grouping of analogs is produced by reductive amination of the free amino precursor with a ketone. Some members of this group of analogs are shown in Series V (see FIG. 2).

In one preferred embodiment of the invention, $R_1$ and $R_2$ are identical and as described for formula II. Positions $R_3$ and $R_4$ may also be identical, and all of $R_1$ through $R_4$ may also be identical. Additionally, each of positions $R_1$, $R_2$, $R_3$ and $R_4$ in formula III may also be independently H.

In an additional aspect of the invention the proximal and/or the distal amino group relative to the polyamine (such as spermine) can be di-alkylated to form tertiary amines. These materials can be synthesized by reductive amination with a large excess of the carbonyl component. Additionally, these materials may be produced by a conjugate addition of the amine precursor to an α,β-unsaturated carbonyl or α,β-unsaturated nitrile. Each of $R_1$, $R_2$, $R_3$ and $R_4$ can be independently varied and are as defined as above for formula III. Each of $R_1$, $R_2$, $R_3$ and $R_4$ may also be independently H. The values of a, b, c, d and e are as described above for formula III. This aspect of the invention is depicted in the following formula IV:

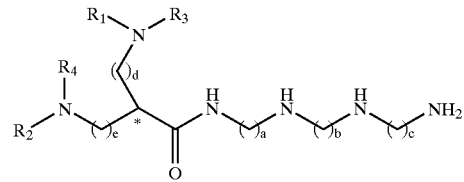

In a further aspect of the invention, compounds which lack the proximal or distal amino group on the acyl portion of the molecule are also provided. These are represented by formula V:

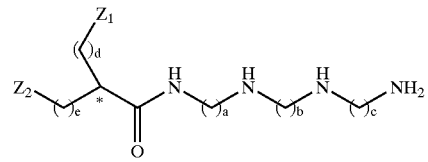

where $Z_1$ is NR$_1$R$_3$ and $Z_2$ is selected from —R$_1$, —CHR$_1$R$_2$ or —CR$_1$R$_2$R$_3$ (wherein R$_1$, R$_2$, and R$_3$ are as defined above for formula III) or $Z_2$ is NR$_2$R$_4$ and $Z_1$ is selected from —R$_1$, —CHR$_1$R$_2$ or —CR$_1$R$_2$R$_3$ (wherein R$_1$, R$_2$, and R$_3$ are as defined above for formula III) Values for a, b, and c independently range from 1 to 10; d and e independently range from 0 to 30. Compounds encompassed by formula V may be prepared by first coupling amino acid derivatives (modified to contain the non-amine containing Z group) to a polyamine followed by appropriate derivatization of the amine containing Z group. Chemistries for such reactions are known in the art and disclosed herein.

In preferred embodiments of the invention, positions $R_1$, $R_2$, $R_3$ and $R_4$ of all the formulas set forth above are independently selected from the following, where each of g, h, i, j, and k are independently selected from 0 to 15:

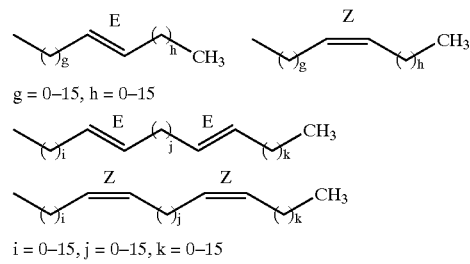

g = 0–15, h = 0–15 i = 0–15, j = 0–15, k = 0–15 wherein E refers to "entgegen" and Z refers to "zusammen".

The present invention includes the free base or acid forms, as well as salts thereof, of the polyamine analogs and derivatives described by the above formulas. The invention also includes the optical isomers of the above described analogs and derivatives, especially those resulting from the chiral center indicated above with a *. In a further embodiment of the invention, mixtures of enantiomers and/or diastereoisomers, resulting from a single preparative step, combination, or interconversion are encompassed.

The invention also provides prodrug forms of the above described analogs and derivatives, wherein the prodrug is metabolized in vivo to produce an analog or derivative as set forth above. Indeed, some of the above described analogs or derivatives may be a prodrug for another analog or derivative.

In another aspect of the invention, compositions containing the above described analogs and derivatives are provided. Preferably, the compositions are formulated to be suitable for pharmaceutical or agricultural use by the inclusion of appropriate carriers or excipients.

In a further aspect of the invention, methods for the use of the above described analogs and derivatives, as well as compositions, are provided. These methods include uses of the invention's polyamine compounds to inhibit polyamine transport, as well as treat human and agricultural diseases and conditions. Examples of human diseases and conditions include, but are not limited to, cancer, osteoporosis, asthma, autoimmune diseases, rheumatoid arthritis, systemic lupus erythematosus, Type I insulin-dependent diabetes, tissue transplantation, African sleeping sickness, psoriasis, restenosis, inhibition of unwanted hair growth as cosmetic suppression, hyperparathyroidism, inflammation, treatment of peptic ulcer, glaucoma, Alzheimer's disease, suppression of atrial tachycardias, stimulation or inhibition of intestinal motility, Crohn's disease and other inflammatory bowel diseases, high blood pressure (vasodilation), stroke, epilepsy, anxiety, neurodegenerative diseases, hyperalgesic states, protection against hearing loss (especially cancer chemotherapy induced hearing loss), and pharmacological manipulation of cocaine reinforcement and craving in treating cocaine addiction and overdose and other fungal bacterial, viral, and parasitic diseases. These compounds also find use as agents for use in the trans-cellular delivery of nucleic acids used in anti-sense DNA therapies for numerous disease states. The invention's polyamine compounds may be utilized as, but not limited to being, a soil additive or conditioner in agricultural applications.

BRIEF DESCRIPTION OF THE DRAWINGS

FIG. 4 shows the relationship between the length of the hydrocarbon substituent at the ε-position of the L-lysine analogs and the resulting activity as polyamine transport inhibitors as defined by EC$_{50}$ (see Example IV).

FIG. 5 representatively shows the portion of compounds for calculation of logP values.

FIGS. 12A–12K show the structures of exemplary polyamine analogs and derivatives of the present invention.

MODES OF CARRYING OUT THE INVENTION

Figure 1A:
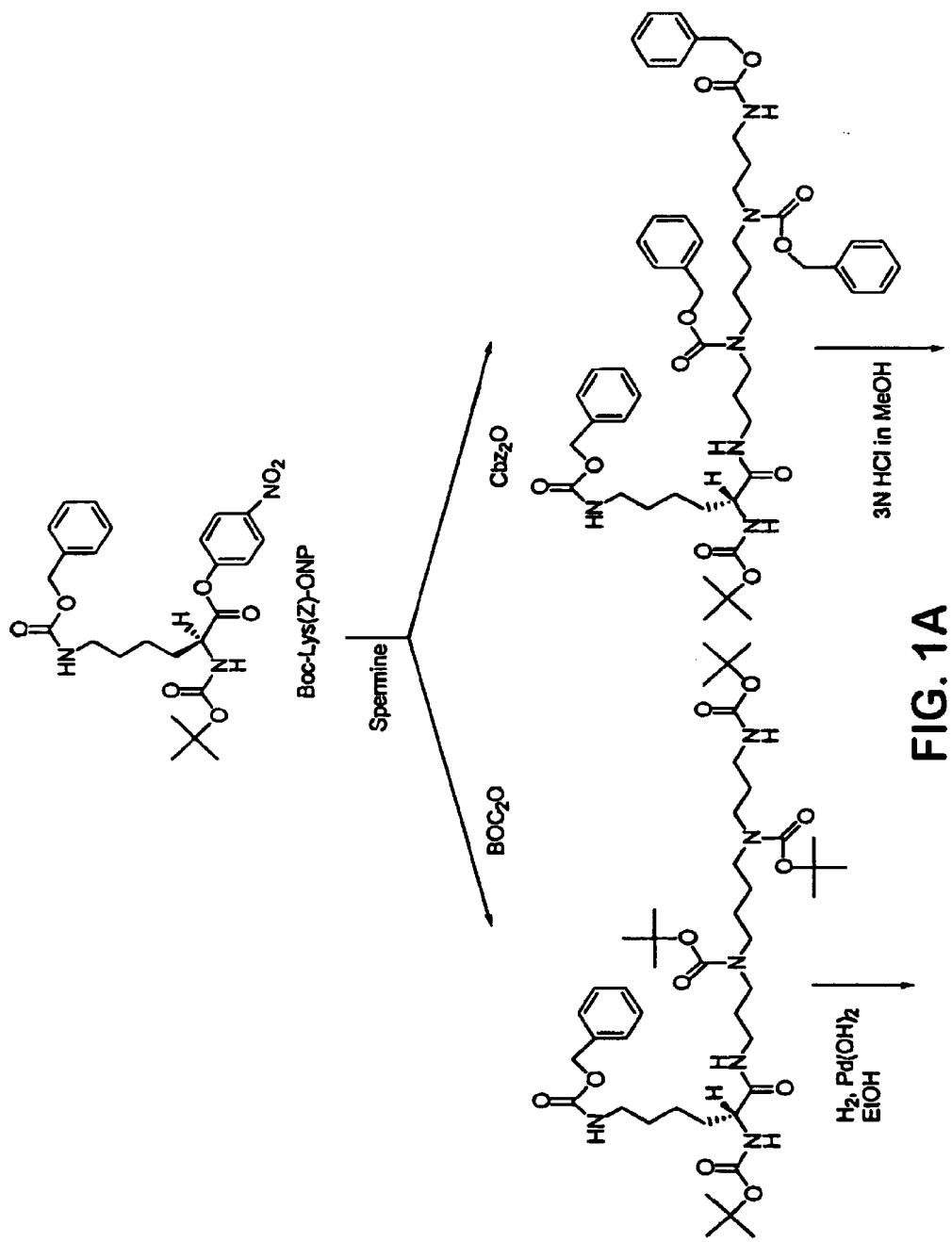
FIGS. 1A and 1B show Scheme 1, a pathway for the synthesis of selectively acylated lysine-spermine derivatives. The pathway may be readily adapted for the synthesis of other polyamine derivatives by the use of an analogous protected "NH—X—COO" starting material (wherein X is CH—(CH$_2$)$_d$—NH—COO—CH$_2$—Ph, wherein d is as described above and "Ph" is phenyl) and/or the use of any primary polyamine, including spermine.

The present inventors have designed novel polyamine analogs and derivatives for the inhibition of polyamine transport and other uses. These analogs and derivatives are inferred to bind polyamine transporters with high affinity and inhibit polyamine transport, either competitively or non-competitively. Thus these compounds can alter polyamine metabolism in cells by reducing or preventing polyamine uptake.

In particularly preferred embodiments of the invention, one or more polyamine analogs and derivatives are used in combination with polyamine synthesis inhibitors to inhibit cell growth and proliferation. As such, they are useful as drugs in a number of diseases, particularly cancer and other conditions involving cellular proliferation, including, but not limited to, inflammatory diseases or conditions where components of the immune system undergo undesired proliferation. Non-limiting examples include asthma, autoimmune diseases, rheumatoid arthritis, systemic lupus erythematosus, Type I insulin dependent diabetes, psoriasis, restenosis, inhibition of unwanted proliferation of hair on skin, tissue transplantation, African sleeping sickness, osteoporosis, hyperparathyroidism, treatment of peptic ulcer, glaucoma, Alzheimer's disease, suppression of atrial tachycardias, stimulation or inhibition of intestinal motility, Crohn's disease and other inflammatory bowel diseases, high blood pressure (vasodilation), stroke, epilepsy, anxiety, neurodegenerative diseases, hyperalgesic states, the protection of hair cells from chemotherapy induced loss of hearing, and pharmacological manipulation of cocaine reinforcement and craving in treating cocaine addiction and overdose, and other fungal, bacterial, viral, and parasitic diseases.

As used herein, the term "polyamine" includes putrescine, spermine or spermidine, as well as longer linear polyamines, branched polyamines, and the like, which may have between 2 and about 10 nitrogens. Also included in this definition are polyamine derivatives or analogs comprising a basic polyamine chain with any of a number of functional groups bound to a C atom or a terminal or internal N atom. For modification at a primary amino group, a polyamine must, of course, contain such a group.

Polyamine "analogs" and/or "derivatives" generally refer to any modified polyamine molecule disclosed or described herein. These molecules are generally modifications of existing polyamines, whether naturally occurring or synthetically produced, and may also be referred to as "polyamine agents", "PA" or "agents" of the invention. Preferred PAs bind and/or inhibit cellular polyamine transport, and as such may also be referred to as "transport binding molecules" or "polyamine transport inhibitors". The scope of this definition includes any modification to produce a PA from an existing polyamine or the isolation of a structurally identical PA from a naturally occurring source. Preferably, the modification is the addition of one or more chemical moieties to the polyamine.

A PA that is an "inhibitor" polyamine analog or derivative (a) binds to polyamine transporters better than a native polyamine and/or (b) by some means blocks the uptake of a polyamine into a cell or a subcellular polyamine transporter preparation. The invention includes PAs that efficiently inhibit polyamine transporters in different eukaryotic cell types as well as inhibit cellular growth and proliferation when used in combination with a polyamine synthesis inhibitor.

The PAs of the invention generally have an acylated primary amine functionality and are expected to bind to a cell's polyamine transporter apparatus with a very high affinity. Measurements of $K_i$ were determined by using an assay that shows the inhibition of polyamine uptake, such as uptake of $^3$H-spermidine.

The PAs were also analyzed with a secondary assay to show inhibition of cellular polyamine uptake based on a measurement of cellular growth inhibition in combination with a potent inhibitor of polyamine biosynthesis. This assay was conducted in the presence of polyamines, such as spermidine, to determine a PA's ability to prevent the uptake of polyamines thereby overcoming the polyamine biosynthesis inhibition with DFMO (difluoromethylornithine). Due to the trend that polyamine mono-anides give high potency in both of these assays, it has been inferred, without limiting the invention thereto, that there is a site on the transporter protein for tight binding of the inhibitor's amide functionality.

Preferred embodiments of these PAs are the result of acylation at a polyamine molecule with two or more primary amine groups. The linkage between the acyl group and the primary amine group is preferably an amide linkage (indicated below as the bond between "CO" and "NH") and results in a molecule with the following general formula.

rest of acyl group-CO—NH-rest of polyamine

As noted above, other linkages, whether direct or indirect, may also be used. The "polyamine" in the above formula may be any polyamine with at least one primary amine group, but more preferably with two or more primary groups, for linkage to the acyl group.

One preferred class of acyl groups for inclusion in the above formula contains two primary amines for further acylation. The resultant class of PAs may be described by the following formula (formula II).

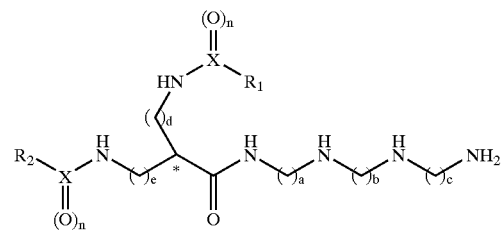

as defined above. Non-limiting examples of alkyl moieties as present in these compounds include straight or branched chains of at least about 8 carbon atoms for increased hydrophobicity (or lipophilicity), such as at least about 10, at least about 12, at least about 14, at least about 16, at least about 18, at least about 20, at least about 22, at least about 24, at least about 26, at least about 28, and at least about 30. In yet another set of preferred embodiments, the chain is of at least about 19, 21, 23, 25, or 27 carbon atoms, with at least about 20 to at least about 24 or 26 as even more preferred.

A particularly preferred group of PAs encompassed by the above formula is where d is 4 and e is 0, although generally excluded from this group are PAs where $R_2X\{O\}_n$— is an H and $R_1X\{O\}_n$— is $R_1SO_2$— wherein $R_1$ is a thiophene moiety linked to the S atom via the 2 position, and substituted at the 5 position, of the thiophene. Preferably excluded are such PAs wherein the substitution at the 5 position includes an amide linkage. Also preferably excluded are such PAs wherein the amide linkage is attached to a chlorinated aromatic group, such as the compound identified as ORI 1340 in U.S. patent application Ser. No. 09/396,523, filed Sep. 15, 1999.

Other classes of PAs as encompassed by the invention are set forth as formulas I, III, IV, and V as described above. In all of the formulas of the invention, the term "single or multiring alicyclic" includes adamantyl type structures. Moreover, the term "substituted" used in conjunction with the description of any chemical moiety for a formula of the invention includes the attachment of the moiety to the rest of the formula by way of the "substitution". The term also indicates that "unsubstituted" forms of the described chemical moiety is also within the scope of the invention.

By analyzing the relationship between a polyamine analog's structure and its ability to act as a polyamine transport inhibitor, it was discovered that increases in the lipophilic character of the hydrophobic substituent on the polyamine may increase transport inhibition. While the nature of the interaction between a lipophilic polyamine analog and the polyamine transport apparatus remains unclear at this time, the invention includes, but is not limited to, situations where the hydrophobic (lipophilic) moiety may serve as an anchor to some hydrophobic pocket on the transporter or in a region nearby. This may result in the interaction of the polyamine portion of the analog with the polyamine transporter.

There are a number of ways one might analyze the hydrophobic character of compounds described in the present invention. The following two scales describe ways to measure relative degrees of lipophilicity.

The logP coefficient is the logarithm of the ratio of distribution of a compound in a mixture of 1-octanol and $H_2O$. Compounds with logP values greater than 1 are considered lipophilic (greater solubility in 1-octanol versus $H_2O$). The presence of ionizable groups in the compound has a dramatic effect on this parameter. Ionization will greatly increase a compound's $H_2O$ solubility. For this reason, a compound's ionization potential must be taken into consideration when correlating lipophilicity with activity. One can use a variety of computerized protocols to perform calculated estimates of the logP value. One such computer program is ChemDraw Pro Version 5.0 from Cambridge-SoftCorporation. One of the several methods that this program uses to calculate the logP coefficient is through Crippen's fragmentation method (Crippen et. al., *J. Chem. Inf. Comput. Sci.* 1987, 27, 21). The present invention used this method to calculate logP values for fragments of the described molecules. These fragments were generated in the fashion depicted in FIG. 5. The results of these calculations are provided in Table 1 for the D-stereoisomers of the ε-acyl substituted Lys-spm conjugates (FIG. 2, Series I) and in Table 2 for the D-stereoisomers of the ε-alkyl substituted Lys-spm conjugates (FIG. 2, Series IV and V).

TABLE 1

Figure 2A:
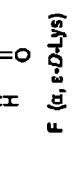
FIGS. 2A–2X illustrate exemplary polyamine structures encompassed by the present invention. They have been divided into Series I–VI based upon the character of the chemical moiety attached to a spermine backbone to produce exemplary analogs and derivatives of the invention. Other polyamines may also be used as the backbone. The structures depicted in the first, left-most column of each table represent the specific chemical starting materials utilized in the synthesis of individual polyamine structures. The synthetic steps used result in the end products that are carboxamides from a reaction between an acyl chloride and an amine (series I), sulfonamides from the reaction between a sulfonyl chloride and an amine (series II), carboxamides from the reaction of a DCC, HBTU or PyBOP activated carboxylic acid and an amine (series III), alkylated secondary amines from the reductive amination of the amine with an aldehyde (series IV), alkylated secondary amines with α-alkyl substituents from the reductive amination of the free amino precursor with a ketone (Series V) and di-alkylated tertiary amine products by reductive amination with a large excess of a carbonyl containing (e.g. aldehyde or ketone) component (Series VI). Additionally the Series VI compounds may also be produced by a conjugate addition of the amine precursor to an α,β-unsaturated carbonyl or α,β-unsaturated nitrile. Columns E and F are directed to doubly derivatized forms of the base chemical structure.
Figure 2H:
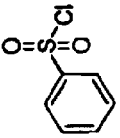
Figure 2P:
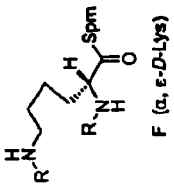
Figure 3A:
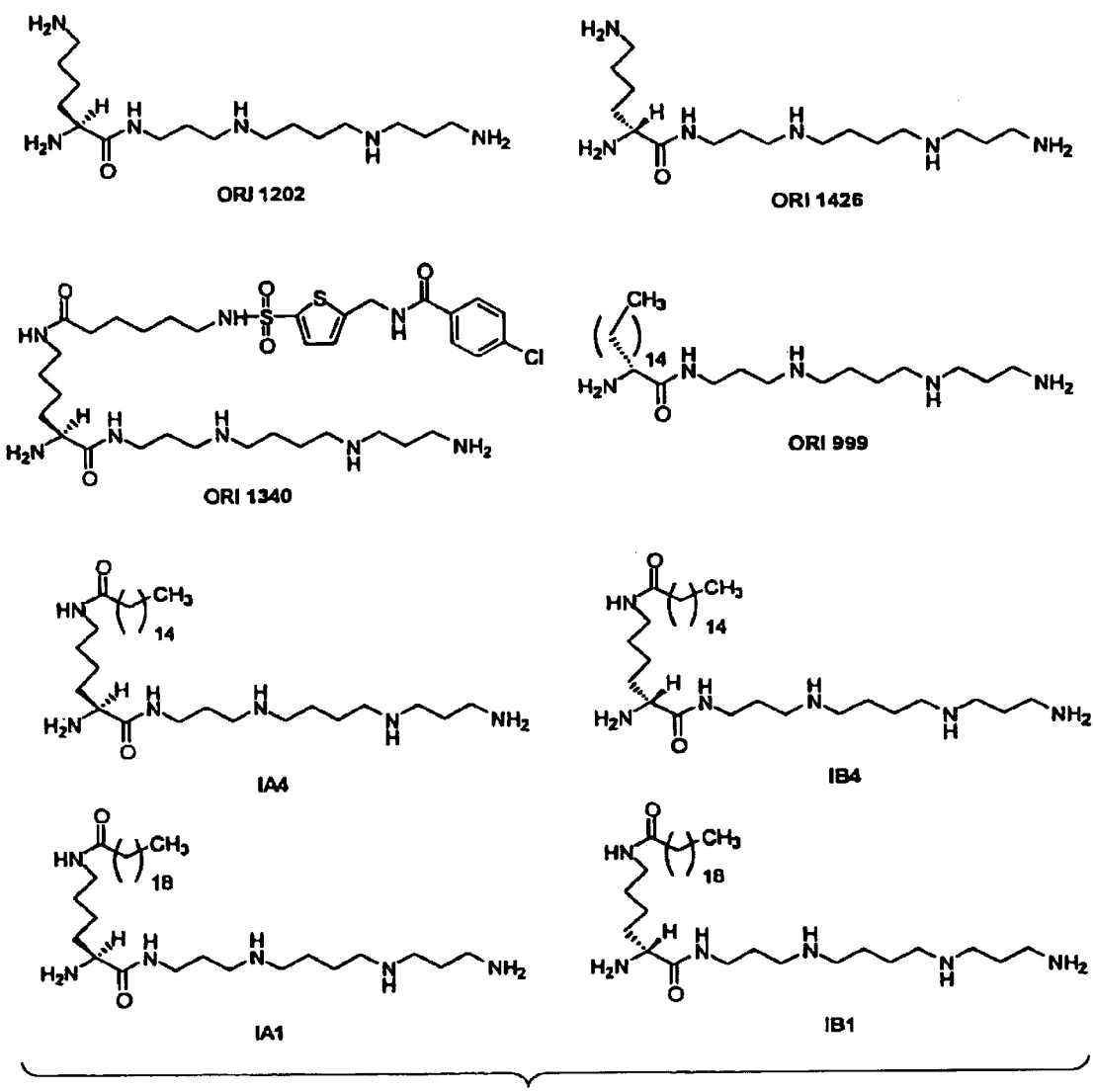
FIGS. 3A and 3B show representative structures of polyamine analogs relating to the present invention.
Figure 3B:
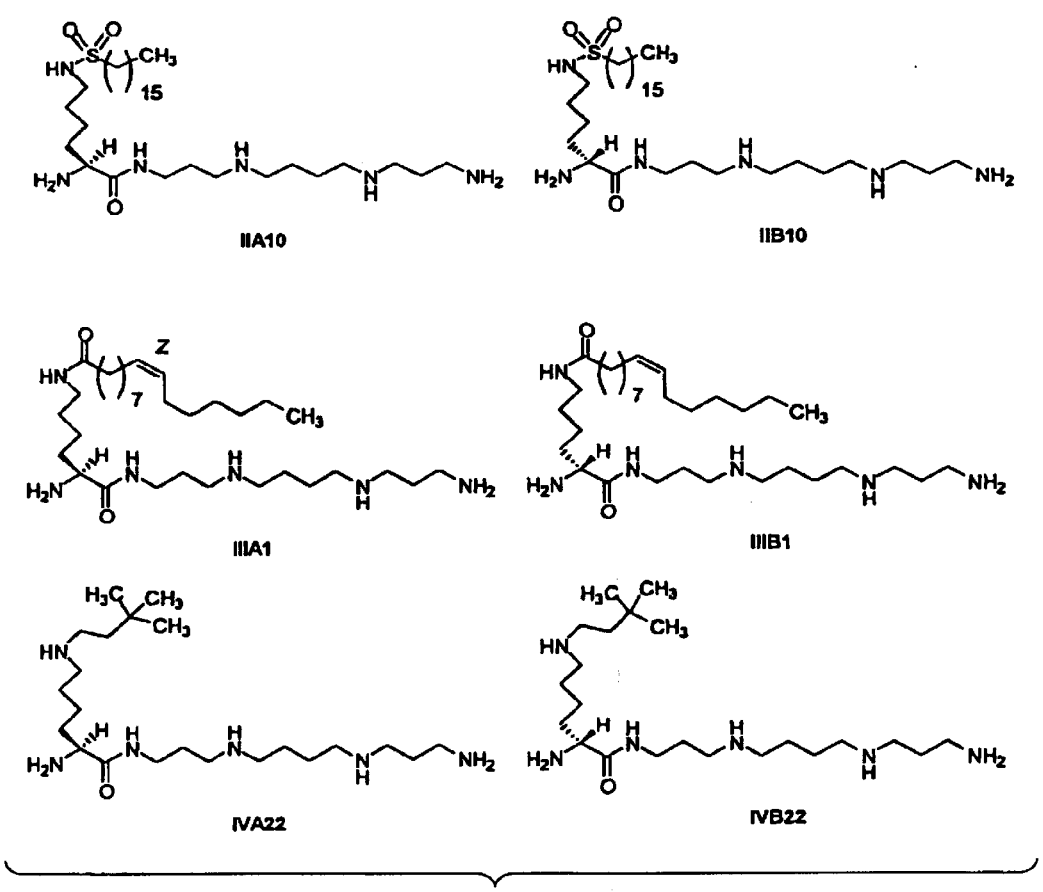

Chemical structure (with ID relative to FIG. 2), logP Calculations, HPLC data and average $EC_{50}$ values for D-stereoisomerS of ε-acyl-substituted spermine based analogs (FIG. 2, Series I). Compound 1426 and one Series V compound are included for comparison.

| ID | Structure | LogP | Ret Time-Std | Ave $EC_{50}$ value |
|---|---|---|---|---|
| IB38 | 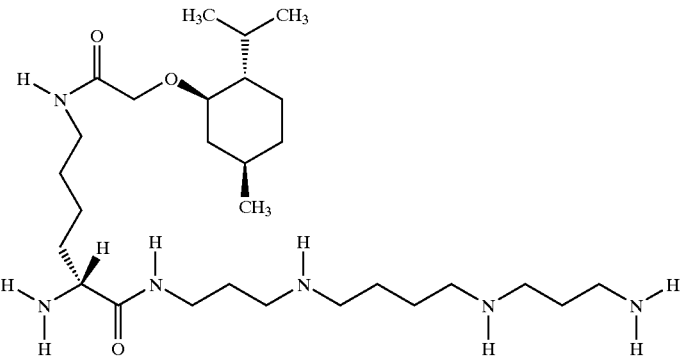 | 1.73 | 9.63 | 13 |
| IB37 | 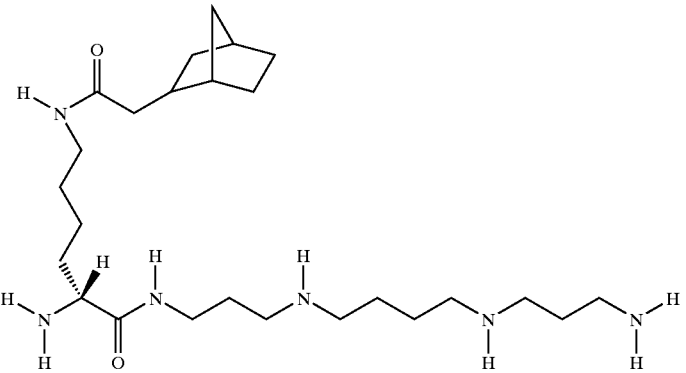 | 1.03 | 6.33 | 41 |
| IB2 | 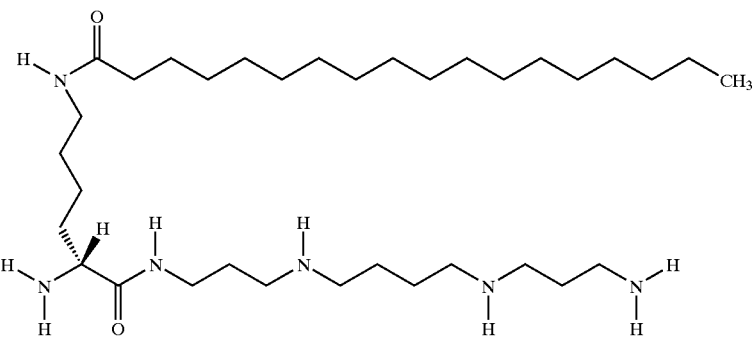 | 6.59 | 21.1 | 0.083 |

TABLE 1-continued

Chemical structure (with ID relative to FIG. 2), logP Calculations, HPLC data and average $EC_{50}$ values for D-stereoisomerS of ε-acyl-substituted spermine based analogs (FIG. 2, Series I). Compound 1426 and one Series V compound are included for comparison.

| ID | Structure | LogP | Ret Time-Std | Ave $EC_{50}$ value |
|---|---|---|---|---|
| IB4 | 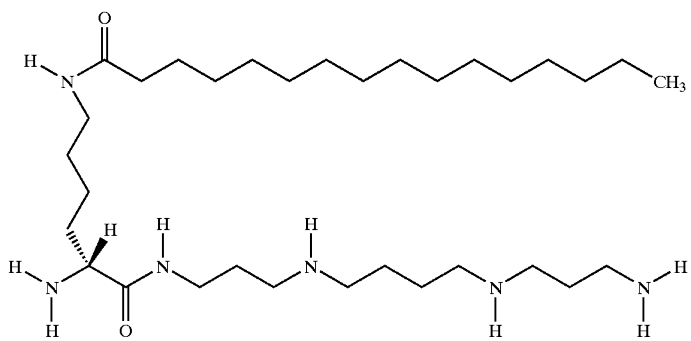 | 5.68 | 15.82 | 0.084 |
| IB8 | 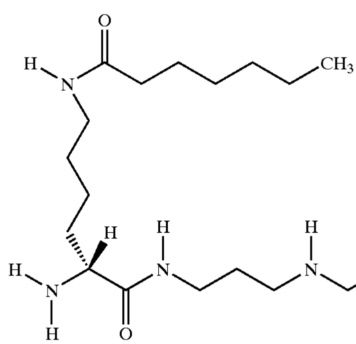 | 1.57 | 6.07 | 3.5 |
| IB26 | 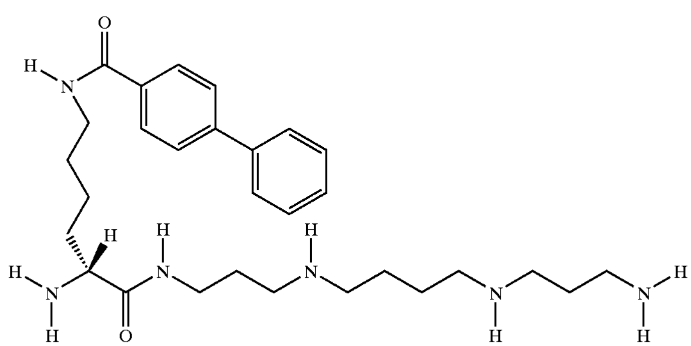 | 2.01 | 6.34 | 1.1 |
| IB36 | 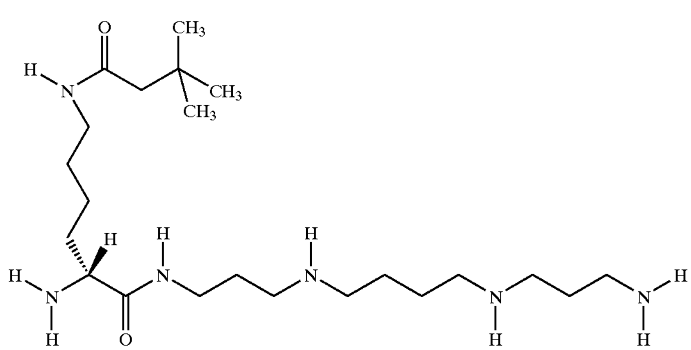 | 1.21 | 4.91 | 27 |

TABLE 1-continued

Chemical structure (with ID relative to FIG. 2), logP Calculations, HPLC data and average $EC_{50}$ values for D-stereoisomerS of ε-acyl-substituted spermine based analogs (FIG. 2, Series I). Compound 1426 and one Series V compound are included for comparison.

| ID | Structure | LogP | Ret Time-Std | Ave $EC_{50}$ value |
|---|---|---|---|---|
| IB34 | 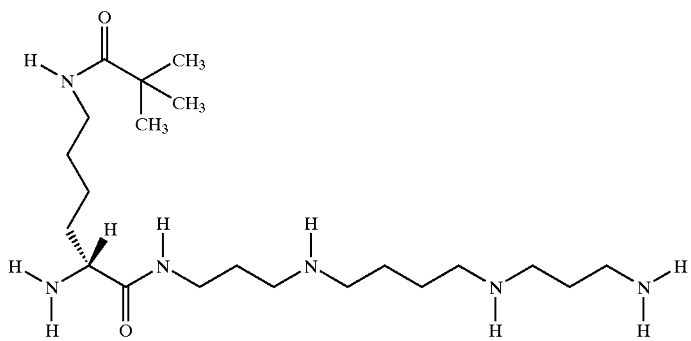 | 0.75 | 4.6 | 8.5 |
| IB6 | 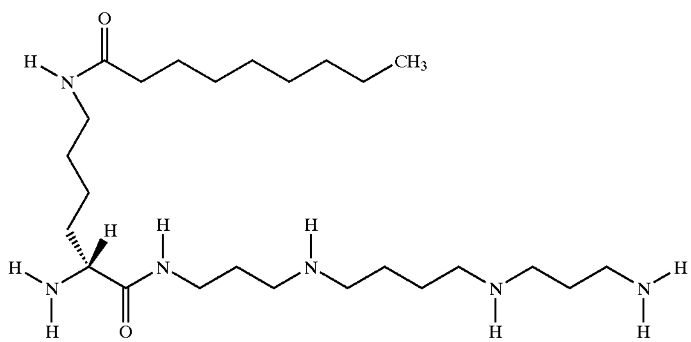 | 2.58 | 10.48 | 2.2 |
| IB7 | 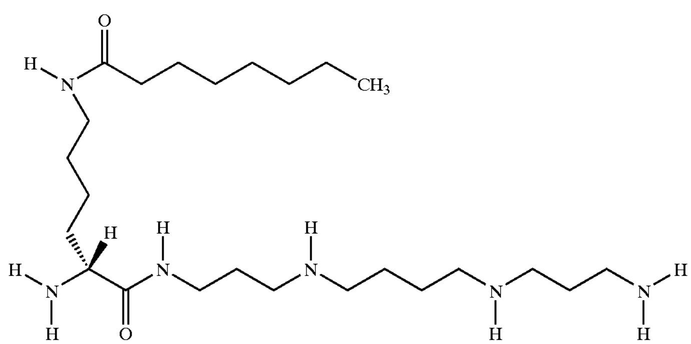 | 2.03 | 6.83 | 13 |
| IB9 | 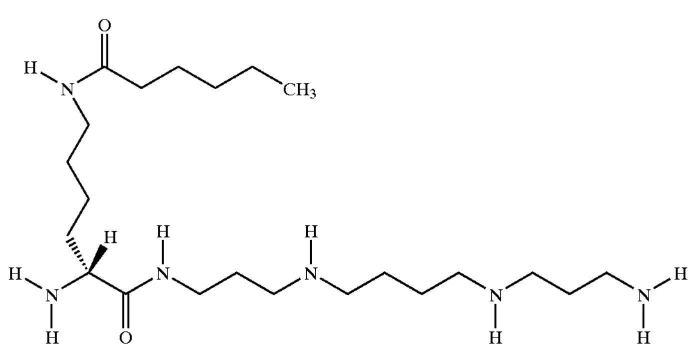 | 1.12 | 5.16 | 12 |

TABLE 1-continued

Chemical structure (with ID relative to FIG. 2), logP Calculations, HPLC data and average $EC_{50}$ values for
D-stereoisomerS of ε-acyl-substituted spermine based analogs (FIG. 2, Series I).
Compound 1426 and one Series V compound are included for comparison.

| ID | Structure | LogP | Ret Time-Std | Ave $EC_{50}$ value |
|---|---|---|---|---|
| IB33 | 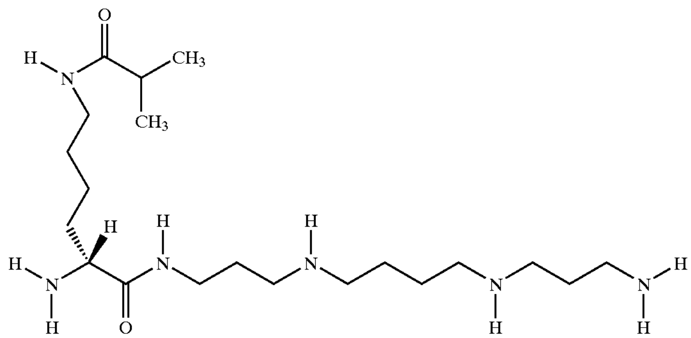 | −0.05 | 3.56 | 8.4 |
| IB10 | 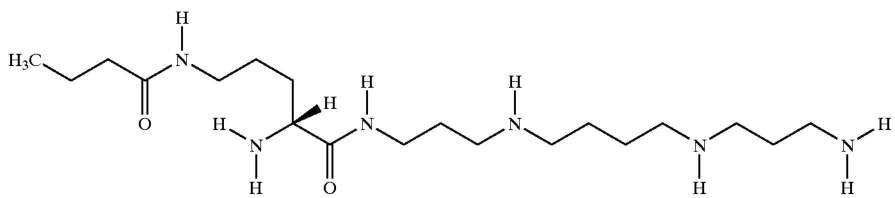 | 0.2 | 3.46 | 12 |
| IB32 | 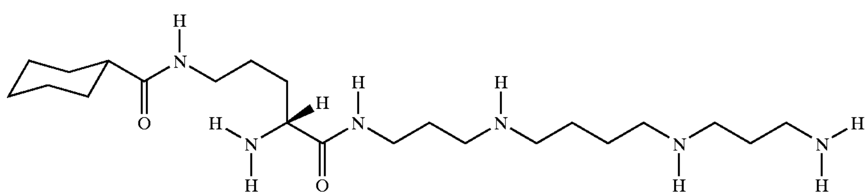 | 0.97 | 5.29 | 3.6 |
| IB30 | 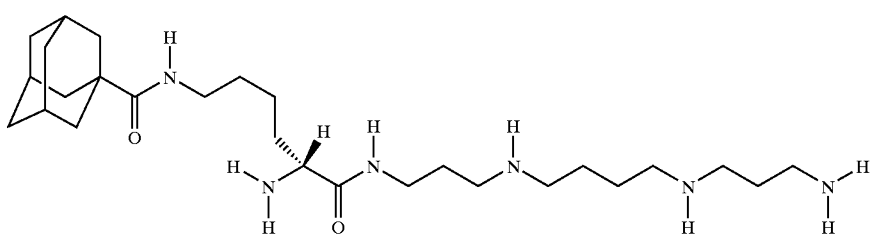 | 1.68 | 7.4 | 2 |
| IB29 | 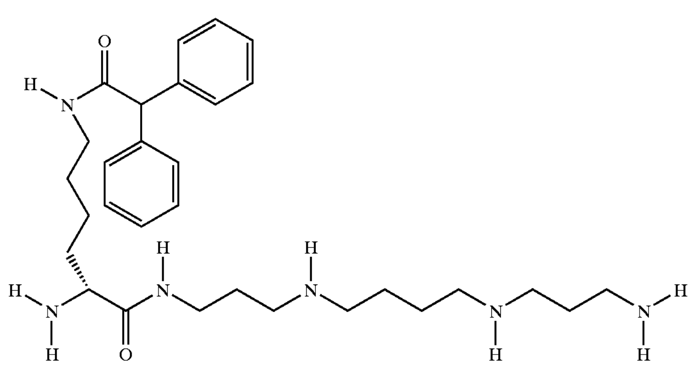 | 1.99 | 6.08 | 2.1 |

TABLE 1-continued

Chemical structure (with ID relative to FIG. 2), logP Calculations, HPLC data and average $EC_{50}$ values for D-stereoisomerS of ε-acyl-substituted spermine based analogs (FIG. 2, Series I). Compound 1426 and one Series V compound are included for comparison.

| ID | Structure | LogP | Ret Time-Std | Ave $EC_{50}$ value |
|---|---|---|---|---|
| IB25 | *(structure: furan-2-carboxamide ε-acyl spermine analog)* | −0.44 | No Data | 10 |
| IB24 | *(structure: benzamide ε-acyl spermine analog)* | 0.58 | 4.23 | 30 |
| VA-21 | *(structure: N-diisobutyl spermine analog)* | 1.04 | 10.11 | 0.65 |
| 1426 | *(structure: lysine-spermine conjugate)* | Not calc'd | 6.68 | 3.7 |

TABLE 1-continued

Chemical structure (with ID relative to FIG. 2), logP Calculations, HPLC data and average $EC_{50}$ values for D-stereoisomerS of ε-acyl-substituted spermine based analogs (FIG. 2, Series I). Compound 1426 and one Series V compound are included for comparison.

| ID | Structure | LogP | Ret Time-Std | Ave $EC_{50}$ value |
|---|---|---|---|---|
| IA4 | 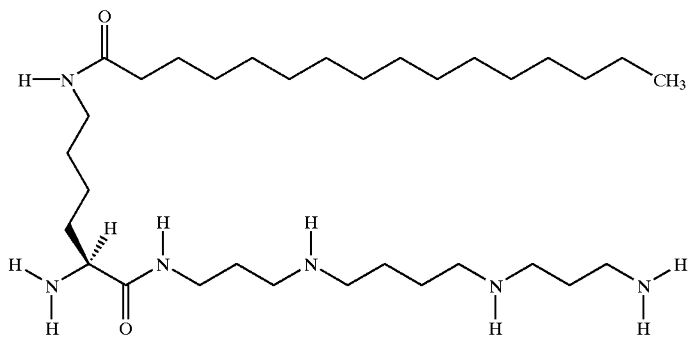 | 5.68 | 15.79 | 0.13 |

Preferred PAs of the invention with respect to Series I type compounds are those with low $EC_{50}$ values, such as those with below about 5, about 6, about 7, about 8, about 9, about 10, about 15, about 20 or about 25 minute HPLC retention times.

TABLE 2

Chemical structure (with ID relative to FIG. 2), calculated logP value, HPLC retention time, and average $EC_{50}$ value for ε-alkylated spermine based analogs (FIG. 2, Series IV and V). Compound 1426 and one Series I compound are included for comparison.

| ID | Structure | LogP | Ret Time-Std | Ave $EC_{50}$ value |
|---|---|---|---|---|
| VB28 | 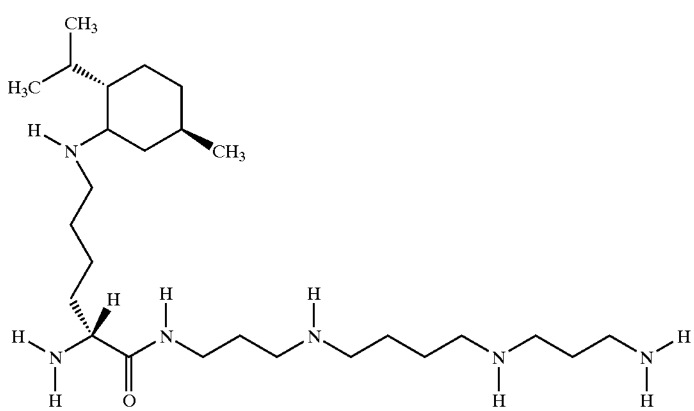 | 2.01 | 13.89 | 1.45 |
| IVB28 | 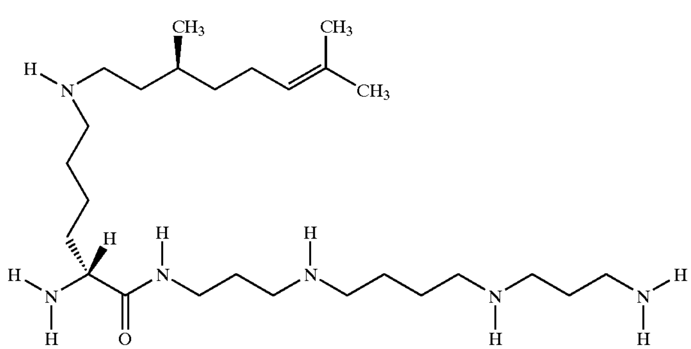 | 2.21 | 9.4 | 12.8 |

TABLE 2-continued

Chemical structure (with ID relative to FIG. 2), calculated logP value, HPLC retention time, and average EC$_{50}$ value for ε-alkylated spermine based analogs (FIG. 2, Series IV and V). Compound 1426 and one Series I compound are included for comparison.

| ID | Structure | LogP | Ret Time-Std | Ave EC$_{50}$ value |
|---|---|---|---|---|
| VA22 | 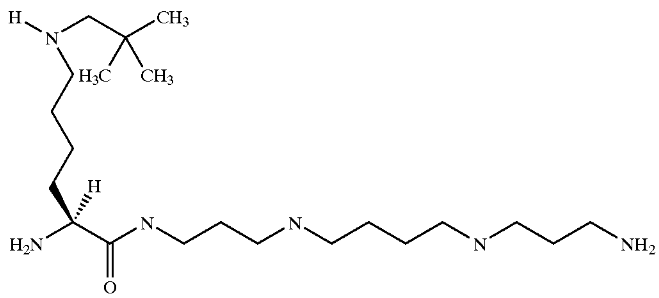 | 1.84 | 10 | 2.42 |
| VA27 | 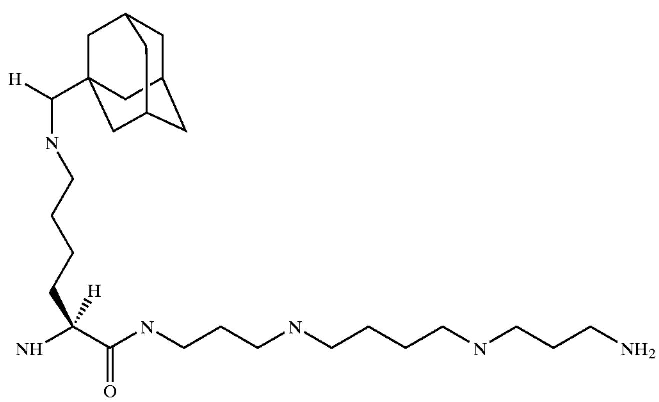 | 2.31 | 12.71 | 26.8 |
| VA26 | 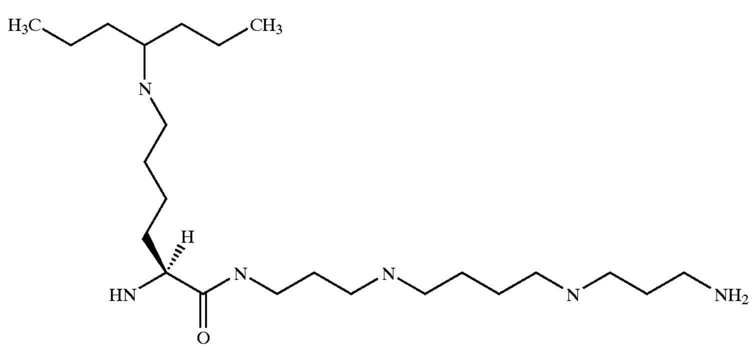 | 1.74 | 10.84 | 4.14 |
| IVB23 | 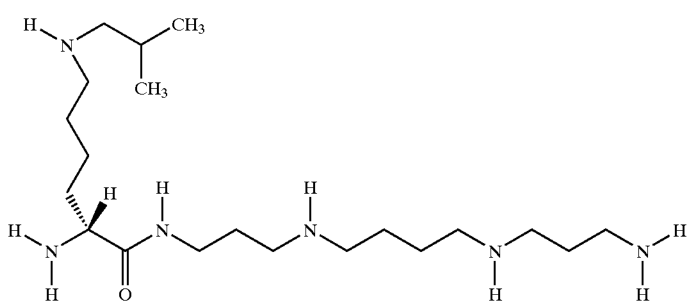 | 0.66 | 9.05 | 1.79 |

TABLE 2-continued

Chemical structure (with ID relative to FIG. 2), calculated logP value, HPLC retention time, and average EC$_{50}$ value for ε-alkylated spermine based analogs (FIG. 2, Series IV and V). Compound 1426 and one Series I compound are included for comparison.

| ID | Structure | LogP | Ret Time-Std | Ave EC$_{50}$ value |
|---|---|---|---|---|
| IVB3 | 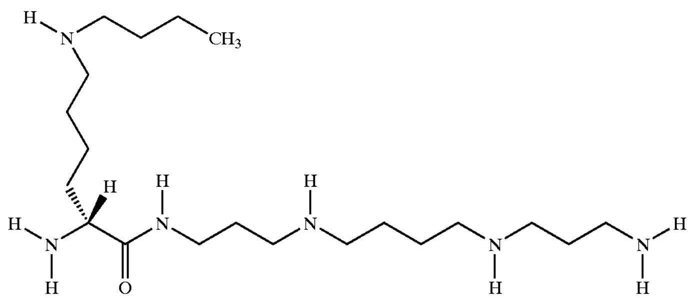 | 0.91 | 9.16 | 2.19 |
| IVB21 | 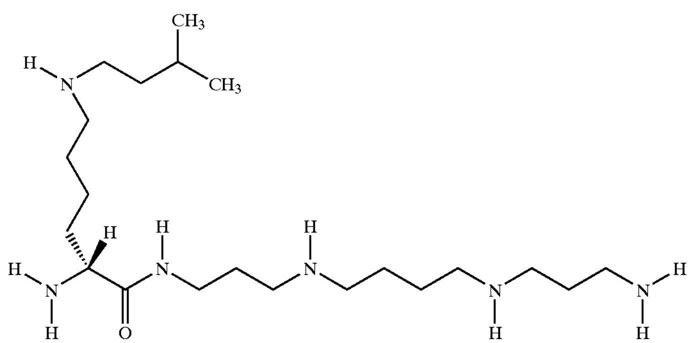 | 1.12 | 9.62 | 1.32 |
| IVB24 | 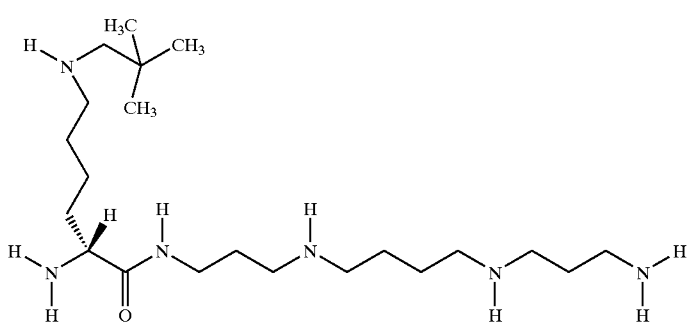 | 1.46 | 9.35 | 1.32 |
| IVB22 | 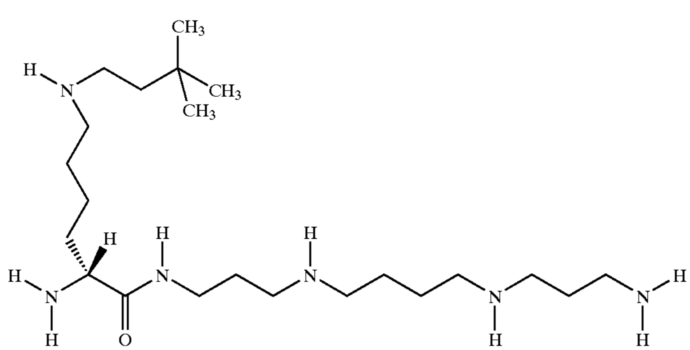 | 1.92 | 9.85 | 0.68 |

TABLE 2-continued

Chemical structure (with ID relative to FIG. 2), calculated logP value, HPLC retention time, and average EC$_{50}$ value for ε-alkylated spermine based analogs (FIG. 2, Series IV and V). Compound 1426 and one Series I compound are included for comparison.

| ID | Structure | LogP | Ret Time-Std | Ave EC$_{50}$ value |
|---|---|---|---|---|
| IVB6 | 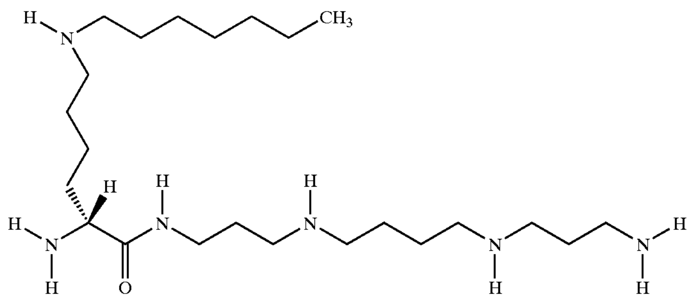 | 2.28 | 10.87 | 0.89 |
| IVB5 | 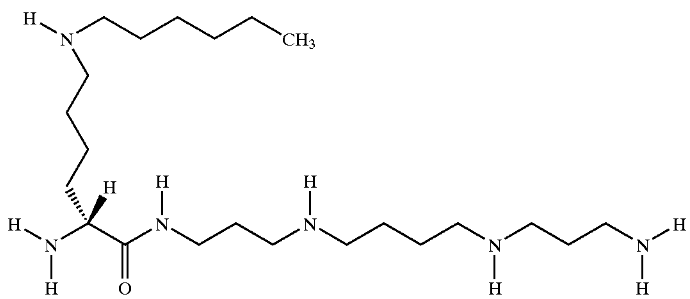 | 1.83 | 10.27 | 0.71 |
| IVB33 | 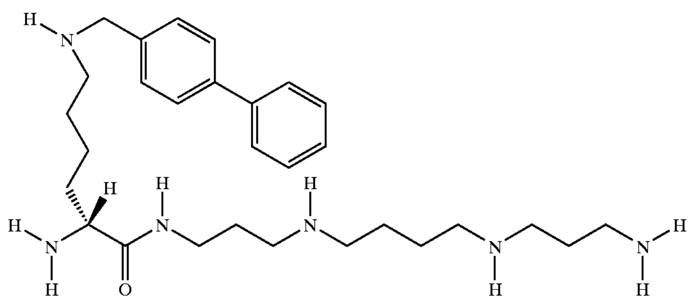 | 2.45 | 10.01 | 1.38 |
| IVB27 | 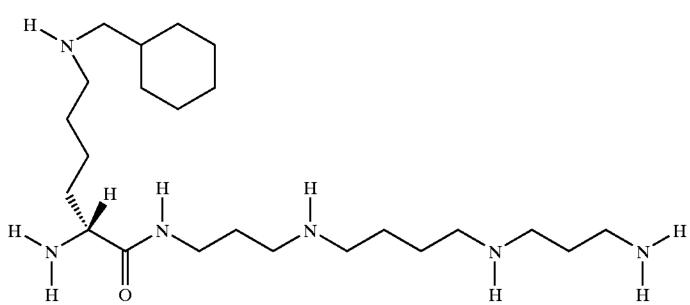 | 1.68 | 10.31 | 0.61 |

TABLE 2-continued

Chemical structure (with ID relative to FIG. 2), calculated logP value, HPLC retention time, and average $EC_{50}$ value for ε-alkylated spermine based analogs (FIG. 2, Series IV and V). Compound 1426 and one Series I compound are included for comparison.

| ID | Structure | LogP | Ret Time-Std | Ave $EC_{50}$ value |
|---|---|---|---|---|
| IVB25 | 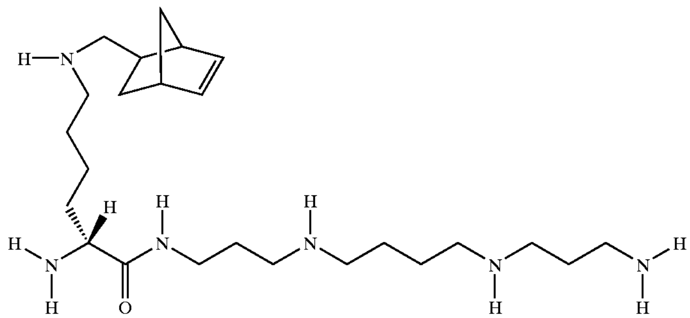 | 0.57 | 9.89 | 0.89 |
| VA21 | 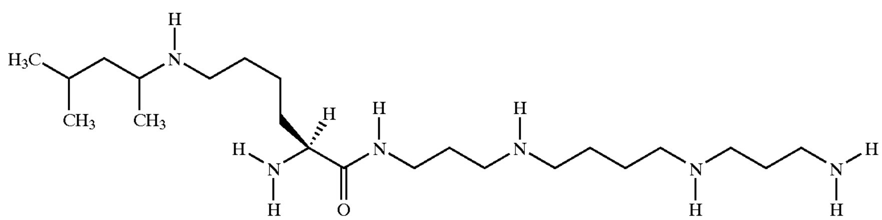 | 1.04 | 10.11 | 0.65 |
| 1426 | 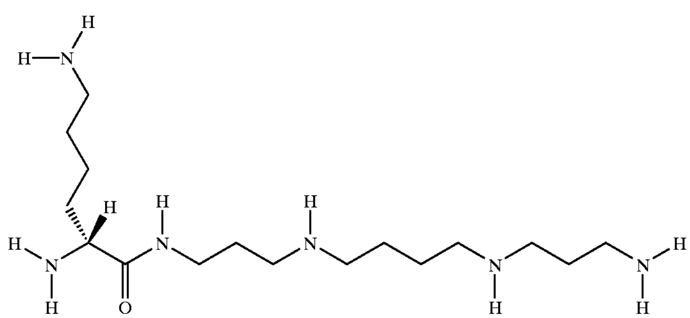 | Not cal-c'd | 6.68 | 3.68 |
| IA4 | 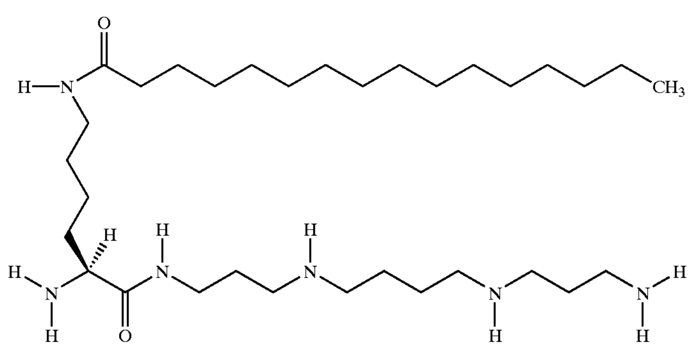 | 5.68 | 15.79 | 0.13 |

Preferred PAs of the invention with respect to Series IV and V type compounds are those with low $EC_{50}$ values, such as those with below about 5, about 6, about 7, about 8, about 9, about 10, about 12, about 14, about 16, about 18, or about 20 minute HPLC retention times.

Another way to measure relative hydrophobicity would be chromatographic techniques such as comparison of HPLC retention times on C18 reverse phase columns, longer retention times would represent greater relative hydrophobicity. The present invention utilized a dansylation protocol to form dansyl derivatives of the described analogs and analyzing these derivatives by fluorescence detection on C18 reverse phase HPLC. The difference between the elution of the peak due to the analog and the peak due to an internal standard (1,7-diaminoheptane) is shown for several representative analogs in Tables 1 and 2 above.

Figure 6:
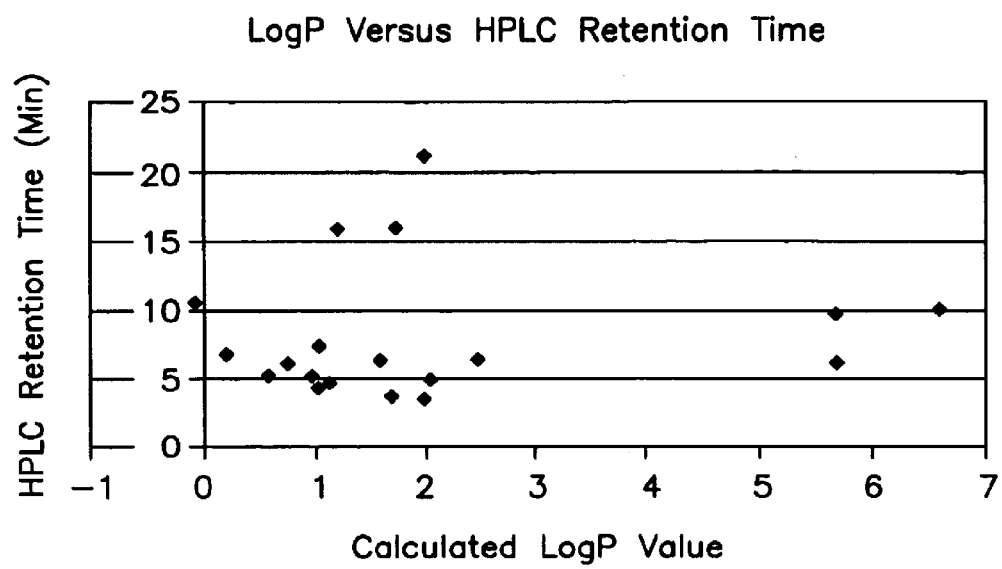
FIG. 6 presents calculated logP values versus HPLC retention time for dansylated derivatives of compounds shown in FIG. 2 (Series I).
Figure 7:
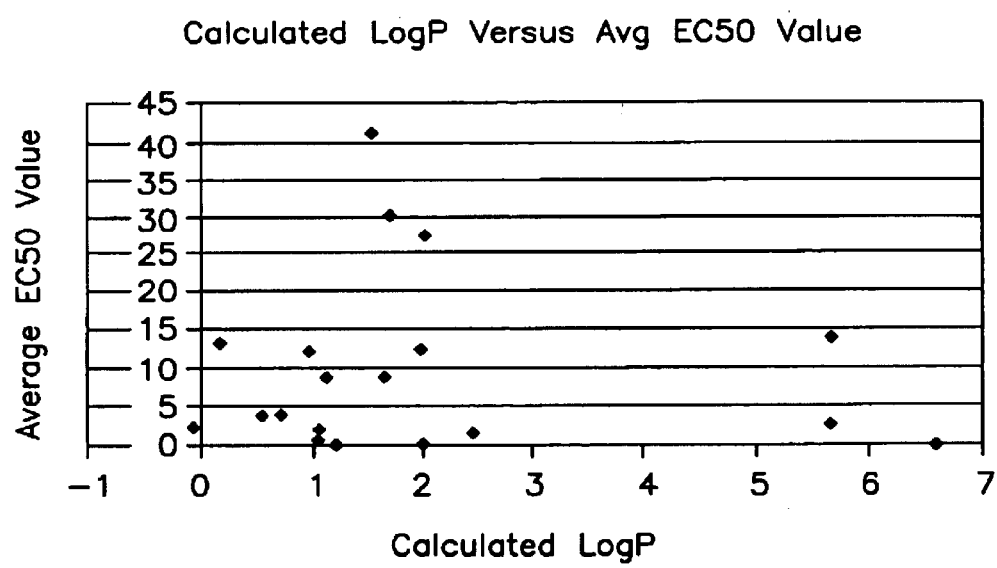
FIG. 7 presents calculated logP values versus average EC$_{50}$ values obtained for compounds with 4 cell lines (data for Series I compounds in Table 1).
Figure 8:
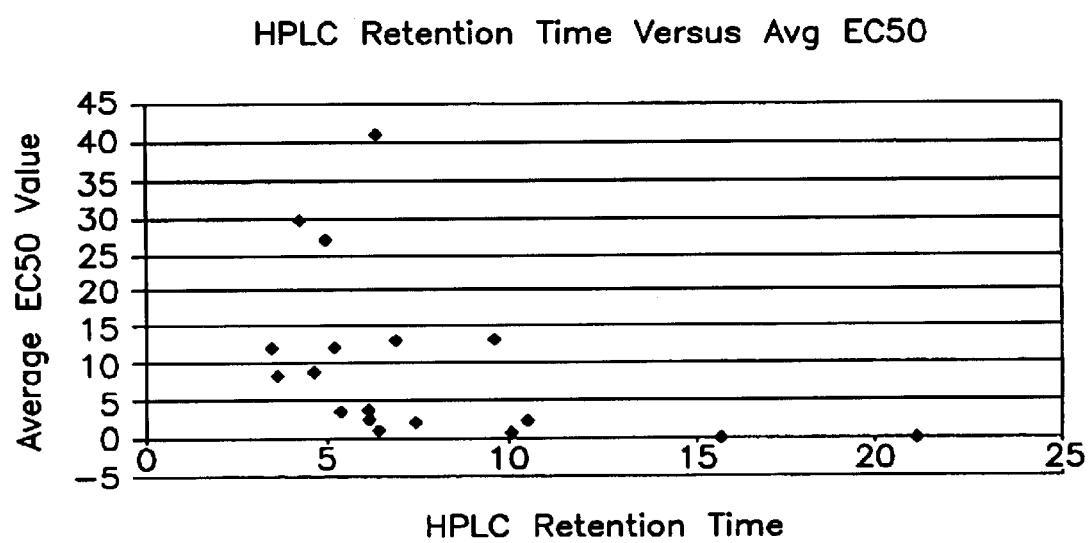
FIG. 8 presents HPLC retention time for dansylated derivatives of compounds shown in Table 2 (Series IV and V) versus average EC$_{50}$ values obtained for 4 cell lines (data in Table 1).
Figure 9:
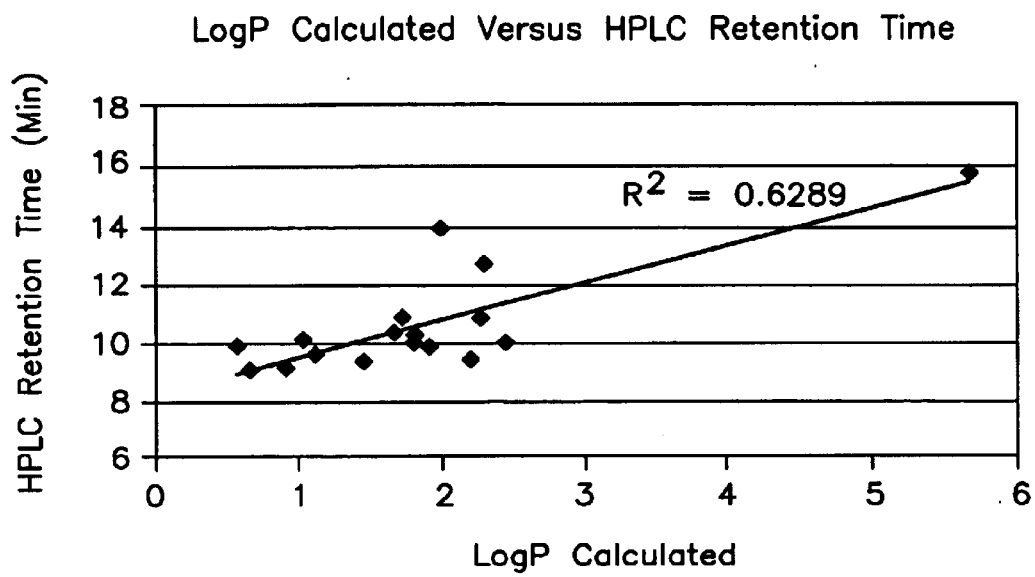
FIG. 9 shows the relationship between calculated logP values and HPLC retention time for dansylated derivatives of compounds shown in Table 2 (Series IV and V).
Figure 10:
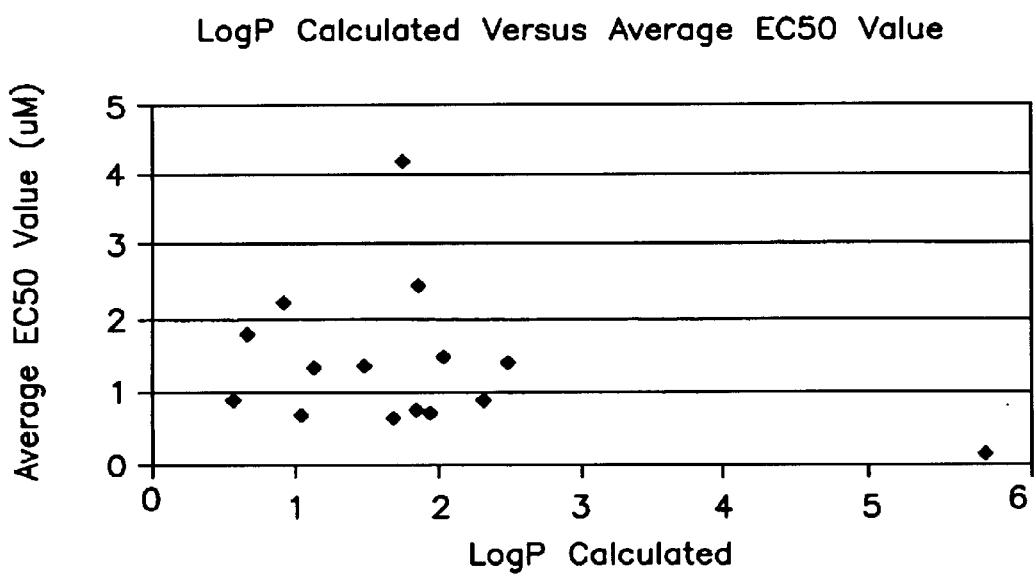
FIG. 10 presents calculated logP values versus average EC$_{50}$ values obtained for compounds with 4 cell lines (data for Series IV and V compounds in Table 2).
Figure 11:
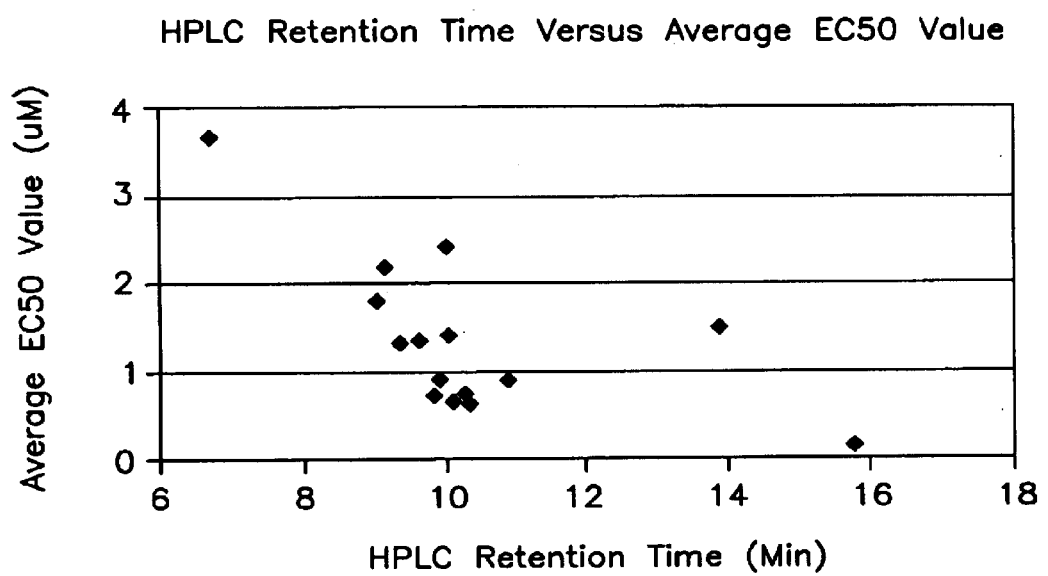
FIG. 11 presents HPLC retention time for dansylated derivatives of compounds shown in Table 2 (Series IV and V) versus average EC$_{50}$ values obtained for 4 cell lines using data in Table 1.
Figure 12A:
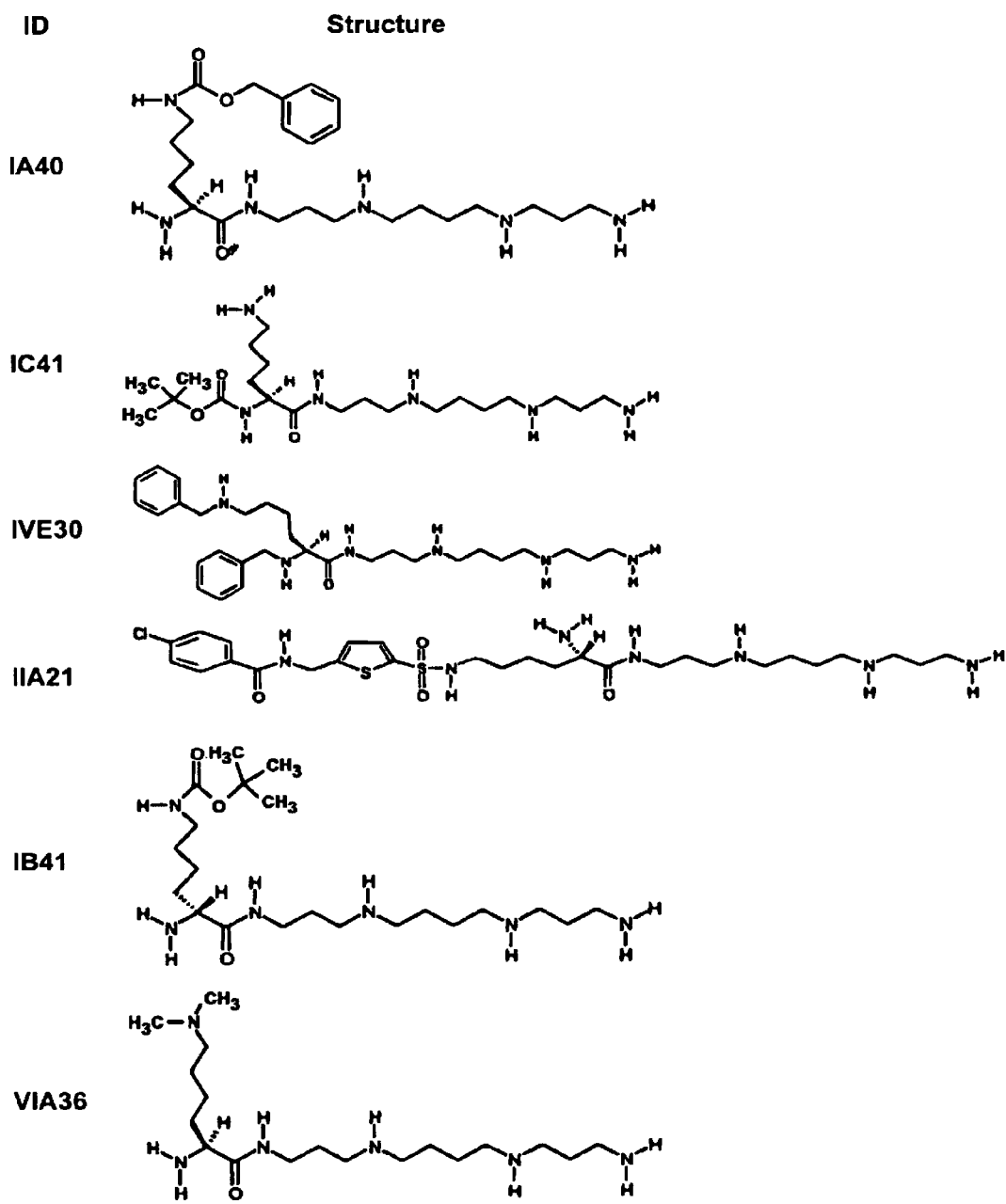
Figure 12B:
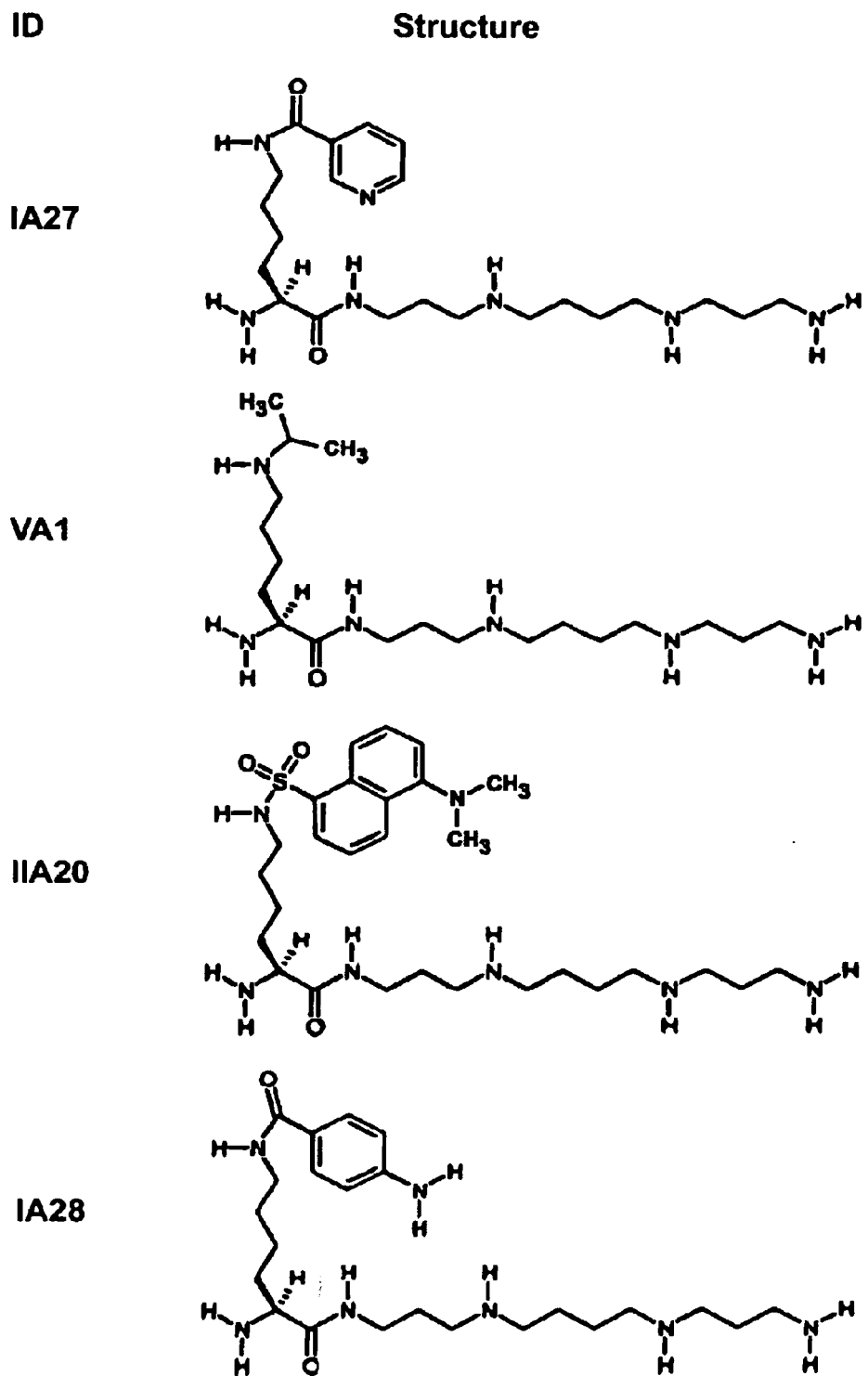
Figure 12C:
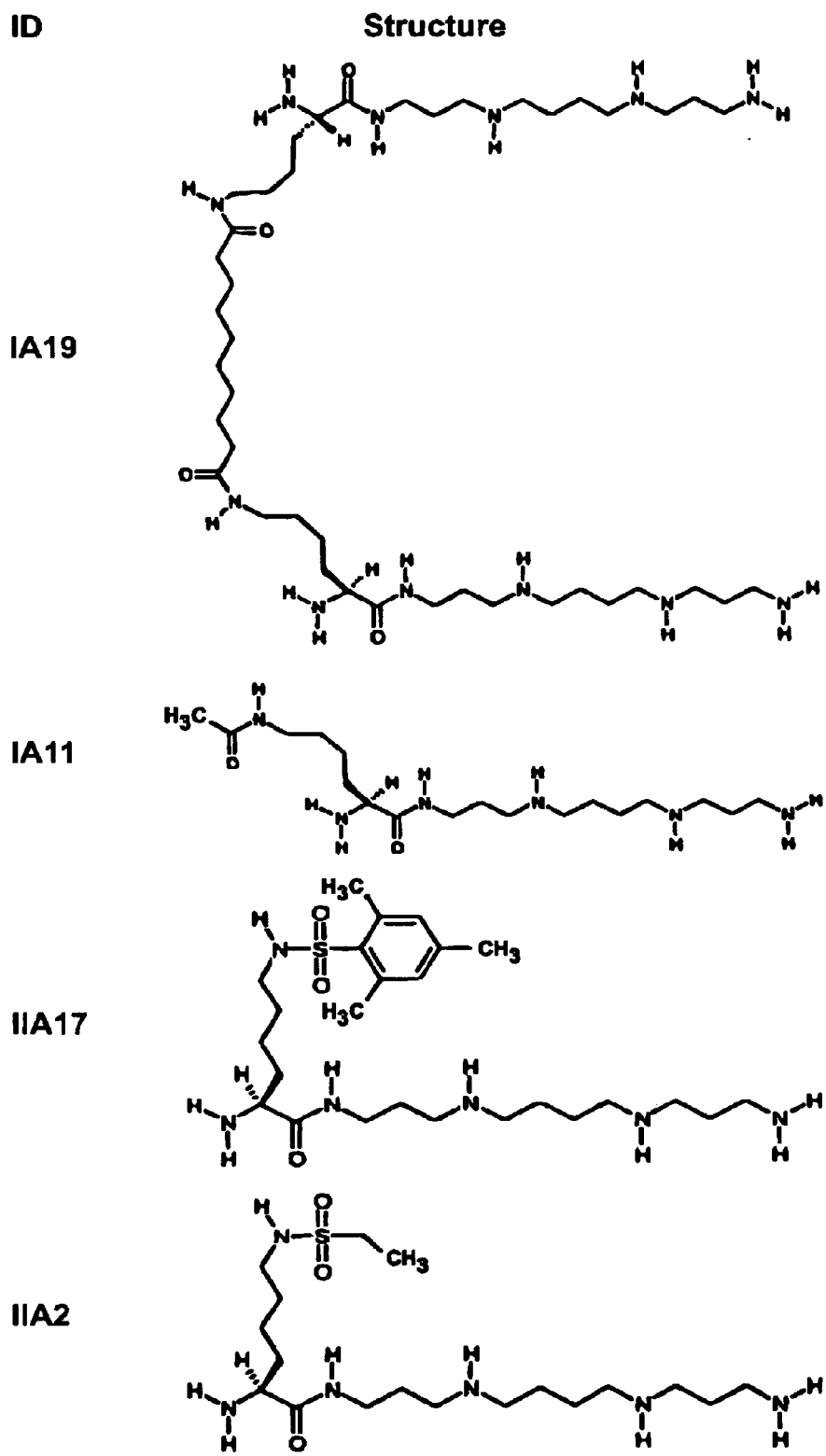
Figure 12D:
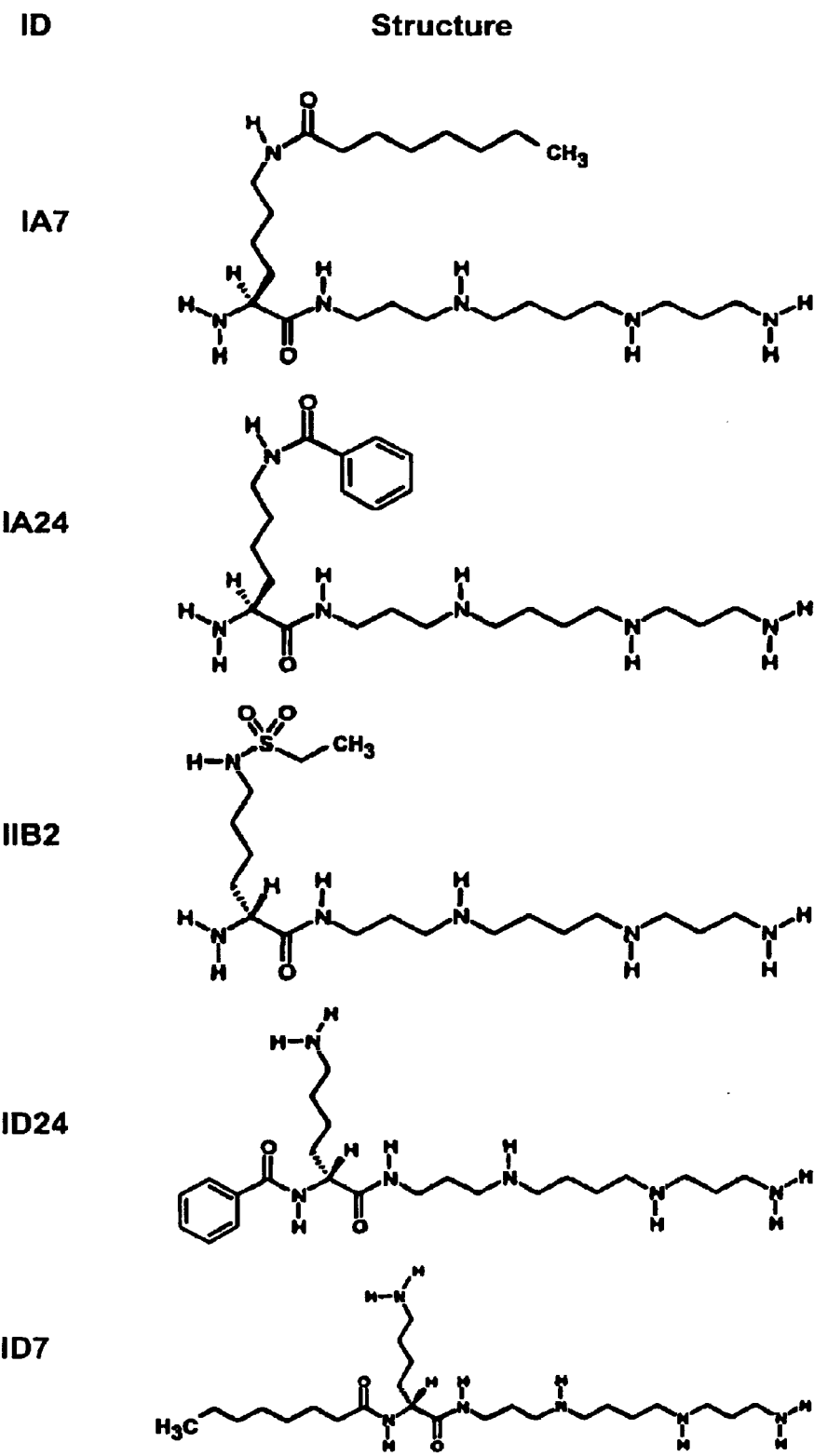
Figure 12F:
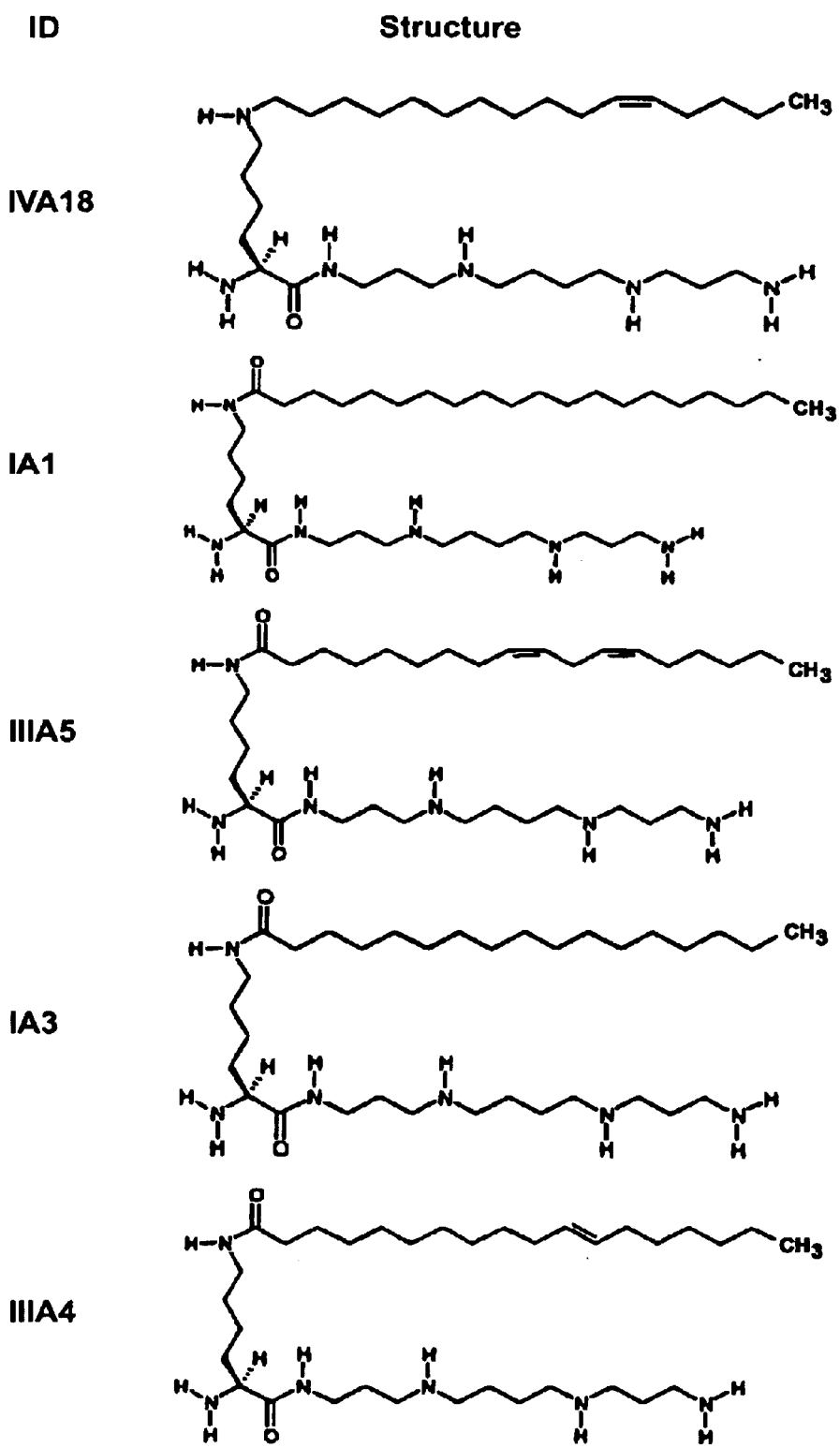
Figure 12G:
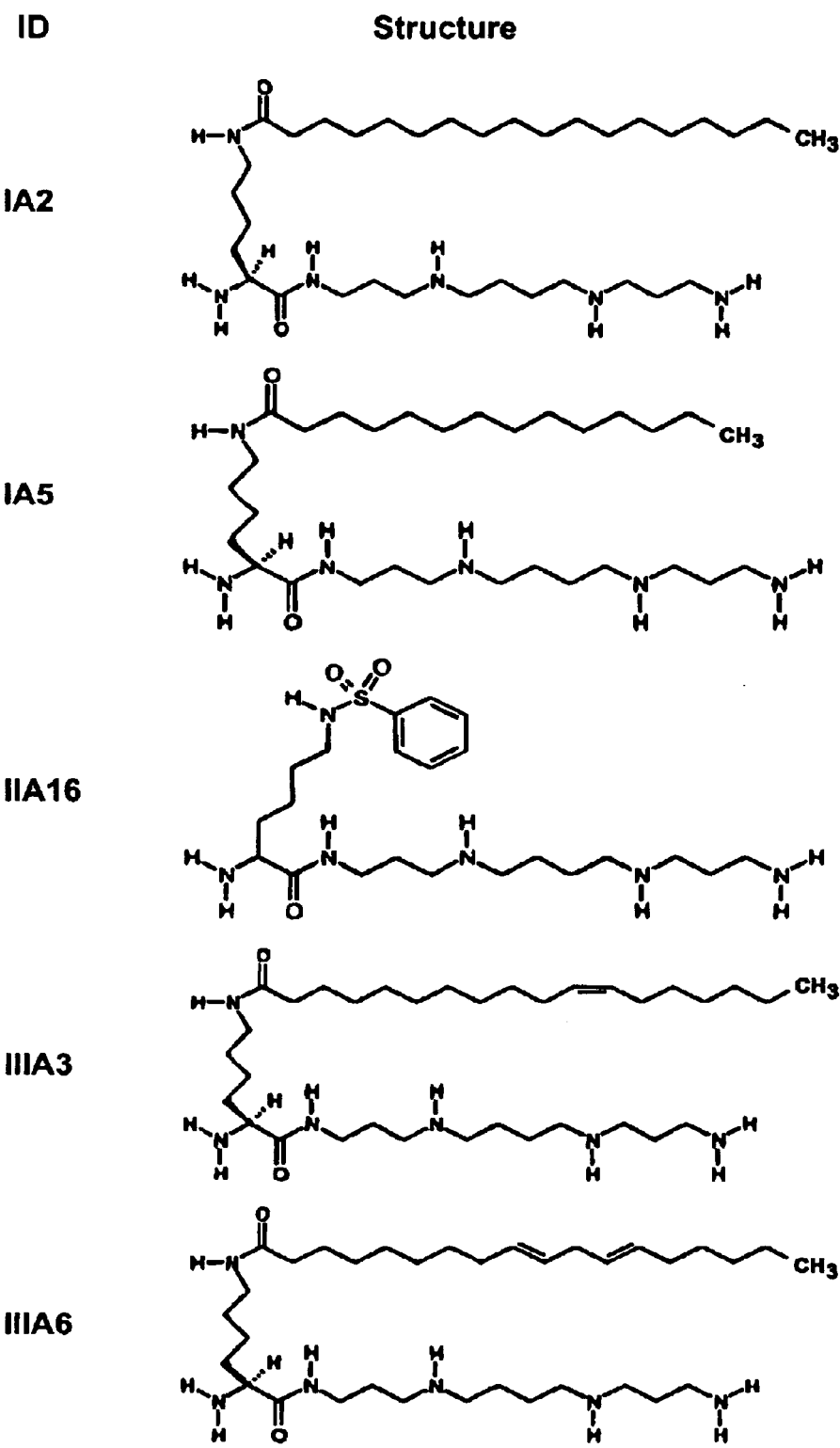
Figure 12H:
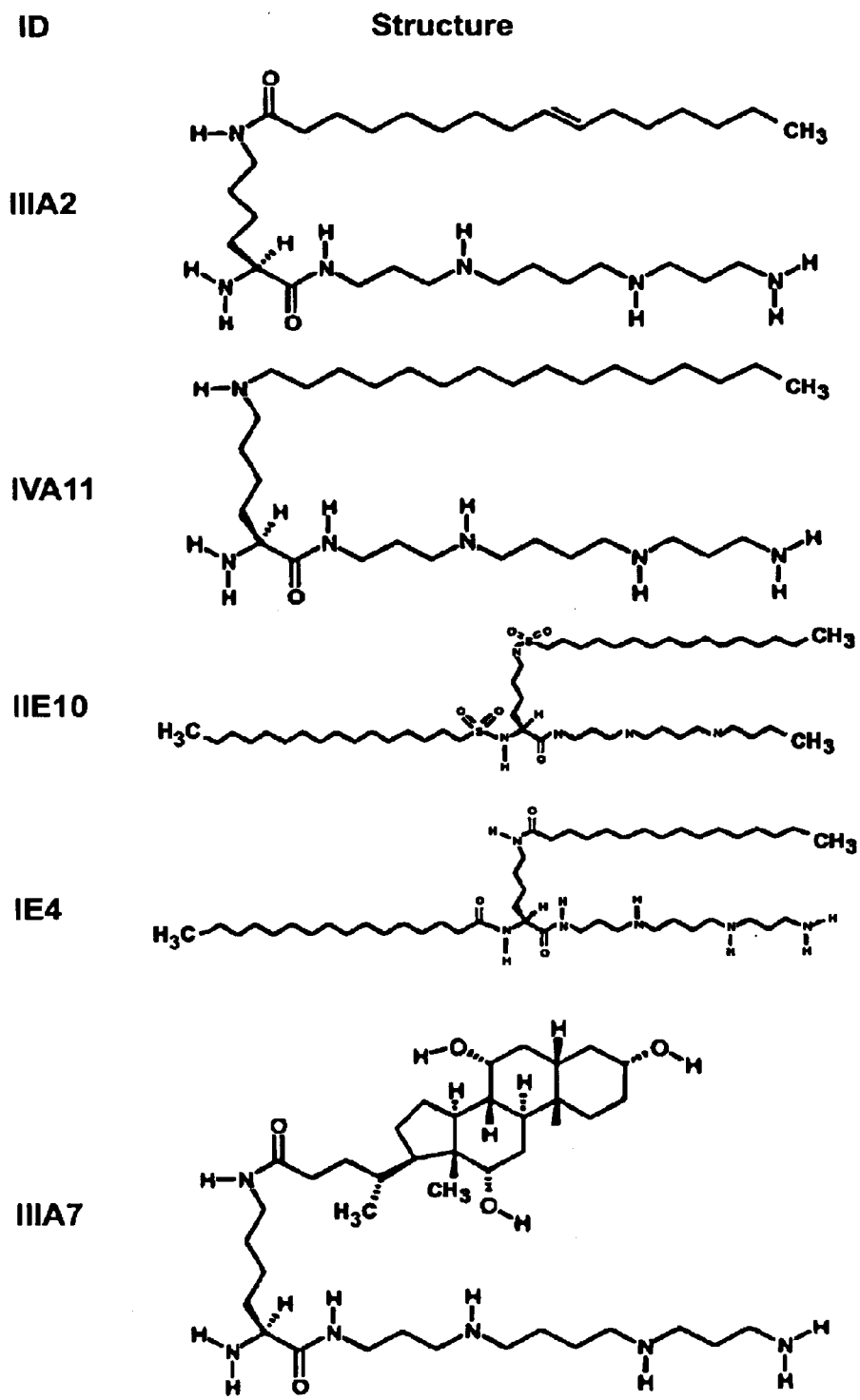
Figure 12I:
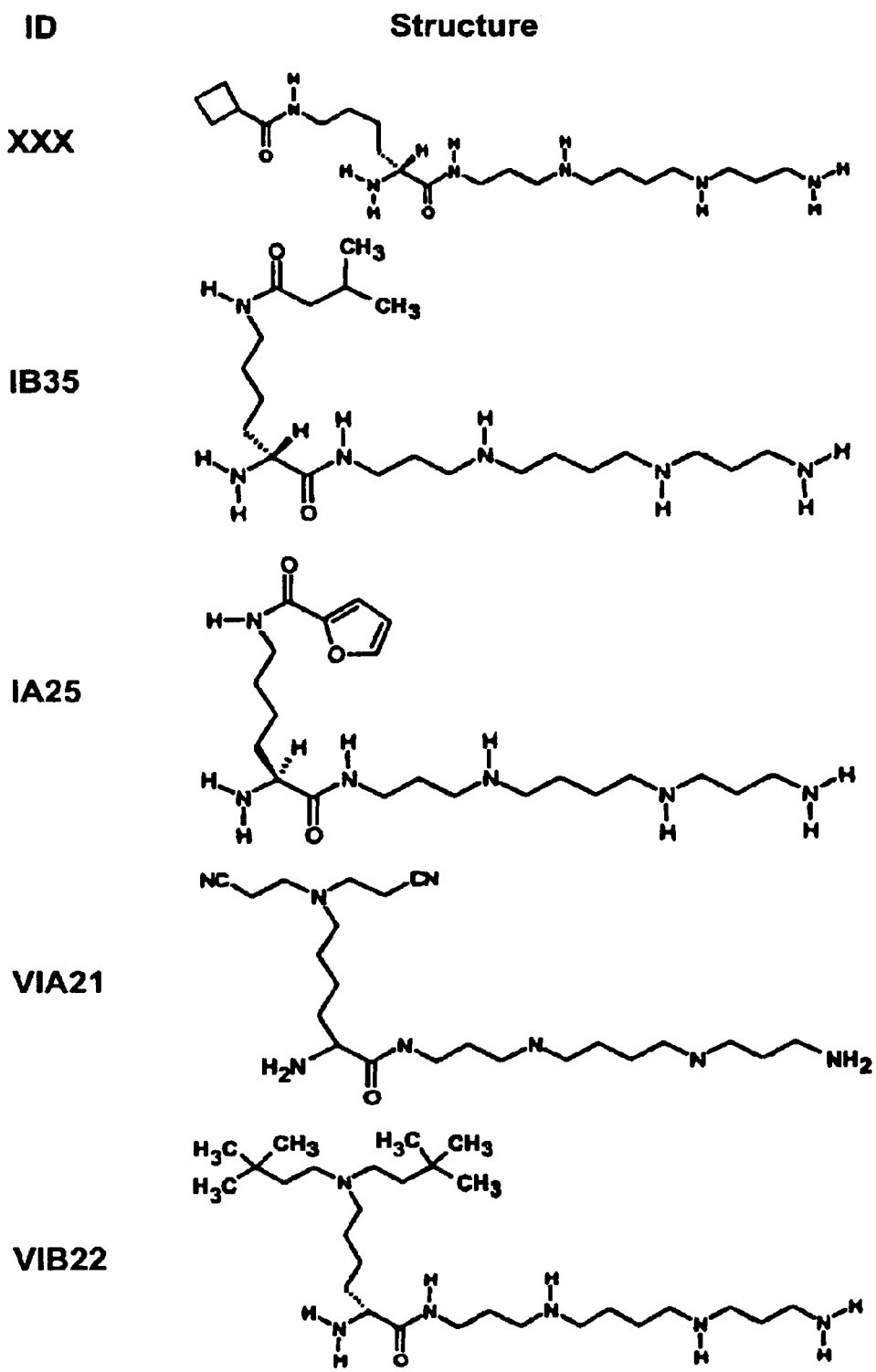
Figure 12J:
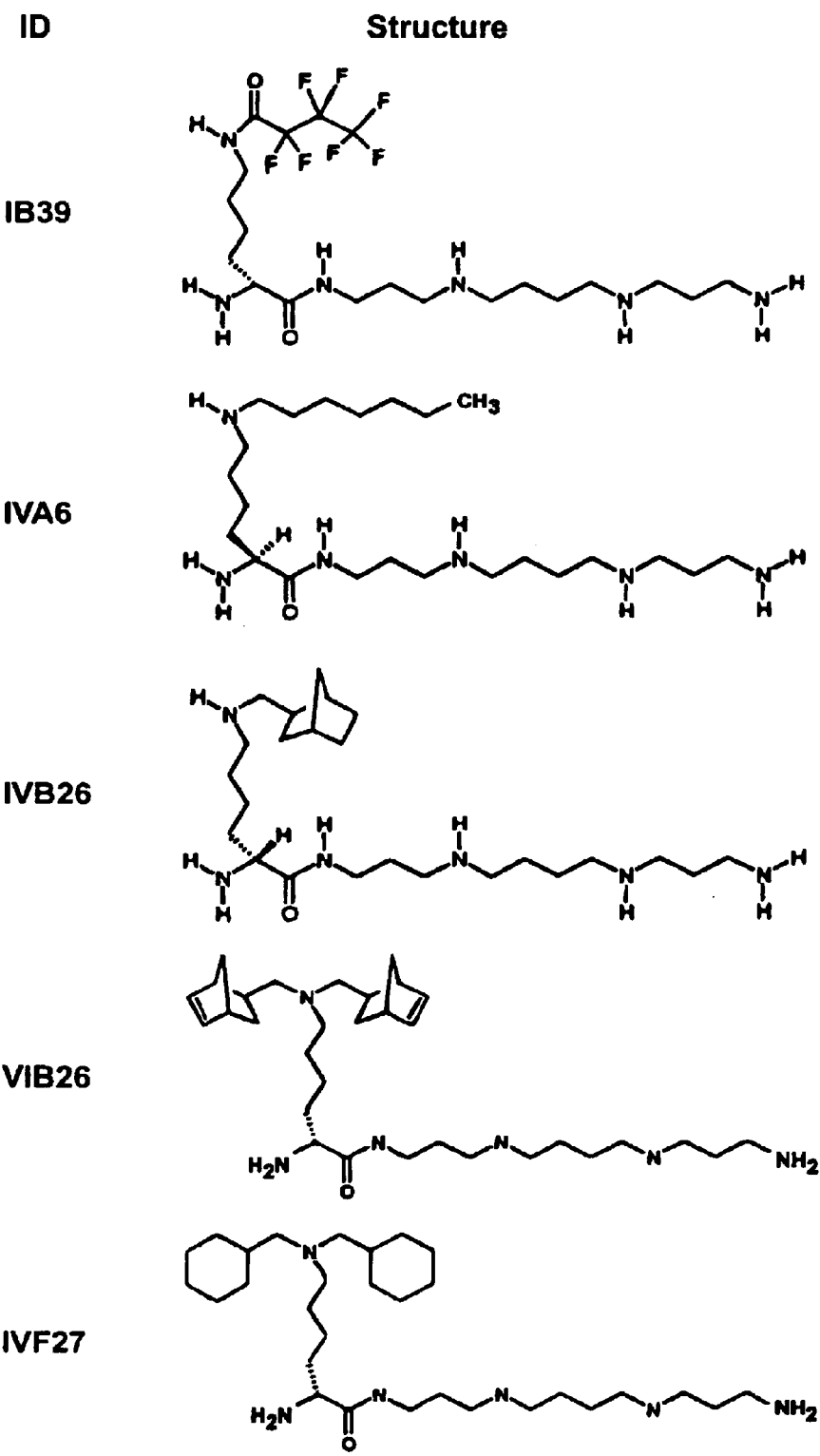
Figure 12K:
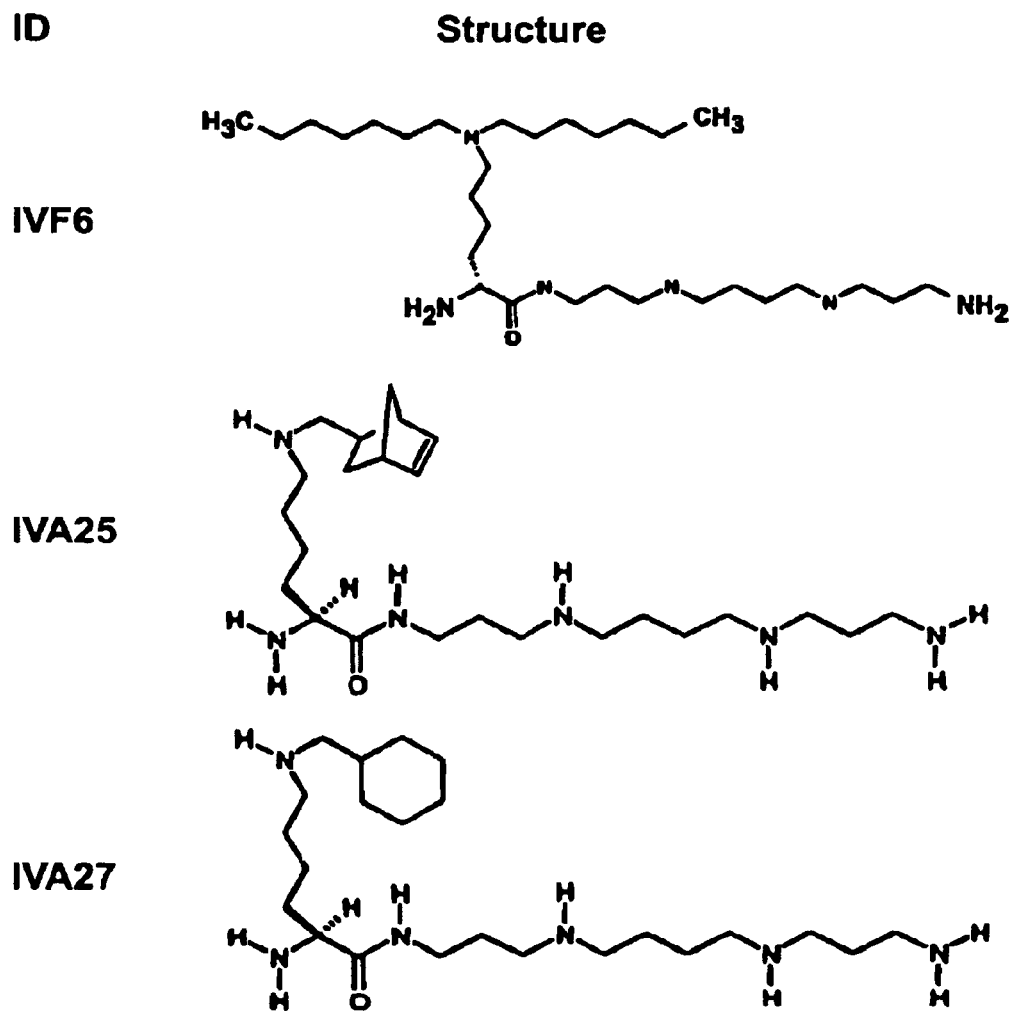

The relationship between calculated logP values and the HPLC retention time of the dansylated derivatives are plotted in FIGS. 6 and 9 for Series I and IV type compounds, respectively. The relationship between calculated logP and average $EC_{50}$ values are plotted in FIGS. 7 and 10 for Series I and IV type compounds, respectively. The relationship between HPLC retention times and average $EC_{50}$ values are plotted in FIGS. 8 and 11 for Series I and IV type compounds, respectively.

An additional compound hydrophobicity scale, specific for amino acids, was devised and measured by R. Wolfenden (Wolfenden, R.; Andersson, L.; Cullis, P. M.; Southgate, C. C. B. Affinities of amino acid side chains for solvent water *Biochemistry,* 1981, 20, 849–855.). They measured the equilibria of distribution of amino acid side chains between their dilute aqueous solutions and the vapor phase. They describe a scale of "hydration potentials" whereby buffered $H_2O$-vapor phase distribution measurements were made on the side-chain portions of the amino acids (e.g. methane for alanine, methanol for serine, n-butylamine for lysine or n-propylguanidine for arginine). If a side-chain had the potential for ionization a correction was made such that only the un-ionized fraction was considered. This was based on calculation of the un-ionized fraction using literature pKa values. The side chains for the twenty naturally occurring amino acids span a range of free energy values for the transfer from the vapor phase to $H_2O$ from 2.39 kcal/mol for hydrogen (glycine) or 1.94 kcal/mol for methane (alanine) to −7.00 kcal/mol for n-butylamine (lysine) or −14.6 kcal/mol for n-propylguanidine (arginine).

These values form a "hydration potential" scale, which is correlated with the potential that a given amino acid would be present on the outside, or hydrophilic portion of a protein versus the more hydrophobic interior of a protein. The authors state "that the energetic cost of removing hydrophilic side chains from water is much greater than the cost of pulling hydrophobic side chains into water, and, indeed, it has been observed that hydrophobic residues occur rather often at the surfaces of proteins." The present invention could use this scale to describe the lipophilicity of the substituent attached to the polyamine. The polyamine portion is removed before this analysis. As an example, it is also required that the α-amino and α-carboxylate groups of any analogs containing an α-amino acid be removed before analysis. By using this scale, any substituent with a free energy of transfer from the vapor phase to $H_2O$ less than that determined for n-butylamine (and thus correlated to lysine) of −7.00 kcal/mol would be expected to be a preferred polyamine transport inhibitor in comparison to the lysine-spermine conjugate (ORI 1202). This means any substituent that gives a hydration potential greater (more positive) than −7.00 kcal/mol, as defined in this scale, results in polyamine transport inhibitors with significant activity (values of free energy of transfer which are more negative mean a given compound would have a greater solubility in $H_2O$ than the vapor phase).

The preferred group of PAs wherein d is 4 and e is 0 includes both the L and D-stereoisomers due to the chiral carbon indicated by * in the above formula. Exemplary PAs such as ORI 1202 (L-Lys-spm), 1426 (D-Lys-spm), and those containing IA4 (FIG. 2) demonstrated potency in both the transporter inhibition and cell growth inhibition assays described below. PA ORI 1202 also displayed effectiveness in several anti-cancer mouse xenograft models. See Weeks, R. S., Vanderwerf, S. M., Carlson, C. L., Burns, M. R., O'Day, C. L., Cai, C. F., Devens, B. H., and Webb, H. K. *Exp. Cell Res.* 2000, 261, 293–302. and Devens, B. H., Weeks, R. S., Burns, M. R., Carlson, C. L., and Brawer, M. K. Prostate Cancer and Prostatic Diseases 2000, 3, 275–279.

Additional modification of the two primary amine groups in the acyl group in the above formula is readily accomplished by the availability of the primary amine groups for selective functionalization together with the commercial availability of orthogonally di-protected versions of $H_2N$ $(CH_2)_n CH(NH_2)COOH$ type molecules (where n ranges from 1 to 50 for example), such as lysine and ornithine.

Without being bound by theory, increases in the lipophilicity of the substituent at the above $R_1$ and $R_2$ positions may dramatically increase the affinity for the polyamine transporter. Increases in lipophilicity in the PAs of the invention may improve the inhibition of polyamine transport due to the presence of both hydrophilic and hydrophobic domains. Biological systems have a significant chemical problem when they attempt to move a very hydrophilic substance, such as polycationic polyamines, across their very hydrophobic outer membrane barriers. If the transporter moves the polyamines in their polycationic forms across this barrier, the transporter may do so via some mechanism for masking or minimizing their hydrophilicity. Mechanisms for this may include the formation of specific salt bridges between the polyamine and negatively charged residues on the protein or formation of a charged interior in the intermembrane pore. Because polyamine transport is known to be an energy dependant process, the transporter may have the task of providing a very specific polyamine shaped hydrophilic pore in the presence of the very hydrophobic environment of the membrane. For these reasons the transporter likely has hydrophobic residues for interactions with the membrane in close proximity to hydrophilic residues specific for interactions with the polyamine.

By designing PAs that contain both hydrophobic and hydrophilic domains, the present invention exploits the likely characteristics of a polyamine transporter to improve transport inhibition. Thus the present invention provides several series of PAs that contain both a polyamine-mimicking portion and a hydrophobic membrane-mimicking portion. These PAs have been inferred to have great affinity for the transporter, and they show substantially increased growth inhibition (in combination with a polyamine synthesis inhibitor) in comparison to PAs lacking a significantly hydrophobic domain. Probably for very similar reasons, the present PAs are also expected to show improved bioavailability through oral administration. Increases in lipophilicity are expected to enhance absorption after oral uptake.

It is also expected that the introduction of both hydrophilic and hydrophobic domains in the same molecule, as shown by those in the present invention, will also enable them to facilitate the transfer of nucleic acids through biological membranes. This property gives the analogs usefulness as transfer agents for anti-sense DNA for a number of scientific, analytical, diagnostic and therapeutic applications.

The above is supported by analysis of the results of extending a straight-chain aliphatic saturated hydrocarbon at position R (see FIG. 2, Series I) results in increases in cell growth inhibition in the presence of a polyamine synthesis inhibitor. The clear trend that longer hydrocarbon chains on this amide position increase potency is indicated by a comparison of spermine based compounds IA4, IA8, and IA11 as well as IB4, IB7, and IB8 (see Table 3). FIG. 4 shows the relationship between the length of the hydrocarbon substituent at the R position and the resulting $EC_{50}$ value in the presence of a polyamine synthesis inhibitor.

Table 3 shows the results from analysis of various exemplary PAs for their ability to inhibit cellular growth in combination with DFMO relative to control cells left untreated. $EC_{50}$ refers to the concentration of PA resulting in 50% of maximum cell growth inhibition in the presence of both DFMO and the PA. $K_i$ refers to the inhibition constant for polyamine transport based on double reciprocal Lineweaver-Burke plot analyses of four radioactive substrate concentrations (0.3–3 μM) and five inhibitor concentrations (0.01–1.0 μM) and a control. Compounds ORI 1202 and 1426 are included for comparison. See the Examples below.

TABLE 3

$EC_{50}$ values (μM) of representative polyamine analogs (see FIG. 2) determined in the presence of DFMO (1–5 mM). Also shown are the $IC_{50}$ results from analyses of various exemplary PAs. $IC_{50}$ refers to the concentration of PA that results in 50% of maximum cell growth inhibition in the presence of PA alone.

| Analog | Cell Line $EC_{50}$ (μM) | | | | AVG. $EC_{50}$ (μM) | Cell Line $IC_{50}$ (μM) | | | | $K_i$ (μM) |
|---|---|---|---|---|---|---|---|---|---|---|
| | A375 | MDA-MB-231 | PC-3 | SK-OV-3 | | A375 | MDA-MB-231 | PC-3 | SK-OV-3 | |
| IA40 | | 29.8 | 7.87 | | | | >300 | >300 | | 0.039 |
| | | 41.3 | 8.51 | | | | >300 | >300 | | |
| IC41 | | 36.9 | 16.9 | | | | >300 | 430 | | 0.191 |
| 1202 | 1.49 | 4.75 | 5.3 | 0.5 | 4.542 | | >300 | 560 | | 0.031 |
| | | 2.5 | 1.7 | 0.51 | | | | | | |
| | | 2.5 | 1.24 | | | | | | | |
| | | 13.5 | 1.24 | | | | | | | |
| | | 6.9 | 10.3 | | | | | | | |
| | | 8.7 | 0.822 | | | | | | | |
| | | 8.4 | 7.78 | | | | | | | |
| | | 4.35 | 4.1 | | | | | | | |
| | | | 6.2 | | | | | | | |
| | | | 2.6 | | | | | | | |
| IVE30 | | 4.2 | 1.7 | | | | | | | |
| IIA21 | | 1.4 | 0.46 | | | | | | | |
| IB41 | | 31.9 | 6.73 | | | | | | | |
| 1426 | 1.91 | 4.5 | 5 | 0.51 | 2.254 | 1620 | 1840 | 1840 | 2530 | 0.034 |
| | 1.29 | 1.5 | 8.02 | 0.93 | | >100 | >100 | >100 | >100 | |
| | 2.2 | 1.27 | 0.55 | 6.09 | | >300 | >300 | >300 | >300 | |
| | 1.75 | 4.25 | 2.12 | 1.36 | | >100 | >300 | >300 | >300 | |
| | 0.829 | 2.02 | 0.704 | 1.41 | | >100 | >100 | >100 | >300 | |
| | 2.7 | 1.27 | 0.52 | 0.53 | | >100 | >100 | >100 | >100 | |
| | | 2.1 | 0.26 | 2.7 | | | >100 | >100 | >100 | |
| | | 3.99 | 0.89 | >100 | | | | >100 | >100 | |
| | | 3.1 | 2.98 | 0.68 | | | | | >100 | |
| | | | 4 | 2.7 | | | | | | |
| IIA20 | 0.405 | 1.61 | 0.463 | 2.65 | 1.282 | >30 | >30 | >30 | >30 | |
| IA4 | 0.049 | 0.194 | 0.129 | 0.273 | 0.077 | >30 | >30 | >30 | >30 | 0.0015 |
| | 0.049 | 0.057 | 0.028 | 0.069 | | 61.5 | 62.4 | >3 | >3 | |
| | 0.008 | 0.017 | <0.001 | 0.252 | | >3 | >3 | >3 | >3 | |
| | 0.005 | 0.005 | 0.001 | 0.049 | | >3 | >3 | >3 | >3 | |
| | 0.004 | 0.009 | <0.1 | <0.1 | | >3 | >3 | 18.1 | 18.6 | |
| | <0.1 | <0.1 | | 0.182 | | 58.3 | 62 | | >3 | |
| IA28 | 1.66 | >30 | 0.982 | >30 | | >30 | >30 | >30 | >30 | |
| IA19 | 0.214 | >30 | >30 | >30 | | >30 | >30 | >30 | >30 | |
| IA11 | >30 | >30 | 2.3 | >30 | | >30 | >30 | >30 | >30 | |
| IB4 | 0.071 | 0.168 | 0.197 | 0.297 | 0.105 | >30 | >30 | >30 | >30 | 0.017 |
| | <0.01 | <1 | 0.044 | 0.121 | | 23.1 | 58.9 | 26.1 | 27.7 | |
| | 0.026 | 0.031 | 0.177 | 0.175 | | >3 | >30 | >3 | >3 | |
| | 0.015 | 0.072 | 0.09 | 0.121 | | >3 | >3 | >3 | >3 | |
| | <0.1 | 0.051 | <0.1 | <0.1 | | 55.4 | >3 | 15.8 | 12.6 | |
| | 0.011 | <0.1 | 0.116 | 0.157 | | >3 | 56 | >3 | >3 | |
| | | 0.06 | | | | | | >3 | | |
| IIA17 | 0.629 | <1 | 0.18 | 2.59 | | >30 | 605 | >30 | >30 | |
| IIA2 | >30 | | >30 | >30 | | >30 | | >30 | >30 | |
| IA7 | 2.3 | 1.12 | 1.35 | >30 | 6.229 | >30 | >30 | >30 | >30 | |
| | 1.75 | | 0.853 | 30 | | >30 | | >30 | >30 | |
| IA24 | 1.56 | | >30 | | | >30 | | >30 | | |
| IB24 | >30 | >30 | >30 | >30 | >30 | >30 | >30 | >30 | >30 | |
| IB7 | 2.61 | >30 | 1.27 | >30 | 11.210 | >30 | >30 | >30 | >30 | |
| | 4.87 | 19 | | 28.3 | | >30 | >30 | | >30 | |
| IIB2 | 7.25 | | 3.64 | >30 | | >30 | | >30 | >30 | |
| ID24 | 5.98 | 4.75 | 3.3 | >30 | | >30 | >30 | >30 | >30 | |
| ID7 | 5.29 | 8.25 | 7.42 | 17.2 | 9.540 | >30 | >30 | >30 | >30 | |
| IID17 | 5.87 | 5.1 | 4.09 | 23.9 | 9.740 | >30 | >30 | >30 | >30 | |
| IID2 | >30 | >30 | >30 | >30 | >30 | >30 | >30 | >30 | >30 | |
| ID25 | 8.78 | 8.76 | 5.27 | >30 | | >30 | >30 | >30 | >30 | |
| ID4 | 0.44 | 0.636 | 1.33 | 2.64 | 1.262 | 17.9 | 18.6 | 18.7 | 18.1 | |
| IB25 | 4.27 | | 3 | 22.9 | | >30 | | >30 | >30 | |
| IIB10 | 0.026 | 0.169 | 0.099 | 0.134 | 0.110 | 18 | >30 | 22 | 18.1 | 0.002 |
| | 0.044 | | 0.074 | 0.224 | | 17.7 | | 19.9 | 23.1 | |
| IB6 | 1.85 | | 1.93 | 2.84 | | >30 | | >30 | >30 | 0.075 |
| IIB17 | 1.52 | | 0.919 | 26.2 | | >30 | | >30 | >30 | |

TABLE 3-continued

EC$_{50}$ values ($\mu$M) of representative polyamine analogs (see FIG. 2) determined in the presence of DFMO (1–5 mM). Also shown are the IC$_{50}$ results from analyses of various exemplary PAs. IC$_{50}$ refers to the concentration of PA that results in 50% of maximum cell growth inhibition in the presence of PA alone.

| Analog | Cell Line EC$_{50}$ ($\mu$M) | | | | AVG. EC$_{50}$ ($\mu$M) | Cell Line IC$_{50}$ ($\mu$M) | | | | K$_i$ ($\mu$M) |
|---|---|---|---|---|---|---|---|---|---|---|
| | A375 | MDA-MB-231 | PC-3 | SK-OV-3 | | A375 | MDA-MB-231 | PC-3 | SK-OV-3 | |
| IIA10 | 0.016 | 0.364 | 0.024 | 0.098 | 0.072 | 18.3 | >30 | 19 | 26.7 | 0.004 |
| | 0.01 | 0.052 | 0.039 | 0.083 | | 18.4 | >30 | 17.1 | 24.1 | |
| | 0.009 | 0.022 | 0.071 | 0.08 | | >3 | >3 | >3 | >3 | |
| IIIA1 | 0.076 | 0.197 | 0.386 | 0.398 | 0.264 | >30 | >30 | >30 | >30 | |
| IIIB1 | 0.17 | 0.491 | 0.099 | 1.57 | 0.583 | >30 | >30 | >30 | >30 | 0.054 |
| IVA18 | 0.05 | 0.107 | 0.075 | 0.14 | 0.079 | >30 | >30 | >3 | >3 | |
| | 0.061 | 0.038 | | | | >3 | >3 | | | |
| IA1 | 0.01 | 0.016 | 0.014 | 0.083 | 0.017 | 18.5 | 15.3 | >3 | >3 | 0.015 |
| | 0.004 | 0.012 | 0.005 | 0.02 | | >3 | >3 | >3 | >3 | |
| | 0.002 | 0.003 | | | | >3 | >3 | | | |
| IIIA5 | 0.084 | 0.207 | | | | >30 | >30 | | | |
| IA3 | <0.01 | 0.032 | 0.022 | 0.097 | 0.053 | 23 | >30 | 18.3 | >30 | |
| | 0.01 | 0.018 | 0.022 | 0.167 | | >3 | >3 | >3 | >3 | |
| IIIA4 | 0.014 | 0.039 | 0.056 | 0.134 | 0.061 | 17.3 | >30 | 23.1 | >30 | |
| IA2 | <0.01 | 0.019 | 0.016 | 0.027 | 0.014 | 13 | 27.3 | 13.3 | 16.8 | 0.0014 |
| | 0.002 | 0.006 | 0.007 | 0.021 | | >3 | >3 | >3 | >3 | |
| IA5 | 0.025 | 0.208 | 0.189 | 4.6 | 1.256 | >30 | >30 | 9.87 | 21.5 | |
| IIA16 | 1.21 | 2.57 | 0.72 | >30 | | >30 | >30 | >30 | >30 | |
| IIIA3 | 0.017 | 0.03 | 0.029 | 0.082 | 0.040 | >30 | >30 | >30 | >30 | |
| IIIA6 | 0.018 | 0.047 | 0.06 | 0.095 | 0.055 | 22.3 | >30 | 25.8 | >30 | |
| IIIA2 | 0.01 | 0.029 | 0.022 | 0.076 | 0.034 | >30 | >30 | >30 | >30 | |
| IVA11 | 0.01 | 0.019 | 0.046 | 0.081 | 0.039 | >3 | >3 | >3 | >3 | |
| IIE10 | | 0.392 | 0.152 | 0.272 | | | 24.5 | 14.3 | 20.1 | |
| IE4 | | 0.267 | 0.2 | 0.132 | | | 17.9 | 21.5 | 7.25 | |
| IB2 | 0.016 | 0.028 | 0.091 | 0.198 | 0.083 | >3 | >3 | >3 | >3 | |
| IIIA7 | 0.087 | 0.215 | 0.255 | 2.94 | 0.874 | >3 | >3 | >3 | >3 | |
| VA21 | 0.167 | 0.392 | 0.83 | 1.86 | 1.296 | >300 | >300 | >100 | >300 | |
| | 0.141 | 0.85 | 0.654 | 2.3 | | >300 | >100 | >100 | >100 | |
| | 0.63 | 1.377 | 0.6 | 3.669 | | >100 | >100 | >100 | >100 | |
| | 0.498 | 1.3 | 2.5 | 2.3 | | >100 | >100 | >100 | >100 | |
| | 0.48 | 1.6 | | 3.1 | | >100 | >100 | | >100 | |
| | 0.67 | | | | | >100 | >100 | | | |
| IVB25 | 0.32 | 0.59 | 0.33 | 1.75 | 0.939 | >300 | >100 | >100 | 19 | |
| | 0.4 | 0.93 | 0.59 | 2.6 | | 61 | 61 | >100 | >100 | |
| IVB27 | 0.14 | 0.39 | 0.58 | 0.87 | 0.414 | >300 | >100 | >100 | 33.9 | |
| | 0.17 | 0.14 | 0.12 | 0.9 | | >100 | >100 | >100 | >100 | |
| IVB33 | | 1.46 | 0.77 | 1.91 | | | >100 | >100 | 72.9 | |
| IB29 | | 3.38 | 0.56 | 2.41 | | | >100 | >100 | >70 | |
| IVB5 | 0.53 | 0.224 | 0.295 | 1.65 | 0.868 | >100 | >100 | >100 | >100 | |
| | | 0.9 | 0.58 | 1.9 | | | >100 | >100 | >100 | |
| IVB6 | 0.17 | 0.193 | <0.1 | 0.478 | 0.365 | >100 | >100 | >100 | >100 | |
| | | 0.34 | 0.18 | 0.83 | | | >100 | >100 | >100 | |
| IVB22 | 1.2 | 0.194 | 0.25 | 1.553 | 1.335 | >100 | >100 | >100 | >100 | |
| | 1.95 | 0.56 | 1.2 | 2.6 | | >100 | >100 | >100 | >100 | |
| | | 2.08 | 0.57 | 2.53 | | | >100 | >100 | >100 | |
| IB30 | 0.35 | 2.4 | 0.58 | 4.7 | 1.244 | >100 | >100 | >100 | >100 | |
| | 0.21 | 0.55 | 0.7 | 0.46 | | 7.4 | 84.4 | 18.8 | 17.8 | |
| IB32 | 0.67 | 4.4 | | 5.6 | | >100 | >100 | >100 | >100 | |
| XXX* | 2.76 | 6.761 | 6.218 | 24.1 | 9.960 | >100 | >100 | >100 | >100 | |
| IB10 | 3.633 | 5.962 | 8 | 29.091 | 11.672 | >100 | >100 | >100 | >100 | |
| IVB24 | 0.625 | 0.961 | 0.975 | 2.732 | 3.138 | >100 | >100 | >100 | >100 | |
| | 0.51 | 1.4 | 15.6 | 2.3 | | 84.4 | >100 | 18.8 | >100 | |
| IVB21 | 0.526 | 0.653 | 1.454 | 2.7 | 1.522 | >100 | >100 | >100 | >100 | |
| | 0.5 | 0.87 | 0.87 | 4.6 | | 71 | >100 | >100 | >100 | |
| IVB3 | 0.753 | 1.615 | 1.657 | 4.791 | 2.204 | >100 | >100 | >100 | >100 | |
| IVB23 | 0.636 | 1.636 | 1.139 | 3.788 | 1.787 | >100 | >100 | >100 | >100 | |
| | 0.7 | 1.8 | 2 | 2.6 | | | >100 | >100 | >100 | |
| IB33 | 2.649 | 4.726 | 6.408 | 20.526 | 8.577 | >100 | >100 | >100 | >100 | |
| IB9 | 4.4 | 14.1 | 3.92 | 23.5 | 11.480 | >100 | >100 | >100 | >100 | |
| IB34 | 6.25 | 11.4 | 1.93 | 13.6 | 8.295 | >100 | >100 | >100 | >100 | |
| IB36 | 6.69 | 25 | 2.24 | 73.7 | 26.908 | >100 | >100 | >100 | >100 | |
| IB26 | 0.51 | 0.93 | 0.46 | 2.32 | 0.955 | >100 | >100 | >100 | >100 | |
| | 0.22 | 0.6 | 0.8 | 1.8 | | 24.6 | >100 | >100 | >100 | |
| IB8 | 2.6 | 1.25 | 2.16 | 8.18 | 3.548 | >100 | >100 | >100 | >100 | |
| IB35 | >100 | >100 | >100 | >100 | >100 | >100 | >100 | >100 | >100 | |
| VA26 | 1.44 | 4.5 | 1.9 | 7.8 | 3.910 | >100 | >100 | >100 | >100 | |
| VA27 | 3.7 | 12 | 1.6 | 8.5 | 6.450 | >100 | >100 | >100 | >100 | |
| VA22 | 0.79 | 1.3 | 0.67 | 4.7 | 6.983 | >100 | >100 | >100 | >100 | |
| | 0.9 | 2.4 | 2 | 43.1 | | 83.5 | >100 | >100 | >100 | |
| IVB28 | 4.9 | 6.4 | 13.5 | 18.1 | 10.725 | 5.6 | 18.9 | 17.8 | 19.8 | |

TABLE 3-continued

EC$_{50}$ values ($\mu$M) of representative polyamine analogs (see FIG. 2) determined in the presence of DFMO (1–5 mM). Also shown are the IC$_{50}$ results from analyses of various exemplary PAs. IC$_{50}$ refers to the concentration of PA that results in 50% of maximum cell growth inhibition in the presence of PA alone.

| Analog | Cell Line EC$_{50}$ ($\mu$M) | | | | AVG. EC$_{50}$ ($\mu$M) | Cell Line IC$_{50}$ ($\mu$M) | | | | K$_i$ ($\mu$M) |
|---|---|---|---|---|---|---|---|---|---|---|
| | A375 | MDA-MB-231 | PC-3 | SK-OV-3 | | A375 | MDA-MB-231 | PC-3 | SK-OV-3 | |
| IB37 | 18.3 | 17.8 | 39.3 | 65 | 35.100 | 19.8 | >100 | >100 | 18.3 | |
| IB38 | 1.08 | 17.3 | 2.4 | 32.7 | 13.370 | 21.3 | 63.9 | 28 | 60.1 | |
| VB28 | 0.45 | 0.41 | 0.75 | 2.4 | 0.905 | >100 | >100 | >100 | >100 | |
| | 0.3 | 0.43 | 0.8 | 1.7 | | 64.5 | >100 | >100 | >100 | |
| IA25 | | | | | | | | | | |
| VIA21 | | 0.68 | 0.19 | >100 | | | >100 | >100 | >100 | |
| VIB22 | | 0.38 | 5.49 | >100 | | | 30 | >100 | >100 | |
| IB39 | | 52.5 | >100 | >100 | | | 4.26 | >100 | >100 | |
| IVA6 | | | | | | | | | | |
| IVB26 | 2.4 | 1.99 | 0.91 | 7.56 | 3.410 | >100 | >100 | >100 | >100 | |
| | | | 1.53 | 6.07 | | | | >100 | >100 | |
| VIB26 | 4.43 | 8.04 | 1.58 | 17.32 | 7.843 | >100 | >100 | >100 | >100 | |
| IVF27 | 2.18 | 2.34 | 0.5 | 2.16 | 1.795 | >100 | >100 | >100 | >100 | |
| IVF6 | 0.94 | 8.03 | 1.88 | 9.5 | 5.088 | 67.89 | >100 | >100 | 67.69 | |
| IVA25 | 1.04 | 3.55 | 0.71 | 2.3 | 1.900 | >100 | >100 | >100 | >100 | |
| IVA27 | 0.94 | 1.32 | 0.62 | 0.71 | 4.691 | >100 | >100 | >100 | >100 | |
| | 5.06 | 8 | 1.88 | 19 | | >100 | >100 | >100 | >100 | |
| IVA6 | 0.54 | 0.51 | 0.29 | 0.24 | 0.395 | >100 | >100 | >100 | >100 | |
| IVA22 | 0.739 | 1.66 | 0.711 | 0.937 | 1.012 | >100 | >100 | >100 | >100 | |

*shown in FIG. 12.

A set of PAs wherein positions R$_1$ and R$_2$ of formula I are substituted by an aliphatic chain with varying degrees of unsaturation in the hydrocarbon chain are represented in FIG. 2, Series III. These compounds include those with internal geometrically cis (zusammen or Z-form) and trans (entgegen or E-form) isomers are also presented in this series.

In addition to lipophilicity effects, the invention incorporates considerations based on the charge character of the PA. As obvious from the above general formula II for PAs of the invention, the introduction of the R$_1$X{O}$_n$— and R$_2$X{O}$_n$— moieties reduces the number of positive charges in the analog or derivative by one. At physiological pH of 7.2 the vast majority of amine groups will be in their positively charged ammonium state. The importance of positive charges for inhibiting polyamine transport is suggested by the observation that a PA with acetamide (IA11) showed a higher EC$_{50}$ in comparison to analogous PAs wherein both R$_1$X{O}$_n$— and R$_2$X{O}$_n$— are replaced by hydrogen atoms (see IA11 versus ORI 1202 and ORI 1426 in Table 3).

Series IV (see FIG. 2) incorporates the above considerations for both lipophilicity and positive charges by incorporating both a long hydrocarbon chain and retaining the positively charged ammonium function. The reductive amination used to produce these structures results in alkylated (instead of acylated) amines. These compounds are inferred to have great affinity for the polyamine transporter. PAs with a dimerized spermine structure, represented by structures such as IA19, showed no improvement over the original lysine-spermine conjugate.

An alternative group of PAs, based on the long-chain hydrocarbon containing carboamides (FIG. 2, Series I), may be prepared by incorporating the lipophilic and biologically stable sulfonamide group. These PAs are shown in FIG. 2, Series II. Without being bound by theory, it may be that the addition of an additional carbonyl-like oxygen atom in the sulfonamide series increases the interactions at an amide-binding domain of polyamine transporters. An additional factor which may be playing a role is the increased lipophilicity in sulfonamides versus carboxamides. Additionally sulfonamides are known to be more biologically stable in comparison to carboxamides.

The present invention also provides additional ways to increase the lipophilicity of the substituents on the PA molecule. Alternatives with additional alkyl groups on the acyl portion of the molecule will increase the lipophilicity of this group and thus give an analog with higher activity. One additional method to increase this lipophilicity is through attachment of an additional alkyl chain alpha to the amino group (substituent which is attached to the carbon atom attached to the nitrogen). These analogs are produced by reductive amination of the free amino precursor with one of the ketone reagents shown in Series V. An additional advantage provided by inclusion of a methyl, or other substituent, at the alpha position of the amine group is decreased rate of biological metabolism.

An additional method to increase the lipophilicity of the analogs is through the production of a tertiary amine at the proximal or distal, or both, nitrogen atoms of the molecule. These molecules, which are shown in Series VI, are produced via the reductive amination reaction using a free mono- or di-amine precursor and an excess of the carbonyl containing reagent shown in Series VI. An alternative method to produce these di-substituted tertiary amine containing molecules is the conjugate addition of the selectively protected amine precursor to an $\alpha,\beta$-unsaturated carbonyl compound or an $\alpha,\beta$-unsaturated nitrile compound.

Figure 1B:
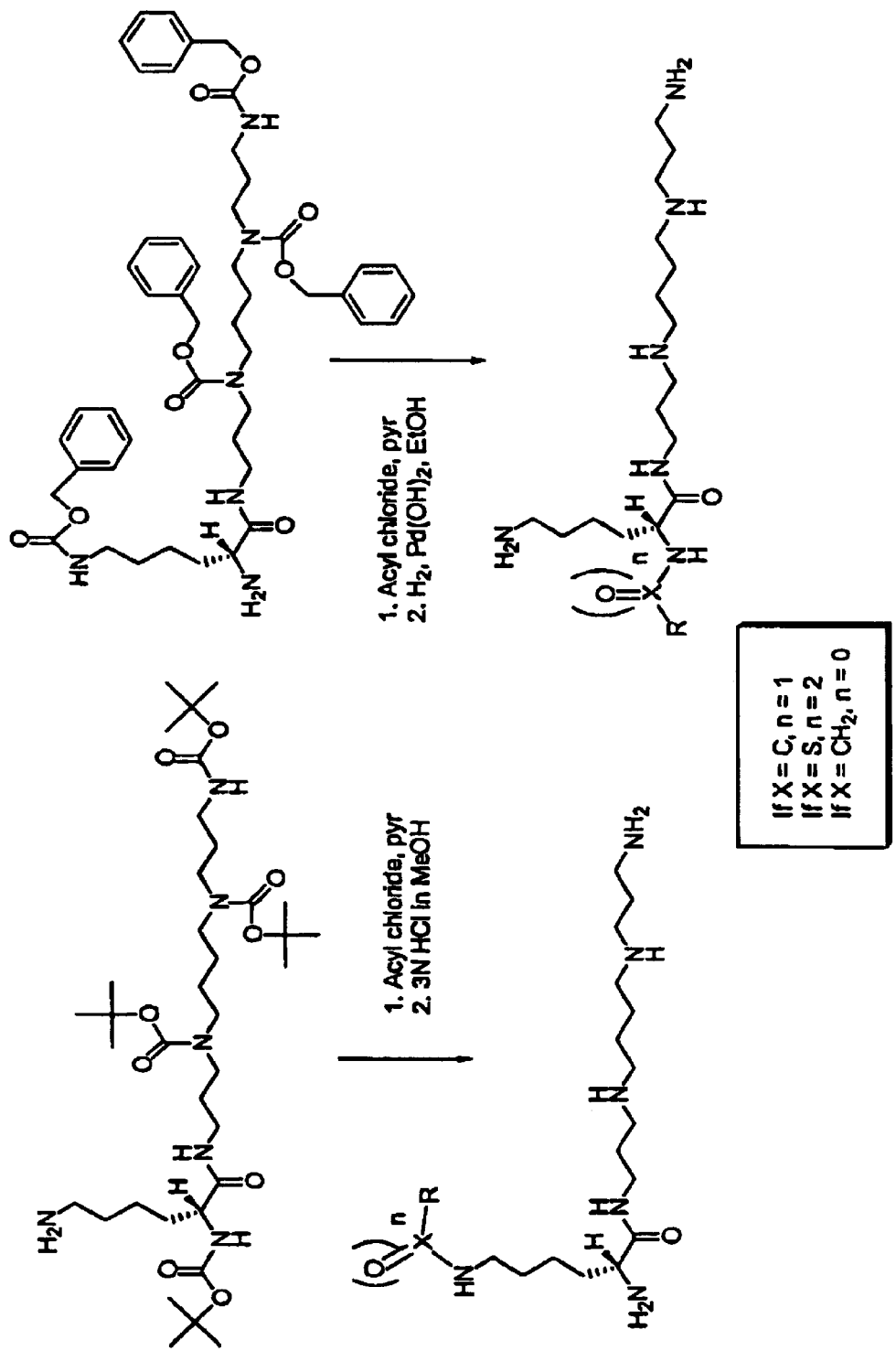

The present invention further provides methods for the synthesis of the disclosed PAs. In general, an orthogonally protected diamine containing compound, such as, but not limited to, certain amino acids, is coupled to a primary amine group of a polyamine followed by deprotection of one or both of the protected amine groups followed optionally by further derivatization of the amine. Without limiting the scope of the invention, an exemplary scheme for the production of spermine based PAs according to the above formula wherein d is 4, e is 0, X is C, and either R$_1$X{O}$_n$— or $R_2X\{O\}_n$— is H is shown in FIG. 1, where the 4-nitrophenyl activated ester Boc-L-Lys-(Cbz)-ONP is used in combination with spermine. This scheme is for illustrative purposes only, and any other diamino containing amino acid including, but not limited to, D-lysine, L-ornithine, D-omithine, L-2,4-diaminobutyric acid, D-2,4-diaminobutyric acid, L-2,3-diaminopropionic acid and D-2,3-diaminopropionic acid can be likewise orthogonally di-protected and coupled to spermine. Any appropriate protecting group(s) may be used in the practice of the invention, and the indication of Boc-(butoxycarbonyl-) and Cbz-(carbobenzoxy-) protecting groups are for illustrative purposes only. Other protective group strategies are known in the art (see, for example, "Protective Groups in Organic Synthesis—Third Ed. 1999, eds. T. W. Greene and P. G. M. Wuts. John Wiley and Sons, Inc. New York).

In another aspect of the invention, polyamine analogs may be prepared via the coupling of distal carboxylic acid containing amino acids with suitable protecting groups on this distal carboxylic acid (e.g. methyl or benzyl ester) such as $N$-$^t$Boc-Asp(OCH$_3$)—OH or $N$-$^t$Boc-Glu(OCH$_3$)—OH with a primary amine group of a polyamine (such as, but not limited to, spermine) followed by exhaustive protection of the remaining amino groups. After purification by silica gel chromatography the distal carboxylic acid is deprotected and reacted with long chain hydrocarbon containing amines or alcohols to give amides or esters respectively. Such polyamine analogs can be represented by the following structure

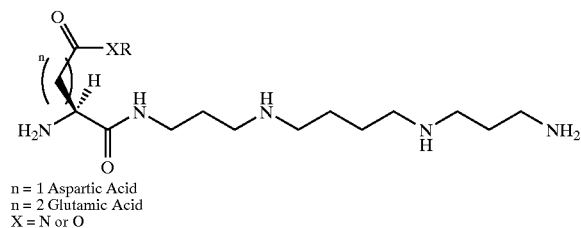

n = 1 Aspartic Acid
n = 2 Glutamic Acid
X = N or O wherein n can also be greater than 2, preferably up to about 10 (including 3, 4, 5, 6, 7, 8 and 9) and R is defined as provided for $R_1$ and $R_2$ in formula II above. The alpha amino group of the distal carboxylic acid containing amino acid may also be derivatized as described above in Formula II. Such compounds may be described as "inverted" amide or ester derivatives of the compounds described in FIG. 2.

Similar hydrophobic PAs can be prepared by the use of cysteine, serine, or homo serine to link the hydrophobic and polyamine moieties indirectly. The hydrophobic PAs may also be linked via an ester linkage (like that possible via serine), a thioester linkage (like that possible via cysteine), a urea linkage (—N—CO—N—), a carbamate linkage (—O—CO—N— or —N—CO—O—), or an extended sulfonamide linkage (—NH—SO$_2$—), As shown in FIG. 1, the active ester is added to an excess of polyamine to produce a mixture of substituted and unsubstituted acyl polyamines. The remaining free amino groups of the polyamines can then be protected, such as via their $^t$Boc or Cbz carbamates, and the desired orthogonally-protected products can be isolated. Full protection of the amino groups produces a more lipophilic product mixture which facilitates purification of the desired compound. The exemplary reaction scheme in FIG. 1 results in two synthetic intermediates, one with 4 Boc and 1 Cbz carbamates and the other with 4 Cbz and 1 Boc carbamates. These intermediates allow the exposure of selectively either the distal or proximal (relative to the starting spermine polyamine) amino groups to be selectively deprotected by catalytic hydrogenation (see left branch of scheme) or acid treatment (see right branch of scheme), respectively. When viewed relative to the lysine moiety, the distal and proximal amino groups may be considered the ε- or α-amino positions, respectively.

The deprotected amino groups may then be further modified via conventional amide chemistry. For example, and without limiting the invention, the deprotected amino groups may be acylated or alkylated with either an acyl chloride or sulfonyl chloride to produce PAs shown in FIG. 2 as Series I and II, respectively. The positions may also be carboxylic acid activated with standard peptide coupling reagents such as DCC, PyPOP or HBTU (to produce Series III PAs) or aldehydes using reductive amination conditions (to produce Series IV PAs). Additional analogs are produced by reductive amination of the free amino precursor with one of the ketone reagents shown in Series V. Series VI analogs are produced via the reductive amination reaction using a free mono- or di-amine precursor and an excess of the carbonyl containing reagent shown in the Series VI portion of FIG. 2. An alternative method to produce these di-substituted tertiary amine-containing molecules is the conjugate addition of the selectively protected amine precursor to an α,β-unsaturated carbonyl compound or an α,β-unsaturated nitrile compound.

The above described synthetic schemes may be conducted in a parallel fashion to permit the simultaneous production of multiple PAs. For example, the reaction scheme shown in FIG. 1 may be started with a mixture of L- and D-forms of Boc-Lys-(Cbz)-ONP and spermine. This results in a possible 4 different amino groups (two based on each of the L- and D-forms, and two based on each of the distal and proximal amino groups) deprotection and subsequent modification. There are also two additional possible modifications where both amino groups are simultaneously deprotected for subsequent modification. This results in a total of 6 possible routes for modification.

Parallel acylation with just two acyl chlorides, such as by solution phase methods, would produce twelve different PAs. Each individual PA may then be purified and the protective groups on the polyamine portion removed before further characterization and use.

The invention also provides compositions containing one or more PAs, as well as acceptable salts thereof, in combination with an excipient, diluent or vehicle to facilitate its use or administration to a subject. Preferably, the compositions are formulated for pharmaceutical, therapeutic or agricultural uses. Pharmaceutically acceptable salts of the invention (which contain basic groups) are formed where appropriate with strong or moderately strong, non-toxic, organic or inorganic acids in the presence of the basic amine by methods known in the art. Exemplary salts include, but are not limited to, maleate, fumarate, lactate, oxalate, methanesulfonate, ethanesulfonate, benzenesulfonate, tartrate, citrate, hydrochloride, hydrobromide, sulfate, phosphate and nitrate salts.

As stated above, the PAs of the invention possess the ability to inhibit polyamine transport, a property that is exploited in the treatment of any of a number of diseases or conditions, most notably cancer. A composition of this invention may be active per se, or may act as a "pro-drug" that is converted in vivo to active form.

The PAs of the invention, as well as the pharmaceutically acceptable salts thereof, may be incorporated into convenient dosage forms, such as capsules, impregnated wafers, tablets or injectable preparations. Solid or liquid pharmaceutically acceptable carriers may also be employed. Pharmaceutical compositions designed for timed or delayed release may also be formulated.

Optionally, the compositions contain anti-oxidants, surfactants and/or glycerides. Examples of anti-oxidants include, but not limited to, BHT, vitamin E and/or C. Examples of glycerides include, but are not limited to, one or more selected from acetylated or unsubstituted monoglycerides; medium chain triglycerides, such as those found in oils; and caprylocaproyl macrogol-8 glycerides.

Preferably, the compounds of the invention are administered systemically, e.g., by injection or oral administration. When used, injection may be by any known route, preferably intravenous, subcutaneous, intramuscular, intracranial or intraperitoneal. Injectables can be prepared in conventional forms, either as solutions or suspensions, solid forms suitable for solution or suspension in liquid prior to injection, or as emulsions.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, liquid containing capsule, sterile injectable liquid (e.g., a solution), such as an ampule, or an aqueous or nonaqueous liquid suspension. A summary of such pharmaceutical compositions may be found, for example, in *Remington's Pharmaceutical Sciences*, Mack Publishing Company, Easton Pa. (Gennaro 18th ed. 1990).

The pharmaceutical preparations are made following conventional techniques of pharmaceutical chemistry involving such steps as mixing, granulating and compressing, when necessary for tablet forms, or mixing, filling and dissolving the ingredients, as appropriate, to give the desired products for oral or parenteral administration. Other preparations for topical, transdermal, intravaginal, intranasal, intrabronchial, intracranial, intraocular, intraaural and rectal administration may also be prepared. The pharmaceutical compositions may also contain minor amounts of nontoxic auxiliary substances such as wetting or emulsifying agents, pH buffering agents and so forth.

Although the preferred routes of administration are systemic, the pharmaceutical composition may be administered topically or transdermally, e.g., as an ointment, cream or gel; orally; rectally; e.g., as a suppository, parenterally, by injection or continuously by infusion; intravaginally; intranasally; intrabronchially; intracranially; intraaurally; or intraocularly.

Intraaural formulations are particularly preferred for the treatment or alleviation of hearing loss due to chemotherapy.

For topical application, the compound may be incorporated into topically applied vehicles such as a salve or ointment. The carrier for the active ingredient may be either in sprayable or nonsprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Preferred vehicles for non-sprayable topical preparations include ointment bases, e.g., polyethylene glycol-1000 (PEG-1000); conventional creams; gels; as well as petroleum jelly and the like.

Topical preparations are particularly preferred for the application of the present invention to the control of unwanted hair growth on skin.

Also suitable for topical application are sprayable aerosol preparations wherein the compound, preferably in combination with a solid or liquid inert carrier material, is packaged in a squeeze bottle or in admixture with a pressurized volatile, normally gaseous propellant. The aerosol preparations can contain solvents, buffers, surfactants, perfumes, and/or antioxidants in addition to the compounds of the invention.

For the preferred topical applications, especially for humans, it is preferred to administer an effective amount of the compound to a target area, e.g., skin surface, mucous membrane, eyes, etc. This amount will generally range from about 0.001 mg to about 1 g per application, depending upon the area to be treated, the severity of the symptoms, and the nature of the topical vehicle employed.

The compositions of the invention may be administered alone or in combination with one or more additional compounds that are used to treat the disease or condition. For treating cancer, the PAs are given in combination with anti-tumor agents, such as mitotic inhibitors, e.g., vinblastine; alkylating agents, e.g., cyclophosphamide; folate inhibitors, e.g., methotrexate, pritrexim or trimetrexate; antimetabolites, e.g., 5-fluorouracil and cytosine arabinoside; intercalating antibiotics, e.g., adriamycin and bleomycin; enzymes or enzyme inhibitors, e.g., asparaginase; topoisomerase inhibitors, e.g., etoposide; or biological response modifiers, e.g., interferon and interleukin-2. In fact, pharmaceutical compositions comprising any known cancer therapeutic in combination with the PAs disclosed herein are within the scope of this invention. Such combinations may be utilized either by combining the components into a single composition for administration or by administering the components separately as part of one therapeutic protocol.

Most preferably, the present compounds are administered in combination with one or more polyamine synthesis inhibitors such as, but not limited to, inhibitors of ornithine decarboxylase such as DFMO, aceylenic putrescine, 1-aminooxy-3-aminopropane, antizyme, 2-butylputrescine, cadaverine, L-canaline, 5'-deoxy-5'-[N-methyl-N-[3-(aminooxy)ethyl]amino]adenosine, 5'-deoxy-5'-[N-methyl-N-[3-(hydrazinopropyl)amino]adenosine, diaminopropane, 1,3-diamino-2-propanol, 2-difluoromethyl putrescine, difluorophenylethyl(4-aminopropylamidinohydrazone), 2,3-dimethylputrescine, N-dimethylputrescine, 2-ethylputrescine, (+ or −)-alpha-fluoromethylornithine, 2-fluoro methylputrescine, 2-hexylputrescine, 2-hydrazinoornithine, ibuprofen, D-methyl acetylenic putrescine, methylglyoxal bis(3-aminopropyl-amidinohydrazone), 2-methylornithine, 2-methylputrescine, 2-monofluoromethyl-trans-dehydroornithine, 2-monofluoromethyl dehydroputrescine, monofluoromethylornithine, 2-monofluoromethyl putrescine, neomycin, D-ornithine, 2-pentylputrescine, p-phenylenediamine, phosphopeptide MG 25000, phosphothreonine, phosphotyrosine, 2-propylputrescine, putrescine, allo-S-adenosyl-L-methionine, S-ethylthioadenosine, methylthioadenosine, and 5'-methylthioadenosine as discussed in Zollner H. (1993) Handbook of Enzyme Inhibitors, 2nd Ed. Weinheim:Basel (Switzerland); inhibitors of S-adenosylmethionine decarboxylase, such as SAM486A (4-aminoindanon-1-

(2'amidino)hydrazone dihydrochloride monohydrate), S-adenosyl-1,8-diamino-3-thiooctane, S-(5'-adenosyl) methylthio-2-aminooxyethan, S-adenosyl-3-methylthio-1-propylamine, 5'-{[(Z)-4-amino-2-butenyl]methylamino}-5'-deoxyadenosine, 5'-amino-5'-deoxyadenosine, 5'-[(aminoiminomethyl)amino]-5']deoxyadenosine dihydrogensulphate, 1-aminooxy-3-aminopropane, [2-(aminooxy)ethyl](5'-deoxyadenosine-5'-yl)(methyl) sulphonium, 5'-[(3-aminopropyl)-amino)-5'-deoxyadenosine, 5'-[(3-aminopropyl]-nethylamino)-5'-deoxyadenosine, 9-[6(RS)-amino-5,6,7-trideoxy-beta-D-ribo-octofuranosyl]-9H-purin-6-amine, borohydride, n-butylglyoxal bis(guanylhydrazone), 9-[6(RS)-c-carboxamido-5,6,7-trideoxy-beta-D-ribo-octofuranosyl]-9H-purin-6-amine, cyanide, cyanoborohydride, S-(5'deoxy-5'adenosyl)methionylethylhydroxylamine, S-(5'deoxy-5'adenosyl)methionylthiohydroxylamine, 5'-deoxy-5'-[N-methyl-N-[2-(aminooxy)ethyl]amino]adenosine, 9-[6(S)-diamino-5,6,7,8,9-pentadeoxy-beta-D-ribo-nanofuranosyl]-9H-purin-6-amine, diethylglyoxal bis(guanylhydrazone), difluorophynylethyl (4-aminopropylamidinohydrazone), dimethyl(5'-adenosyl)sulfonium, dimethylglyoxal bis (guanylhydrazone), ethylglyoxal bis(guanylhydrazone), hydroxylamine, 4-hydroxypenenal, MDL 73811, 5'[[3-methylamino)propyl]amino]-5'-deoxyadenosine(1,1'-(methylethanediylidine)dinitro)bis(3aminoguanididne), methylglyoxal bis(3-aminopropylamidinohydrazone), methylglyoxal bis(cyclohexylamidinohydrazone), methylglyoxal bis(guanylhydrazone), pentanedialdehyde bis guanylhydrazone), phenylbydrazine, propanedialdehyde bis (guanylhydrazone), semicarbazide, sodium borohydride, sodium cyanoborohydride, and spermine as discussed in Zollner H. (1993) Handbook of Enzyme Inhibitors, 2nd Ed.

The PAs of the invention may also be used in combination with monoclonal antibodies and tumor vaccines as well as with cellular therapy in subjects undergoing treatment for human diseases such as cancer. The PAs may also be used for chemoprevention in subjects at risk for developing cancer wherein one or more PAs are taken alone or in combination with a polyamine synthesis inhibitor to prevent the onset or recurrence of cancer.

The pharmaceutical compositions of the invention may also comprise one or more other medicaments such as anti-infectives including antibacterial, anti-fungal, anti-parasitic, anti-viral, and anti-coccidial agents.

Typical single dosages of the compounds of this invention are between about 1 ng and about 10 g/kg body weight. The dose is preferably between about 0.01 mg and about 1 g/kg body wt. and, most preferably, between about 0.1 mg and about 100 mg/kg body wt. For topical administration, dosages in the range of about 0.01–20% concentration of the compound, preferably 1–5%, are suggested. A total daily dosage in the range of about 1–500 mg is preferred for oral administration. The foregoing ranges are, however, suggestive, as the number of variables in regard to an individual treatment regime is large, and considerable excursions from these recommended values are expected and may be routinely made by those skilled in the art.

Effective amounts or doses of the compound for treating a disease or condition can be determined using recognized in vitro systems or in vivo animal models for the particular disease or condition. In the case of cancer, many art-recognized models are known and are representative of a broad spectrum of human tumors. The compounds may be tested for inhibition of tumor cell growth in culture using standard assays with any of a multitude of tumor cell lines of human or nonhuman animal origin. Many of these approaches, including animal models, are described in detail in Geran, R. I. et al., "Protocols for Screening Chemical Agents and Natural Products Against Animal Tumors and Other Biological Systems (Third Edition)", *Canc. Chemother. Reports*, Part 3, 3:1–112.

The present invention also provides methods of using the PAs, whether formulated in compositions or not, to inhibit cell growth and proliferation when used alone or in combination with a polyamine synthesis inhibitor. Such methods may be readily conducted by systemic or local administration of the PAs. Local delivery of a PA provides a high local concentration while reducing the likelihood of systemic effects on polyamine metabolism that may result from systemic PA administration.

The inhibition of cellular growth and proliferation is advantageously conducted with the contemporaneous administration of one or more inhibitors of polyamine synthesis. Such inhibition may be applied toward a variety of cell types, including, but not limited to, bacterial cells, fungal cells, and the eukaryotic cells of higher multicellular organisms. In one application of the invention, one or more PAs may be used to inhibit bacterial or fungal cell growth. This embodiment may be advantageously used in both the clinic and agriculture to control bacteria or fungi.

In another embodiment of the invention, one or more PAs may be used in combination with an inhibitor of polyamine synthesis to inhibit the growth and/or proliferation of cancer cells, including those of solid tumors. While this latter application may be performed in any multicellular organism, most preferred are applications of the invention for use in human subjects.

Additionally, the invention provides for the use of one or more PAs for analytical and/or preparative methods relating to polyamine transport. For example, and without limiting the invention, a PA may be used to identify and/or localize a polyamine transporter by virtue of physical binding between the PA and the transporter and the presence of a label linked to the PA. Suitable labels are well known in the art, and they permit the identification or localization of the PA either because the label itself emits a detectable signal, or by virtue of its affinity for a label-specific partner which is detectable or becomes so by binding to, or otherwise reacting with, the label. Examples of labels include, but are not limited to, radioactive isotopes, fluorescent tags, and proteinaceous tags. The methods of identification and /or localization provided by the invention may be used in whole or as part of a diagnostic or research protocol.

The invention also provides preparative uses of the PAs. For example, one or more PAs can be used to bind and isolate proteins or other cellular factors that interact with polyamines. An exemplar of such a method is the use of a PA to bind to a polyamine transporter and permit its isolation or purification. These methods can be performed in solution, where interaction between a PA and a PA binding protein or factor results in a complex that may be subsequently isolated or purified from solution, or in solid phase, where a PA is immobilized and interactions between the PA and a PA binding protein or factor results in a complex of the protein or factor with the immobilized PA.

Having now generally described the invention, the same will be more readily understood through reference to the following examples which are provided by way of illustration, and are not intended to be limiting of the present invention, unless specified.

EXAMPLE I

Chemical Synthesis of Polyamine Agents (PAs)

PAs analogs were synthesized in a parallel fashion starting from the orthogonally protected diamino containing amino acid starting materials. The use of the 4-nitrophenyl activated ester L-Boc-Lys-(Cbz)-ONP in FIG. 1 provides an exemplary illustration of the synthetic process. The active ester is added dropwise to a solution of 1.5 equivalents of polyamine in methanol to give a statistical mixture of unsubstituted, mono-substituted and di-substituted acyl polyamines. Following evaporation of the solvent, the remaining free amino groups in the polyamine moiety are protected either as their 'Boc or Cbz carbamates. Standard workup results in a completely protected crude product mixture. The desired orthogonally-protected product is isolated in pure form by silica gel chromatography using standard organic solvents. This purification process is based on separation of polyamine molecules with the remaining amino groups being fully protected, which provides a much more lipophilic product mixture that greatly facilitates the purification process. Thus the exemplary intermediates containing either 4 Boc groups or 4 Cbz groups in addition to the acyl functionality remained lipophilic enough to purify using standard solvents including a one to one mixture of ethyl acetate and hexanes containing various proportions of methanol (0 to 10%).

As shown in FIG. 1, the approach provides two synthetic intermediates, one with 4 Boc and 1 Cbz carbamates and the other with 4 Cbz and 1 Boc carbamates. These intermediates allow the exposure of only one amino group, either the proximal ($\alpha$-) or distal ($\epsilon$-), in a selective manner. It is also possible to modify this approach such that both amino groups are exposed for further modification. The selective deprotection of either the proximal ($\alpha$-) or distal ($\epsilon$-) amino group as shown in FIG. 1 may occur via catalytic hydrogenation or acid treatment, respectively. The exposed amino groups were then acylated or alkylated with either an acyl chloride or sulfonyl chloride to produce Series I and II (see FIG. 2) type PAs, respectively. The exposed amino groups may also be carboxylic acid activated with standard peptide coupling reagents such as DCC, PyPOP or HBTU (to produce Series III type PAs) or aldehydes under reductive amination conditions (to produce Series IV type PAs). Additional analogs are produced by reductive amination of the free amino precursor with one of the ketone reagents shown in Series V. Series VI analogs are produced via the reductive amination reaction using a free mono- or di-amine precursor and an excess of the carbonyl reagent that are shown in the Series VI chart. An alternative method to produce these di-substituted tertiary amine-containing molecules is the conjugate addition of the selectively protected amine precursor to an $\alpha$, $\beta$-unsaturated carbonyl compound or an $\alpha$, $\beta$-unsaturated nitrile compound.

Deprotections of isolated PAs using standard conditions gave the desired products in pure form. The PAs were characterized by thin layer chromatography (TLC) analysis (using 'PrOH/HOAc/pyr/H$_2$O, 4:1:1:2); high performance liquid chromatography (HPLC) analysis (dansylation followed by HPLC using fluorescent detection); liquid chromatography-mass spectroscopy (LC-MS) by electrospray ionization; and $^1$H and $^{13}$C NMR analysis. All PAs were estimated to be 90 to 98% pure following synthesis.

EXAMPLE II

Cell Culture and Reagents

All cell lines were obtained from ATCC (Manassas, Va.) and cultured in the recommended media, serum, and CO$_2$ concentration. Medias were obtained from Mediatech, Inc. (Herdon, Va.) and serums from Gibco BRL (Gaithersburg, Md.). 50 U/ml penicillin, 50 $\mu$g/ml streptomycin and 2 mM L-glutamine (all from Bio Whittaker, Walkersville, Md.) were included in all cultures. DFMO was obtained from Marion Merrell Dow (Cinncinati, Ohio). When cells were cultured with polyamines or ORI compounds, 1 mM aminoguanidine (AG; Sigma) was included to inhibit serum amine oxidase activity. IC$_{50}$ refers to the concentration of PA that results in 50% of maximum cell growth inhibition in the presence of PA alone.

EXAMPLE III

Polyamine Transport and Ki Assays

[2,9-$^3$H]spermidine (SPD) from DuPont NEN, Boston, Mass. was added alone or simultaneously with PAs to 24-well plates containing MDA-MB-23 1 cells in log growth. The cells were incubated at 37° C. for 15 min to determine initial rate polyamine uptake. The cells were then washed three times with cold PBS, lysed with 0.1% SDS, and the amount of polyamine incorporation into the cells was determined by scintillation counting of the cell lysates. To determine a K$_i$, four radioactive substrate concentrations (0.3–3 $\mu$M) and five inhibitor concentrations (0.01–1.0 $\mu$M) and a control were tested. The K$_i$ values were determined using double reciprocal Lineweaver-Burke plot analyses. K$_i$ values were determined from linear equations derived from graphing the slopes of Lineweaver-Burke plot vs. inhibitor concentration, with K$_i$=y-intercept/slope. Results of these analyses are shown in Table 3 above.

EXAMPLE IV

Growth Inhibition Assay

Cells were plated in 96-well plates such that they would be in log growth for the duration of the assay. The day after plating, PAs were added to the cells, and growth, if any, permitted to continue for six days in the presence of 1 mM AG and 0.5 $\mu$M SPD to insure that any growth inhibition was not the result of depletion of external polyamines in the media. At the end of the six days, cell growth was measured by MTS/PMS dye assay (Cell Titer 96 Aqueous Non-Radioactive Cell Proliferation Assay; Promega, Madison, Wis.). EC$_{50}$ represents the concentration of PA that resulted in 50% of maximum growth inhibition achievable in the presence of both DFMO (5 mM in all cell lines except MDA) and PA (at different concentrations depending in part on the cell line used) compared to controls. IC$_{50}$ represents the concentration of PA that resulted in 50% maximum growth inhibition when used alone. Results are shown in Table 3 above.

EXAMPLE V

HPLC Analysis of Dansylated Derivatives

Sample handling for Polyamine Analysis (see Kabra, Pokar M., Hsian K. Lee, Warren P Lubich and Laurence J. Marton: Solid-Phase Extraction and Determination of Dansyl Derivatives of Unconjugated and Acetylated Polyamines by Reverse-Phase Liquid Chromatography: Improved Separation Systems for Polyamines in Cerebrospinal Fluid, Urine and Tissue. Journal of Chromatography 380 (1986) 19–32)

Plasma samples (from blood)—remove 125–150 $\mu$l sample (optimally) into a microfuge tube and mix 1:1 with 0.4M perchloric acid. Vortex and spin down sample at 13000 rpm for 10 minutes in 5° C. centrifuge. Remove 200 $\mu$l supernatant for dansylation as described in dansylation protocol. Plasma samples as small as 25 $\mu$l may be analyzed (for this and the following discussion, any sample that does not yield 200 µl supernatant for dansylation may have its volume increased to 200 µl with perchloric acid for the dansylation protocol).

Cell Culture Samples

Media—remove 1.5 ml into 1.7 ml microfuge tube and spin at 3000 rpm for 5 minutes in 5° C. centrifuge. Remove 300 µl supernatant and mix 1:1 with cold 0.4M perchloric acid. Vortex and spin down sample at 13000 rpm for 10 minutes in 5° C. centrifuge. Remove 200 µl supernatant for dansylation as described in dansylation protocol.

Cells—Trypsinize as usual and spin in 15 ml tube 6 min at 4° at 1500 rpm. Pour off supernatant and resuspend pellet in 1.5 ml 1× PBS. Transfer to large microfuge tube. Spin at 3000 rpm at 4° for 5 minutes. Remove supernatant. Resuspend pellet in 1.0 ml 1× PBS. Remove 20 µl for counting and spin @ 3000 rpm @4° for 5 minutes. Remove supernatant. To the dry pellet, add 200 µl 0.4M perchloric acid per $10^6$ cells. Pipette up and down to mix. Vortex and spin down sample at 13000 rpm for 10 minutes in 5° C. centrifuge. Remove 200 µl supernatant for dansylation as described in dansylation protocol. Remainder of supernatant can be stored at −70° C.

Tissues—Keep samples on ice during preparation. Cut an approximately 100 mg piece from tissue sample and place into 15 ml conical tube. Add 1.2M perchloric acid in a 20:1 vol/weight ratio (i.e. 2 ml/100 mg). Homogenize tissue using a tissue grinder. Vortex sample and remove 1 ml into a microfuge tube. Spin at 13000 rpm for 10 minutes in 5° C. centrifuge. Remove 200 µl supernatant for dansylation as described in dansylation protocol.

Dansylation Protocol for Polyamine Analysis

200 µl sample in Perchloric acid

10 µl Internal Standard (IS) (1,7-diaminoheptane, 100 µM stock); use 20 µl for 25 min and 1483 HPLC 120 µl saturated sodium carbonate solution (360 µl is used for tissue samples)

400 µl dansyl chloride solution (made fresh, 10 mg/ml in acetone)

Add all ingredients to a 4 ml screw cap glass vial and vortex for 30 seconds. Float vials in 70° C. water bath for 10 minutes. Remove and allow cooling to room temp in dark, as samples are light sensitive. Proceed to sample prep protocol once samples have cooled.

Sample Prep Protocol

Alltech C-18 maxi-prep cartridges are used, one for each sample dansylated, to clean any interfering reactions from the samples. This process also places the samples in methanol for application to the HPLC system.

Each cartridge is placed on a vacuum manifold and washed once with 3 ml MeOH followed by 3 ml H₂O. Samples are then removed by 1 ml syringe from the glass vials and applied to the Alltech cartridges. Each cartridge is then washed with 10 ml H₂O and dried 2× with 30 cc syringe of air.

All steps to this point are allowed discarded. The cartridges are placed with a tube rack with labeled 1.7 ml microfuge tubes for elution. Samples are eluted with 1 ml MeOH into the microfuge tubes. Samples are now ready for injection onto HPLC or can be stored at −70° C. for up to several months if necessary.

The solvents used in the above are as follows:

Solvent A: HPLC grade Acetonitrile

Solvent B: 10 mM Na acetate pH 4.5/10% acetonitrile (8.9L H₂O, 1L Acetonitrile, 100 ml 1M Na acetate pH 4.5, mix well, filter and store at room temp).

Sample Injection: loop overfill is achieved by injecting 100 µl onto a 20 µl loop. Samples are kept at 4° C. until injection by a water cooled storage rack on the 231XL auto injector.

40 Minute PA Analysis:

| Gradient: | time | % A | % B |
|---|---|---|---|
| | 0 | 48 | 52 |
| | 25 | 90 | 10 |
| | 30 | 100 | 0 |
| | 35 | 48 | 52 |
| | 40 | 48 | 52 |

Flow rate is 3 ml/minute

Solutions and Sources are as follows:

Internal Standard:

1,7-Diaminoheptane (Sigma D-3266)

Made up 20 mM in H₂O, and stored at −70° C. Diluted to 100 µM working stock in H₂O and also stored at −70° C.

Perchloric acid:

70% ACS reagent (Aldrich 244252)

For 0.4 M, mix 3.4 ml in a total of 100 ml H₂O. Store at room temp.

For 1.2 M, mix 10.2 ml in a total of 100 ml H₂O. Store at room temp.

Sodium carbonate:

anhydrous (Acros 42428-5000)

Make a saturated solution in H₂O.

Sodium acetate:

anhydrous (Sigma S-2889)

Make up 1 M in H₂O, then pH to 4.5 with glacial acetic acid.

Filter and store at room temp.

Dansyl chloride:

95% (Sigma D-2625)

Acetonitrile:

HPLC grade (Fisher A998-4)

Methanol:

HPLC grade (Fisher A452-4)

Acetone:

HPLC grade (Fisher A949-1)

Glacial acetic acid:

ACS reagent (Fisher A38212)

All references cited herein, including patents, patent applications, and publications, are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A polyamine analog or derivative represented by formula II:

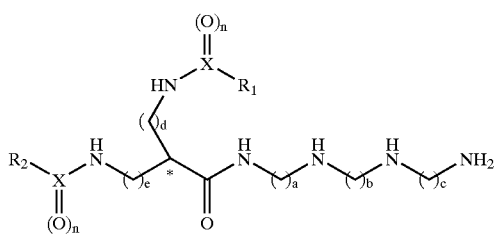

wherein a, b, and c independently range from 1 to 10; d and e independently range from 0 to 30; each X is independently either a carbon (C) or sulfur (S) atom, and $R_1$ and $R_2$ are independently selected from H or from the group of a straight or branched C1–50 saturated or unsaturated aliphatic, carboxyalkyl, carbalkoxyalkyl, or alkoxy; a C1–8 alicyclic; a single or multiring aryl substituted or unsubstituted aliphatic; an aliphatic-substituted or unsubstituted single or multiring aromatic; a single or multiring heterocyclic; a single or multiring heterocyclic aliphatic; a C1–10 alkyl; an aryl sulfonyl; or cyano; or each of $R_1X\{O\}_n$— and $R_2X\{O\}_n$— are independently replaced by H;

wherein * denotes a chiral carbon position; and wherein if X is C, then n is 1; if X is S, then n is 2; and if X is C, then the XO group may be $CH_2$ such that n is 0.

2. A polyamine analog or derivative represented by formula III:

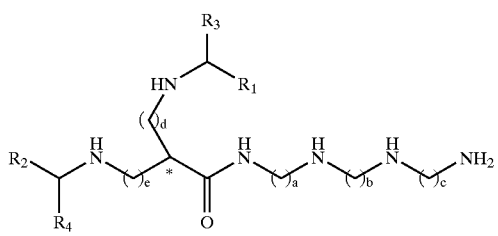

wherein a, b, and c independently range from 1 to 10 and d and e independently range from 0 to 30; and $R_1$, $R_2$, $R_3$, and $R_4$ may be the same or different and are independently selected from H or from the group of a straight or branched C1–50 saturated or unsaturated aliphatic, carboxyalkyl, carbalkoxyalkyl, or alkoxy; a C1–8 alicyclic; a single or multiring aryl substituted or unsubstituted aliphatic; an aliphatic-substituted or unsubstituted single or multiring aromatic; a single or multiring heterocyclic; a single or multiring heterocyclic aliphatic; a C1–10 alkyl; an aryl sulfonyl; or cyano.

3. A polyamine analog or derivative represented by formula IV:

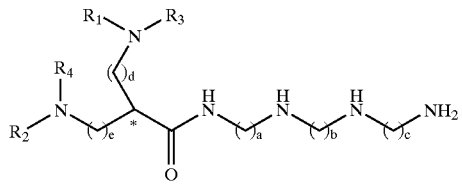

wherein a, b, and c independently range from 1 to 10 and d and e independently range from 0 to 30; and $R_1$, $R_2$, $R_3$, and $R_4$ may be the same or different and are independently selected from H or from the group of a straight or branched C1–50 saturated or unsaturated aliphatic, carboxyalkyl, carbalkoxyalkyl, or alkoxy; a C1–8 alicyclic; a single or multiring aryl substituted or unsubstituted aliphatic; an aliphatic-substituted or unsubstituted single or multiring aromatic; a single or multiring heterocyclic; a single or multiring heterocyclic aliphatic; a C1–10 alkyl; an aryl sulfonyl; or cyano.

4. A polyamine analog or derivative represented by formula V:

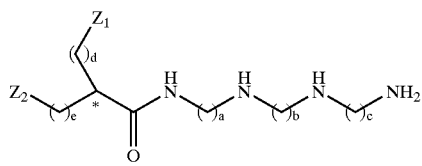

wherein a, b, and c independently range from 1 to 10 and d and C independently range from 0 to 30; and wherein $Z_1$ is $NR_1R_3$ and $Z_2$ is selected from —$R_1$, —$CHR_1R_2$ or —$CR_1R_2R_3$ or $Z_2$ is $NR_2R_4$ and $Z_1$ is selected from —$R_1$, —$CHR_1R_2$ or —$CR_1R_2R_3$, wherein $R_1$, $R_2$, and $R_3$ may be the same or different and are independently selected from H or from the group of a straight or branched C1–50 saturated or unsaturated aliphatic, carboxyalkyl, carbalkoxyalkyl, or alkoxy; a C1–8 alicyclic; a single or multiring aryl substituted or unsubstituted aliphatic; an aliphatic-substituted or unsubstituted single or multiring aromatic; a single or multiring heterocyclic; a single or multiring heterocyclic aliphatic; a C1–10 alkyl; an aryl sulfonyl; or cyano.

5. The analog or derivative of claims 1–4 wherein said a, b, and c are such that the analog or derivative is putrescine, spermine or spermidine based.

6. The analog or derivative of claims 1–4 wherein each of $R_1$, $R_2$, $R_3$, and $R_4$ is independently selected from H or a straight or branched C10–50 saturated or unsaturated aliphatic, carboxyalkyl, carbalkoxyalkyl, or alkoxy.

7. A polyamine analog or derivative selected from spermine based compounds IA4, IB4, IA7, IVB22 or IVA22 as illustrated in FIG. 2.

8. A polyamine analog or derivative selected from the compounds depicted in FIG. 12.

9. The analog or derivative of claims 1–4 wherein d is 4 and e is 0.

10. The analog or derivative of claims 1–4 wherein each of $R_1$, $R_2$, $R_3$, and $R_4$ is independently selected from H or from

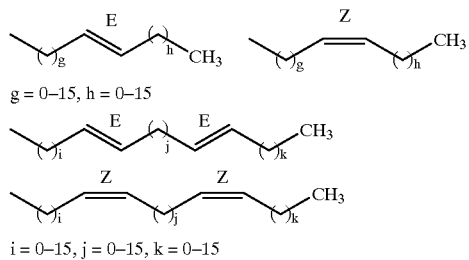

g = 0–15, h = 0–15 i = 0–15, j = 0–15, k = 0–15 wherein each of g, h, i, j, and k are independently selected from 0 to 15 and wherein E refers to "entgegen" and Z refers to "zusammen".

11. A composition comprising a polyamine analog or derivative according to claims 1–4 and an excipient, diluent or vehicle.

12. The composition of claim 11 wherein said excipient, diluent or vehicle is pharmaceutically or cosmetically acceptable.

13. The composition of claim 11 wherein said excipient, diluent or vehicle is for topical or intra-aural administration.

14. The composition of claim 11 further comprising a polyamine biosynthesis inhibitor.

15. The composition of claim 14 wherein said inhibitor is DFMO.

16. The composition of claim 11 formulated for intravenous, subcutaneous, intramuscular, intracranial, intraperitoneal, topical, transdermal, intravaginal, intranasal, intrabronchial, intracranial, intraocular, intraaural, rectal, or parenteral administration.

* * * * *

UNITED STATES PATENT AND TRADEMARK OFFICE
CERTIFICATE OF CORRECTION

PATENT NO. : 6,963,010 B2
DATED : November 8, 2005
INVENTOR(S) : Mark R. Burns et al.

It is certified that error appears in the above-identified patent and that said Letters Patent is hereby corrected as shown below:

<u>Title page,</u>
Item [75], Inventors, add -- Nand Baindur --.

Signed and Sealed this

Eleventh Day of April, 2006

JON W. DUDAS
*Director of the United States Patent and Trademark Office*